United States Patent
Paterson et al.

(10) Patent No.: US 7,794,729 B2
(45) Date of Patent: Sep. 14, 2010

(54) METHODS AND COMPOSITIONS FOR IMMUNOTHERAPY OF CANCER

(75) Inventors: Yvonne Paterson, Philadelphia, PA (US); Reshma Singh, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 613 days.

(21) Appl. No.: 10/949,667

(22) Filed: Sep. 24, 2004

(65) Prior Publication Data

US 2005/0129715 A1    Jun. 16, 2005

Related U.S. Application Data

(63) Continuation-in-part of application No. 10/441,851, filed on May 20, 2003, now Pat. No. 7,135,188, which is a continuation of application No. 09/535,212, filed on Mar. 27, 2000, now Pat. No. 6,565,852, which is a continuation-in-part of application No. 08/336,372, filed on Nov. 8, 1994, now Pat. No. 6,051,237.

(51) Int. Cl.
*A61K 39/02* (2006.01)
*A61K 38/04* (2006.01)
*A61K 38/16* (2006.01)

(52) U.S. Cl. .............. 424/200.1; 424/93.1; 424/93.2; 424/93.21; 424/184.1; 424/190.1; 424/192.1; 424/207.1; 424/210.1; 424/234.1; 424/237.1

(58) Field of Classification Search ............ 424/234.1, 424/93.4, 184.1, 93.1, 93.2, 93.21, 190.1, 424/192.1, 200.1, 207.1, 210.1, 237.1
See application file for complete search history.

(56) References Cited

U.S. PATENT DOCUMENTS

| | | | |
|---|---|---|---|
| 4,458,066 A | 7/1984 | Caruthers et al. |
| 4,521,382 A | 6/1985 | Kessick |
| 4,777,239 A | 10/1988 | Schoolnik et al. |
| 4,816,253 A | 3/1989 | Likhite |
| 5,262,177 A | 11/1993 | Brown et al. |
| 5,342,774 A | 8/1994 | Boon et al. |
| 5,681,570 A | 10/1997 | Yang et al. |
| 5,824,538 A | 10/1998 | Branstrom et al. |
| 5,830,702 A | 11/1998 | Portnoy et al. |
| 5,858,682 A | 1/1999 | Gruenwald et al. |
| 5,877,159 A | 3/1999 | Powell et al. |

(Continued)

FOREIGN PATENT DOCUMENTS

EP          0 902 086          3/1999

(Continued)

OTHER PUBLICATIONS

Chamberlain, R.S. et al. Expert Opinion on Pharmacotherapy, 1(4): 603-614, 2000.*

(Continued)

*Primary Examiner*—Alana M. Harris
*Assistant Examiner*—Anne L Holleran
(74) *Attorney, Agent, or Firm*—Mark S. Cohen; Pearl Cohen Zedek Latzer, LLP

(57) ABSTRACT

The present invention includes compositions, methods and kits for inducing an immune response to a tumor and for treating cancer with a *Listeria* vaccine strain expressing an antigen fused to a truncated LLO protein.

15 Claims, 15 Drawing Sheets

U.S. PATENT DOCUMENTS

| | | | |
|---|---|---|---|
| 6,015,567 | A | 1/2000 | Hudziak et al. |
| 6,017,705 | A | 1/2000 | Lurquin et al. |
| 6,051,237 | A | 4/2000 | Paterson |
| 6,099,848 | A | 8/2000 | Frankel et al. |
| 6,306,404 | B1 | 10/2001 | LaPosta et al. |
| 6,479,258 | B1 | 11/2002 | Short |
| 6,521,449 | B1 | 2/2003 | Polack et al. |
| 6,565,852 | B1 | 5/2003 | Paterson |
| 6,740,516 | B2 | 5/2004 | Savitzky et al. |
| 6,767,542 | B2 | 7/2004 | Paterson et al. |
| 7,135,188 | B2 * | 11/2006 | Paterson .................. 424/277.1 |
| 7,588,930 | B2 | 9/2009 | Paterson et al. |
| 2003/0028206 | A1 | 2/2003 | Shiber |
| 2003/0202985 | A1 | 10/2003 | Paterson |
| 2003/0220239 | A1 | 11/2003 | Simard et al. |
| 2004/0228877 | A1 | 11/2004 | Dubensky et al. |
| 2005/0118184 | A1 | 6/2005 | Paterson et al. |
| 2005/0129715 | A1 | 6/2005 | Paterson et al. |
| 2006/0051380 | A1 | 3/2006 | Schulick et al. |
| 2006/0093582 | A1 | 5/2006 | Paterson et al. |
| 2006/0104991 | A1 | 5/2006 | Paterson et al. |
| 2006/0121053 | A1 | 6/2006 | Sweeney et al. |
| 2006/0205067 | A1 | 9/2006 | Paterson et al. |
| 2006/0210540 | A1 | 9/2006 | Paterson et al. |
| 2006/0223835 | A1 | 10/2006 | Paterson et al. |

FOREIGN PATENT DOCUMENTS

| | | |
|---|---|---|
| WO | WO 92/20356 | 11/1992 |
| WO | WO 93/15212 | 8/1993 |
| WO | WO 94/17192 | 8/1994 |
| WO | WO 96/14087 | 5/1996 |
| WO | WO 96/34631 | 11/1996 |
| WO | WO 98/48026 | 10/1998 |
| WO | WO 99/06544 | 2/1999 |
| WO | WO 99/07861 | 2/1999 |
| WO | WO 99/10496 | 3/1999 |
| WO | WO 01/27295 | 3/2001 |
| WO | WO 01/72329 | 10/2001 |
| WO | WO 03/092600 | 11/2003 |
| WO | WO 2004/006837 | 1/2004 |

OTHER PUBLICATIONS

Bernhard, H. et al., Endocrine-Related Cancer 9: 33-44, 2002.*
Ezzel (J. Nih Res. 7: 46, 1995.*
Renard, V. et al. The Journal of Immunology, 171: 1588-1595, 2003.*
Paterson, Y., Immunologic Research, 27(2-3): 451-462, Jun. 2003.*
Knutson, K. L., et al. The Journal of Clinical Investigation, 107: 477-484, 2001.*
Mandal, et al, BBA, 2002, 1563: 7-17.
Kerksiek, et al, Current Opinion in Immunology, 1999 11:40-405.
Harty, et al, Current Opinion in Immunology, 1996, 8: 526-530.
Shen, et al, Current Opinion in Immunology, 1998, 10. 450-458.
Paterson, et al, Current Opinion in Immunology, 1996, 8:664-669.
Lara-Tejero, et al, Current Opinion in Immunology, 2004, 7: 45-50.
Gunn, Dissertaiton Abstracts International, 2001, 62/5B.2244 Abstract Only.
Beatly, Dissertation Abstracts Interntational, 2000, 61/10B:5224 Abstract Only.
Gunn et al, J. Immunology, 2001, 167: 6471-6479.
Hu, et al, J. Immunology, 204, 172: 1595-1601.
Burnham, Drug Discovery Today, Jan. 2003, 8/2:54-55.
Pan, et al, Cancer Research, 1999, 59: 5264-5269.
Lamikanra, et al, J Virology, Oct, 2001, 75/20:9654-9664.
Ikonomidis; et al, J. Exp. Med , Dec. 1994, 180: 2209-2218.
Radford, et al, Gene Therapy, 2002, 9: 1455-1463.
Radford, et al, Int. J. Cancer, 2003, 105: 811-819.
Gunn, et al, Trends in Microbiology, Apr. 2001, 9/4: 161-162.
Peng, et al, J. Immunology, 2004, 172: 6030-6038.
Barry, et al (1992) "Pathogenicity and immunogenicity of Listeria monocytogenes small-plaque mutants defective for intracellular growth and cell-to-cell spread."Infection and Immunity 60 (4): 1625-32.
Schafer, et al (1992) "Induction of a cellular immune response to a foreign antigen by a recombinant Listeria monocytogenes vaccine." J Immunology, 149(1) 53-59.
Bast, et al (1975) "Antitumor activity of bacterial infection. II. effect of Listeria monocytogenes on growth of a guinea pig hepatoma." J Natl. Cancer Inst., 54(3): 757-761.
Brasseur, et al (1992) "Human gene MAGE-1, which codes for a tumor-rejection antigen, is expressed by some breast tumors." Int. J Cancer 52(5):839-841.
Adams et al., 1992, "Cre-lox recombination in *Escherichia coli* cells Mechanistic differences from the in vitro reaction", J. Mol. Biol. 226:661-673.
Allision et al., 1997, "Cloning and characterization of a Prevotella melaninogenica hemolysin". Infect. Immun. 65(7):2765-71.
An et al., 1996, "A recombinant minigene vaccine containing a nonameric cytotoxic-T-Lymphocyte epitope confers limited protection against Listeria monocytogenes infection", Infect. Immun., vol. 64, No. 5, p. 1685-1693.
Anderson, 1998, "Human gene therapy ", Nature, Apr. 30; 392 (6679 Suppl):25-30.
Angelakopoulos et al., 2002, "Safety and shedding of an attenuated strain of Listeria monocytogenes with a deletion of actA/plcB in adult volunteers: a dose escalation study of oral inoculation" Infect Immun. 70(7):3592-601.
Attwood et al., "The Babel of Bioinformatics", Science, vol. 290, No. 5491: 471-473, 2000.
Awwad, 1989, "Cyclophosphamide-induced immunologically mediated regression of a cyclophosphamide-resistant murine tumor a consequence of eliminating precursor L3T4+ suppressor T-cells", Cancer Res., 49(7):1649-1654.
Bear, 1986, "Tumor-specific suppressor T-cells which inhibit the in vitro generation of cytolytic T-cells from immune and early tumor-bearing host spleens", Cancer Res., April; 46(4 Pt 1):1805-12.
Beattie IA, Swaminathan B. Ziegler HK, Cloning and charcterization of T-cell-reactive protein antogens from Listeria monocytogenes, infect. Immune. Sep. 1990, 58(9)2792-803.
Beaucage et al., "Deoxynucelotide phosphoramidites—a new class of key intermediates for deoxypolynucleotide synthesis", 1981, Tetra. Lett., 22:1859-1862.
Bernhard et al:. 2002, "Vaccination against the HER-2/neu oncogenic protein", Endocrine-Related Cancer, 9:33-44.
Bielecki et al., "Bacillus subtilis expressing a haemolysin gene from Lesteria monocytogenes can grow in mammalian cells", Nature 1990, 354:175-176.
Billington et al., 1997, "The Arcanobacterium (Actinomyces) pyogenes hemolysin, pyolysin, is a novel member of the thiol-activated cytolysin family", J. Bacteriol. Oct; 179(19):6100-6.
Bodmer et al., 1988, "Enhanced recognition of a modified peptide antigen by cytotoxic T cells specific for influenza nucleoprotein", Cell 52:253-258.
Boon et al., 2006, "Human T-cell responses against melanoma" Annu. Rev. Immunol. 24:175-208.
Bourquin et al., 2000, "Myelin oligodendrocyte glycoprotein-DNA vaccination induces antibody-mediated autoaggression in experimental autoimmune encephalomyelitis" Eur. J. Immunol. 30:3663-3671.
Bouwer HG, Barry RA, Hinrichs DJ, Acquired immunity to an intracellular pathogen: immunologic recognition of L. monocytogenes-infected cells, Immunol. Rev. Aug. 1997; 158:137-46.
Bouwer HG, Hinrichs DJ, Cytotoxic-T-lymphocyte responses to epitopes of listeriolysin O and p60 following infection with Listeria monocytogenes, Infect. Immune. Jul. 1996; 64(7):2515-22.
Boyer et al., 2005, "DNA prime Listeria boost induces a cellular immune response to SIV antigens in the rhesus macaque model that is capable of limited suppression of SIV239 viral replication", Virology, Mar. 1; 333(1):88-101.

Brockstedt et al., 2004, "Listeria-based cancer vaccines that segregate immunogenicity from toxicity", Proc. Natl. Acad. Sci. USA 101(38):13832-7.

Bron et al., 2004, "Identification of Lactobacillus plantarum genes that are induced in the gastrointestinal tract of mice", J. Bacteriol. September; 186(17):5721-9.

Brown et al., "Chemical synthesis and cloning of a tyrosine tRNA gene" 1979, Meth. Enzymol. 68:109-151.

Brown et al., 1988, "Site-specific integration in Saccharopolyspora erthraea and multisite integration in Streptomyces lividans of actinomycete plasmid pSE101", J. Bacteriology 170: 2287-2295.

Bruder D, Darji A, Gakamsky DM, Chakraborty T, Pecht I, Wehland J, Wehland J. Weiss S, Efficient induction of cytotoxic CD8+ T cells against exogenous proteins: establishment and characterization of a T cell line specific for the membrane protein ActA of Listeria monocytogenes, Eur. J. Immunol. Sep. 1998; 28(9):2630-9.

Bruhn et al., 2005, "Characterization of anti-self CD8 T-cell responses stimulated by recombinant Listeria monocytogenes expressing the melanoma antigen TRP-2", Vaccine, Jul. 21; 23(33):4263-72.

Brundage et al., 1993, "Expression and phosphorylation of the Listeria monocytogenes ActA protein in mammalian cells", Proc. Natl. Acad. Sci. USA 90:11890-11894.

Bubert et al., 1997, "The Listeria monocytogenes iap gene as an indicator gene for the study of PrfA-dependent regulation", Mol. Gen. Genet. Septemeber; 256(1):54-62.

Calendar et al., Poster presented at the ISOPOL Meeting 2001, http://64.233.169.104/search?q=cache:mA_uJpQsCrcJ:www.ma.uni-heidelberg.de/inst/imh/download/isopol.doc+Portnoy+Isopol+2001&hl=en&ct=clnk&cd=3&gl=us.

Camilli et al., 1993, "Daul roles of plcA in Listeria monocytogenes pathogenesis", Mol. Microbiol. 8:143-157.

Carbone, 1989, "Induction of ovalbumin-specific cytotoxic T cells by in vivo peptide immunization" J. Exp. Med. 169:603-612.

Carbone, 1990, "Class I-restricted processing and presentation of exogenous cell-associated antigen in vivo" J. Exp. Med. 171:377-387.

Catic A, Dietrich G, Gentschev I, Goebel W, Kaufmann SH, Hess J., Introduction of protein or DNA delivered via recombinant Salmonella typhimurium into the major histocompatibility complex class I presentation pathway of macrophages, Microbes Infect., Feb. 1999, 1(2):113-21.

Cenatiempo, "Prokaryotic gene expression in vitro: transcription-translation coupled systems." 1986, Biochimie 68:505-516.

Courvalin et al., 1995, "Gene transfer from bacteria to mammalian cells", C R Acad Sci III, December; 318(12):1207-12.

Cunto-Amesty et al., 2003, "Strategies in cancer vaccines development", Int. J. Parasitol. 33(5-6):597-613.

Dakappagari et al., 2000, "Prevention of mammary tumors with a chimeric HER-2 B-cell epitope peptide vaccine", Cancer Res. Jul. 15; 60(14):3782-9.

Darji A, Bruder D, Zur Lage S, Gerstel B, Chakraborty T, Wehland J, Weiss S, The role of the bacterial membrane protein ActA in immunity and protection against Listeria monocytogenes, J. Immunol. Sep. 1, 1998, 161(5):2414-20.

Darji A, Stockinger B, Wehland J, Chakraborty T, Weiss S, Antigen-specific T cell receptor antagonism by antigen-presenting cells treated with the hemolysin of Listeria monocytogenes: a noval type of immune escape, Eur. J. Immunol. Jul. 1997; 27(7):1696-703.

Darji A, Stockinger B, Wehland J, Chakraborty T, Weiss S, T-cell anergy induced by antigen presenting cells treated with the hemolysin of Listeria monocytogenes, Immunol. Lett. Jun. 1, 1997, 57(1-3):33-7.

Darji et al., 1995, "Hyperexpression of listeriolysin in the nonpathogenic species Listeria innocua and high yield purification", J. Biotechnol. Dec. 15; 43(3):205-12.

Darji et al., 1995, "Listeriolysin generates a route for the presentation of exogenous antigens by major histocompatibility complex class I", Eur. J. Immunol. October; 25(10):2967-71.

Darji et al., 1997, "Oral somatic transgene vaccination using attenuated S. typhimurium" Cell 91:765-775.

Darji et al., 1997, "TAP-dependent major histocompatibility complex class I presentation of soluble proteins using listeriolysin", Eur. J. Immunol. June; 27(6):1353-9.

Darji et al., 2003, "Induction of immune responses by attenuated isogenic mutant strains of Listeria monocytoge" Vaccine 1; 21 Suppl. 2:S102-9.

De Boer et al., "A division inhibitor and a topological specificity factor coded for by the minicell locus determine proper placement of the division septum in E. coli." 1989, Cell 56:641-649.

Decatur A.L. et al., "A Pest-Like Sequence in Listeriolysin O Essential for Listeria monocytogenes Pathogenicity", Science 2000, 290:992-995.

Dermime et al., 2004, "Vaccine and antibody-directed T cell tumour immunotherapy" Biochim Biophys Acta. 1704(1):11-35.

Deshpande et al., 1997, "Isolation of a contact-dependent haemolysin from Mycobacterium tuberculosis", J. Med. Microbiol. Mar.; 46(3):233-8.

Dietrich et al., 1998, "Delivery of antigen-encoding plasmid DNA into the cytosol of macrophages by attenuated suicide Listeria monocytogenes" Nature Biotechnology 15:181-185.

Dietrich et al., 2001, "From evil to good: a cytolysin in vaccine development", Trends Microbiol. January; 9(1):23-8.

Doling AM, Ballard JD, Shen H, Krishna KM, Ahmed R, Collier RJ, Starnbach MN, Cytotoxic T-lymphocyte epitopes fused to anthrax toxin induce protective antiviral immunity, Infect. Immun. Jul. 1999; 67(7):3290-6.

Dramsl et al., 1995, "Entry of Listeria monocytogenes into hepatocytes requires expression of inIB, a surface protein of the internalin multigene family", Mol. Microbiol. 16(2):251-61.

Dunn et al., 1991, "Selective radiation resistance of immunologically induced T cells as the basis for irradiation-induced T-cell-mediated regression of immunogenic tumor", J. Leukoc Biol. 49(4):388-396.

Ebert et al., 1990, "Selective immunosuppressive action of a factor produced by colon cancer cells", Cancer Res. 50(19):6158-6161.

Ezzel, 1995, "Cancer Vaccines: An Idea Whose Time Has Come?" J. NIH Res., 7:46-49.

Falk et al., 1991, "Identification of naturally processed viral nonapeptides allows their quantification in infected cells and suggests an allele-specific T cell epitope forecast" J. Exp. Med. 174(2):425-434.

Finn et al., 2003, "Cancer vaccines: between the idea and the reality" Nature Reviews Immunology 3:630-641.

Frankel et al., 1995, "Induction of cell-mediated immune responses to human immunodeficiency virus type 1 Gag protein by using Listeria monocytogenes as a live vaccine vector" J. Immunol. 155:4775-4782.

Frey, 1993, "Rat adenocarcinoma 13762 expresses tumor rejection antigens but tumor-bearing animals exhibit tumor-specific immunosuppression", Clin. Immunol. Immunopathol. 69(2):223-233.

Friedman et al., 2000, "Induction of human immunodeficiency virus (HIV)-specific CD8 T-cell responses by Listeria monocytogenes and a hyperattenuated Listeria strain engineered to express HIV antigens" J. Virology 74 9987-9993.

Fu et al., 1990, "Expansion of Immunoregulatory macrophages by granulocyte-macrophage colony-stimulating factor derived from a murine mammary tumor", Cancer Res. 50(2):227-234.

Fuji, 1987, "Significance of suppressor macrophages for immunosurveillance of tumor-bearing mice" J. Natl. Cancer Inst. 78(3):509-517.

Furukawa, 1993, "Nude mouse metastatic models of human stomach cancer constructed using orthotopic implantation of histologically intact tissue" Cancer Res. 53(5):1204-1208.

Galen et al., 2001, "Can a 'flawless' live vector vaccine strain be engineered?", Trends Microbiol. 9(8):372-6.

Garay-Malparticla HM, et al., "CaSPredictor: a new computer-based tool for caspase substrate prediction", Bioinformatics Jun. 2005; 21 Suppl. 1: i169-76.

Gentschev et al., "Salmonella Strain Secreting Active Listeriolysin Changes Its Intracellular Localization", Infect. Immun., 1995, 63:4202-4205.

Gentschev et al., 1996, "Development of antigen-delivery systems, based on the *Escherichia coli* hemolysin secreatiohn pathway" Gene 179:133-140.

Gilman et al., "Isolation of sigma-28-specific promoters from Bacillus subtilis DNA" 1984, Gene 32:11-20.

Gilmore et al., 1989, "A Bacillus cereus cytolytic determinant, cereolysin AB, which comprises the phospholipase C and sphingomyelinase genes: nucleotide sequenc and genetic linkage", J. Bacteriol. February; 171(2):744-53.

Glick, "Factors affecting the expression of foreign proteins in *Escherichia Coli*" 1987, J. Ind. Microbiol. 1:277-282.

Glomski et al., 2002, "The Listeria monocytogenes hemolysin has an acidic pH optimum to compartmentalize activity and pevent damage to infected host cells" J. Cell Biol. Mar. 18; 156(6):1029-38.

Goebel et al., 1993, "Listeria monocytogenes-a model system for studying the pathomechanisms of an intracellular microorganism", Zbl. Bakt. 278:334-347.

Gold L. et al., "Translational initiation in prokaryotes." 1981, Ann. Rev. Microbiol. 35:365-404.

Goossens et al., 1992, "Induction of protective CD8+ T lymphocytes by an attenuated Listeria monocytogenes actA mutant" Int. Immunol. December; 4(12):1413-8.

Goossens et al., 1995, "Attenuated Listeria monocytogenes as a live vector for induction of CD8+ T cells in vivo: a study with the nucleoprotein of the lymphocytic choriomeningitis virus", Int. Immunol. May; 7(5):797-805.

Gottesman, "Bacterial regulation: global regulatory networks." 1984, Ann.Rev. Genet. 18:415-442.

Gregory et al., 1997, "Internalin B promotes the replication of Listeria monocytogenes in mouse hepatocytes" Infect. Immun. 65(12):5137-41.

Gunn et al., 2002, "Recombinant Intra-cellular Bacteria as Carriers for Tumor Antigens", In Vaccine Delivery Strategies, Chapter 14, Eds. Guido Dietrich and Werner Goebel, Horizon Scientific Press, UK.

Guzman Carlos A et al.: "Attenuated Listeria monocytogenes carrier strains can deliver an HIV-1 gp120 T helper epitope to MHC class II-restricted human CD4+ T cells", European Journal of Immunology, vol. 28, No. 6, Jun. 1998, pp. 1807-1814.

Harty JT, Pamer EG, CD8 T lymphocytes specific for the secreted p60 antigen protect against Listeria monocytogenes infection, J. Immunol. May 1, 1995; 154(9):4642-50.

Hassan et al., 2004, "Mesothelin: a new target for immunotherapy" Clin. Cancer Res. 10(12 Pt 1):3937-42.

Hauf et al., 1997, "Listeria monocytogenes infection of P388D1 macrophages results in a biphasic NF-kappaB (RelA/p50) activation induced by lipoteichoic acid and Bacterial phospholipases and mediated by IkappaBalpha and IkappaBbeta degradation", Proc. Natl. Acad. Sci. U.S.A. Aug. 19; 94(17):9394-9.

Hess et al., 1995, "Listeria monocytogenes p60 supports host cell invasion by and in vivo survival of attenuated Salmonella typhimurium" Infect. Immun. May; 63(5):2047-53.

Hess et al., 1996, "Salmonella typhimurium aroA- infection in gene-targeted immunodeficient mice: major role of CD4+ TCR-alpha beta cells and IFN-gamma in bacterial clearance independent of intracellular location" J. Immunol. May 1; 156(9):3321-6.

Hess et al., 1996, "Superior efficacy of secreted over somatic antigen display in recombinant Salmonella vaccine induced protection against listeriosis" Proc. Nat. Acad. Sci. 93:1458-1463.

Hess et al., 1997, "Protection against murine listeriosis by an attenuated recombinant Salmonella typhimurium vaccine strain that secretes the naturally somatic antigen superoxide dismutase", Infect. Immun. April; 65(4):1286-92.

Hess J, et al, "Mycobacterium bovis Bacille Calmette-Guerin strains secreting listeriolysin of Listeria monocytogenes", Proc. Natl. Acad. Sci. U.S.A. 1998 Apr. 28; 95(9):5299-304.

Hess J., Kaufmann SH, Abstract, Live antigen carriers as tools for improved anti-tuberculosis vaccines, FEMS Immunol. Med. Microbiol. Feb. 1999; 23(2):165-73.

Higgins DE, Shastri N, Portnoy DA, Abstract, Delivery of protein to the cytosol of macrophages using *Escherichia coli* K-12, Mol. Microbiol. Mar. 31, 1991(6):1631-41.

Higgins et al., 1998, "Bacterial delivery of DNA evolves" Nat. Biotechnol. February; 16(2):138-9.

Hiltbold EM, Safley SA, Ziegler HK, The presentation of class I and class II epitopes of listeriolysin 0 is regulated by intracellular localization and by intracelluar spread of Listeria monocytogenes, J. Immunol. Aug. 1, 1996; 157(3):1163-75.

Hiltbold EM, Ziegler HK, Mechanisms of processing and presentation of the antigens of Listeria monocytogenes, Infect. Agents Dis. Oct. 1993; 2(5):314-23.

Hodgson, 2000, "Generalized transduction of serotype 1/2 and serotype 4b strains of Listeria monocytogenes", Mol. Microbiol. 35(2):312-23.

Huang et al., 1994, "Role of bone marrow-derived cells in presenting MHC class I-restricted tumor antigens" Science 264:961-965.

Hussain et al., 2004, "CD4+CD25+ regulatory T cells that secrete TGFbeta and IL-10 are preferentially induced by a vaccine vector" J. Immunother September-October; 27(5):339-46.

Ikonomidis et al., 1994, Abstract E-90, Abstracts, 94th General Meeting of the American society for Microbiology, May 23-27.

International Search Report of Application No. PCT/US07/06292 issued on Jun. 17, 2008.

Jensen et al., 1997, "Recombinant Listeria monocytogenes as a live vaccine vehicle and a probe for studying-cell-mediated immunity" Immunological Review 158:147-157.

Jensen, 1997, "Recombinant Listeria monocytogenes vaccination eliminates papillomavirus-induced tumors and prevents papilloma formation from viral DNA", J. Virol. 71(11):8467-8474.

Jones et al., 1994, "Characterization of Listeria monocytogenes pathogenesis in a strain expressing perfingolysin O in place of listeriolysin O", Infect. Immun. 62:5608-5613.

Kaufman S.H. et al., "Impact of intracellular location of and antigen display by intracellular bacteria:implications for vaccine development", J. Immunol. Lett. 1999, 65(1-2):81-84.

Kocks et al., 1992, "L monocytogenes-induced act in assembly requires the actA gene product", Cell, vol. 68, No. 3, p. 521-531.

Kovacsovics-Bankowski et al., 1993, "Efficient major histocompatibility complex class I peresentation of exogenous antigen upon phagocytosis by macrophages", Proc. Natl. Acad. Sci. USA 90:4942-4946.

Knutson K. L. et al., "Immunization with a HER-2/neu helper peptide vaccine generates HER-2/neu CD8 T-cell immunity in cancer patients." The Journal of Clinical Investegation, 107:477-484, 2001.

Kyte J. and Dootlittle RF, "A simple method for displaying the hydropathic character of a protein" J. Mol. Biol. 157, 105, 1982.

Lampson et al., 1993, "Exploiting the lacZ reporter gene for quantitative analysis of disseminated tumor growth within the brain: use of the lacZ gene product as a tumor antigen, for evaluation of antigenic modulation, and to facilitate image analysis of tumor growth in situ", Cancer Research 53:176-182.

Lasa et al., 1997, "Identification of two regions in the N-terminal domain of ActA involved in the actin comet tail formation by Listeria monocytogenes" EMBO 16(7):1531-40.

Lauer et al., 2002, "Construction, characterization, and use of two Listeria monocytogenes site-specific phage integration vectors" J. Bacteriology 184:4177-4186.

Lauer et al., "Characterization of the Attachment Site of Bacteriophage U153 within the Listeria monocytogenes comK Gene" ASM Meeting, Abstract 1999.

Lauer et al., "Systematic mutational analysis of the amino-terminal domain of the Listeria monocytogenes ActA protein reveals novel functions in actin-based motility" Molecular Microbiology 42(5):1163-1177, 2001.

Leao et al., 1995, "A species-specific nucleotide sequence of Mycobacterium tuberculosis encodes a protein that exhibts hemolytic activity when expressed in *Escherichia coli*" Infect. Immun. November; 63(11):4301-6.

Lebrun M. et al., Aug. 1996, "Internallan must be on the Bacterial Surface to mediate Entry of Listeria monocytogenes into Epithelial Cells", Molecullar Microbiology 21:579-592.

Lee et al., 1991, "Construction of single-copy integration vectors for Staphylococcus aureus", Gene 103:101-5.

Lee KD, Oh YK, Portnoy DA, Swanson JA, Delivery of macromolecules into cytosol using liposomes containig hemolysin from Listeria monocytogenes, J. Biol. Chem., Mar. 29, 1996 271(13):7249-52.

Lehner et al., 1996, "Processing and delivery of peptides presented by MHC class I molecules", Curr. Opin. Immunol. 8(1):59-67.

Lejeune, 1994, "Nitric oxide involvement in tumor-induced immunosuppression" J. Immunol. 152(10):5077-5083.

Liau et al., 2002, "Tumor immunity within the central nervous system stimulated by recombinant Listeria monocytogenes vaccination", Cancer Res., 62(8):2287-93.

Lin et al., "Treatment of Established Tumors with a Novel Vaccine that Enhances Major Histocompatibility Class II Presentation of Tumor Antigen", Cancer Res. 1996, 56:21-26.

Lin et al., 2002, "Oral vaccination with recombinant Listeria monocytogenes expressing human papillomavirus type 16 E7 can cause tumor growth in mice to regress" Int. J. Cancer, Dec. 20; 102(6):629-37.

Lingnau et al., 1995, "Expression of the Listeria monocytogenes EGD inlA and inlB genes, whose products mediate bacterial entry into tissue culture cell lines, by PrfA-dependent and independent mechanisms" Infect. Immun. October; 63(10):3896-903.

Lipford GB, Wagner H, Heeg K, Vaccination with immunodominant peptides encapsulated in Quil A-containing liposomes induces peptide-specific primary CD8+ cytotoxic T cells, Vaccine Jan. 1994; 12(1):73-80.

Loeffler et al., 2006, "Comparison of different live vaccine strategies in vivo for delivery of protein antigen or antigen-encoding DNA and mRNA by virulence-attenuated Listeria monocytogenes" Infect. Immun. July; 74(7):3946-57.

Loessner et al., 1995, "Heterogeneous endolysins in Listeria monocytogenes bacteriophages: a new class of enzymes and evidence for conserved holin genes within the siphoviral lysis cassettes", Mol. Microbiol. June; 16(6):1231-41.

Loessner et al., 2000, "Complete nucleotide sequence, molecular analysis and genome structure of bacteriophage A118 of Listeria monocytogenes: implications for phage evolution", Molecular Microbiology 35(2):324-40.

Makela et al., Hand book of Experimental Immunology vol. 1, Chapter 3—"Haptens and carriers", pp. 3.1-3.13; 1987.

Manjili et al., 2003, "HSP110-HER2/neu chaperone complex vaccine induces protective immunity against spontaneous mammary tumors in HER-2/neu trangenic mice" J. Immunol. Oct. 15; 171(8):4054-61.

Marquis et al., 1997, "Proteolytic pathways of activation and degradation of a bacterial phospholipase C during intracellular infection by Listeria monocytogenes" J. Cell Biol. 137:1381-1392.

Martin et al., 1986, "Nucleotide sequence of the tetM tetracycline resistance determinant of the streptococcal conjugative shuttle transposon Tn1545", Nucleic Acid Res. 14:7047-7058.

Marx et al., 2002, "Broad-host-range cre-lox system for antibiotic marker recycling in gramnegativ bacteria" Biotechniques, November; 33(5):1062-7.

Mazzaccaro RJ, Gedde M, Jensen ER, Van Santen HM, Polegh HL, Rock KL, Bloom BR, Major histocompatibility class I presentation of soluble antigen facilitated by Mycobacterium tuberculosis infection, Proc. Natl. Acad. Sci. U.S.A. Oct. 15, 1996; 93(21):11786-91.

McLaughlan et al., 1998, "Molecular characterization of an autolytic amidase of Listeria monocytogenes EGD", Microbiology, May; 144(Pt 5):1359-67.

Mengaud et al., 1988, "Expression in *Escherichia coli* and sequence analysis of the listeriolysin O determinant of listeria monocytogenes", Infect. Immun., vol. 56, No. 4, 766-772.

Merrifiled et al., "Solid phase peptide synthesis. 1. The synthesis of a tetrapeptide" J. Am. Chem. Soc., 85:2149-2156 (1963).

Mikayama et al., Molecular cloning and functional expression of a cDNA encoding gycosylation-inhibiting factor, Nov. 1993, Pro Natl. Acad. Sci., USA, vol. 90:10056-10060.

Miller et al., "Targeted vectors for gene therapy" 1995, FASEB J., 9:190-199.

Mlynarova et al., 2002, "The promiscuity of heterospecific lox sites increases dramatically in the presence of palindromic DNA", Gene, Aug. 21; 296(1-2):129-37.

Mollet et al., 1993, "Directed genomic integratoin, gene replacement, and integrative gene expression in Streptococcus thermophilus" J. Bacteriology 175:4315-4324.

Moriishi et al., 1998, "Sequence analysis of the actA gene of Listeria monocytogenes isolated from human", Microbiol. Immunol., vol. 42, No. 2, p. 129-132.

Narang et al., "Improved phosphotriester method for the synthesis of gene fragments" 1979, Meth. Enzymol. 68:90-99.

Nielsen PE, "Peptide nucleic acids as therapeutic agents" Curr. Opin. Struct Biol. 9:353-57.

Ngo et al., 1994, The Protein Folding Problem and Tertiary Structure Prediction, pp. 492-495.

Ochsenbein et al., 1999, "A comparison of T cell memory against the same antigen induced by virus versus intracellular bacteria" Proc. Natl. Acad Sci U.S.A. Aug. 3; 96(16):9293-8.

Oscarsson et al., 1996, "Induction of haemolytic activity in *Escherichia coli* by the slyA gene product" Mol. Microbiol. April; 20(1):191-9.

Paglia et al., 1997, "The defined attenuated Listeria monocytogenes delta mp12 mutant is an effective oral vaccine carrier to trigger a long-lasting immune response against a mouse fibrosarcoma" Eur. J. Immunol. 27:1570-1575.

Palmeros et al., 2000, "A family of removable cassettes designed to obtain antibiotic-resistance-free genomic modifications of *Escherichia coli* and other bacteria" Gene, Apr. 18; 247(1-2):255-64.

Pan et al., "Regression of Established Tumors in Mice Mediated by the Oral Administration of a Recombinant Listeria monocytogenes Vaccine", Cancer Res., 1995, 55:4776-4779.

Pan et al., 1995, "A recombinant Listeria monocytogenes vaccine expressing a model tumour antigen protects mice against lethal tumour cell challenge and causes regression of established tumours" Nature Med. 1:471-477.

Parida et al., 1998, "Internalin B is essential for adhesion and mediates the invasion of Listeria monocytogenes into human endothelial cells" Mol. Microbiol. April; 28(1):81-93.

Paterson, "Rational approaches to immune regulation", Immunologic Research, 2003; 27/2-3:451-462.

Paul et al., 1989, "Fundamental Immunology", Second Edition, Raven Press, 987-988.

Penichet et al., 2001, "Antibody-cytokine fusion proteins for the therapy of cancer" J. Immunological Methods 248:91-101.

Peters et al., 2003, "Tailoring host immune responses to Listeria by manipulation of virulence genes-the interface between innate and acquired immunity" FEMS Immunol. Med. Microbiol. Apr. 1; 35(3):243-53.

Pfeifer et al., 1993, "Phagocytic processing of bacterial antigens for class I MHC presentation to T cells" Nature, Jan. 28; 361(6410):359-62.

Pupa et al., 2001, "Prevention of spontaneous neu-expressing mammary tumor development in mice transgenic for rat proto-neu by DNA vaccination" Gene Ther. January; 8(1):75-9.

Quenee et al., 2005, "Combined sacB-based negative selection and cre-lox antibiotic marker recycling for efficient gene deletion in pseudomonas aeruginosa", Biotechniques, January; 38(1):63-7.

Raveneau et al., 1992, "Reduced virulence of a Listeria monocytogenes phospholipase-deficient mutant obtained by transposon insertion into the zinc metalloproteas gene" Infect. Immune., 60:916-921.

Realini et al., "Proposed roles in protein-protein association and presentation of peptides by MHC Class I receptors", FEBS Lett., 1994, 348:109-113.

Rechsteiner and Rogers, "PEST sequences and regulation by proteolysis", TIBS, 1996, 21:267-271.

Reiter et al., 1989, "Transfer RNA genes frequently serve as integration sites for porkaryotic genetic elements", Nucleic Acids Research 17(5):1907-14.

Renard V. et al., "HER-2 DNA and protein vaccines containing potent Th cell epitopes induce distinct protective and therapeutic antitumor responses in HER-2 transgenic mice", The Journal of Immunology, 171(3):1588-1595, 2003.

Repique, 1992, "Immunosuppression derived from human B-lymphoblastoid and melanoma cell lines" Cancer Invest. 10(3):201-208.

Roden et al., 2004, "Vaccination to prevent and treat cervical cancer", Hum. Pathol. 35(8):971-82.

Russmann et al., 1998, "Delivery of epitopes by the Salmonella type III secretion system for vaccine system for vaccine development", Science, Jul. 24; 281(5376):565-8.

Safley et al., "Role of listeriolysin-O (LLO) in the T lymphocyte response to infection with Listeria monocytogenes. Identification of T cell epitopes of LLO" J. Immunology 146(10):3604-3616; May 1991.

Scheirlinck et al., 1989, "Integration and expression of alpha-amylase and endoglucanase genes in the Lactobacillus plantarum chromosome", Appl. Environ Microbial. 55(9):2130-7.

Schmidt et al., 1995, "Molecular Analysis of the Plasmid-Encoded Hemolysin of *Escherichia coli* O157:H7 Strain EDL 933", Infection and Immunity, 63(3):1055-1061.

Schnupf et al., "Phosphorylation, ubiquitination and degradation of listeriolysic O in mammalian cells: role of the PEST-like sequence" Cellular microbiology 8(2):353-364, 2006.

Scortti et al., 2007, "The PrfA virulence regulon", Microbes Infect. August; 9(10)1196-207.

Sewell D. A., Regression of HPV-Positive Tumors Treated with a New Listeria monocytogenes Vaccine Arch Otolaryngo., Head Neck Surg., Jan. 2004, vol. 130, pp. 92-97.

Sewell et al., "Recombinant Listeria vaccines containing PEST sequences are potent immune adjuvants for the tumor-associated antigen human papillomavirus-16 E7", Cancer Research 64(24):8821-8825, 2004.

Shen et al., 1995, "Recombinant Listeria monocytogenes as a live vaccine vehicle for the induction of protective anti-viral cell-mediated immunity" Proc. Nat'l Acad Sci U.S.A., 92(9):3987-91.

Shen et al., 1998, "Compartmentalization of bacterial antigens: diffrential effects on priming of CD8 T cells and protective immunity" Cell., Feb. 20; 92(4):535-45.

Shetron-Rama et al., 2002, "Intracellular induction of Listeria monocytogenes actA expression" Infect. Immun. 70:1087-1096.

Shimizu et al., 1994, "Effects of CD4+ and CD8+ T cells in tumor-bearing mice on antibody production" Cancer Immunol. Immunother 38(4):272-276.

Singh, R. Fusion to Listeriolysin O and Delivery by Listeria monocytogenes Enhances the Immunogenicity of HER-2/neu and Reveals Subdominant Epitope in the FVB/N Mouse, J. Immunology, Sep. 15, 2005, vol. 175, pp. 3663-3673.

Sirard et al., 1997, "Intrtracytoplasmic delivery of Lidteriolysin O by vaccinal strain of *Bacillus anthracis* induces CD8-mediated protection against listeria monocytogenes", J. Immunology, vol. 159, p. 4435-4443.

Skoble J. et al., Aug. 7, 2000, "Three Regions within ActA Promote Atp2/3 Complex-mediated Actin Nucleation and Listeria monocytogenes Motility", The Journal of cell Biology 150(3):527-537.

Skolnick et al., Form genes to protein structure and function: novel applications of computational approaches in the genomic era, Jan. 2000, Trends in Biotech., 18(1):34-39.

Slifka et al., 1996, "Antiviral cytotoxic T-cell memory by vaccination with recombinant Listeria monocytogenes" J. Virol. 70(5):2902-10.

Smith et al., 1995, "The two distinct phospholipases C of Listeria monocytogenes have overlapping roles in escape from a vacuole and cell-to-cell spread", Infect. Immun. 63:4231-4237.

Smith G.A. et al., Sep. 1995, "Asymmetric Distribution of the Listeria monocytogenes ActA Protein is Required and Sufficient to Direct Actin-Based Motility", Molecular Microbiology 17:945-951.

Souders et al., 2006, "In vivo bactofection: listeriacan function as a DNA-cancer vaccine" DNA Cell Biol. March; 25(3):142-51.

Stahl et al., 1984, "Replacement of the *Bacillus subtilisin* structural gene with an in vitro-derived deletion mutation" J. Bacteriol. 158:411-418.

Starks et al., 2004, "Listeria monocytogenes as a vaccine vector: virulence attenuation or existing antivector immunity does not diminish therapeutic efficacy", J. Immunology 173:420-427.

Stitz et al., 1990, "Characterization and immunological properties of influenza A virus nucleoprotein (NP): cell-associated NP isolated from infected cells or viral NP expressed by vaccinia recombinant virus do not confer protection" J. Gen. Virol., 71(Pt 5):1169-1179.

Strungnell et al., 1990, "Stable expression of forgein antigens from the chromosome of Salmonella typhimurium vaccine strains" Gene 88:57-63.

Stryer et al., "Levels of structure in protein architecture" Biochemistry, Third Edition, W H Freeman Company, New York, pp. 31-33, 1998.

Sun et al., 1990, "Isolation of Listeria monocytogenes small-plaque mutants defective for intracellular growth and cell-to-cell speard" Infect. Immun. 58:3770-3778.

Szalay G, Hess J, Kaufmann SH, Presentation of Listeria monocytogenes antigenes by major histocompatibility complex class I molecules to CD8 cytotoxic T lymphocytes independent of listeriolysin secretion and virulence, Eur. J. Immunol. Jul. 1994; 24(7):1471-7.

Tanabe et al., "Induction of Protective T Cells against Listeria monocytogenes in Mice by Immunization with a Listeriolysin O-Negative Avirulent Strain of Bacteria and Liposome-Encapsulated Listeriolysin O", Infect. Immun., 1999, 67(2):568-575.

Teitelbaum R, Cammer M, Maitland ML, Freitag NE, Condeelis J., Bloom BR, Mycobacterial infection of macrophages results in membrane-permeable phagosomes, Proc. Natl. Acad. Sci. U.S.A. Dec. 21, 1999, 96(26):15190-5.

Tilney et al., 1989, "Actin filaments and the growth, momvement, and speard of the intracellular bacterial parasite, Listeria monocytogenes" J. Cell Biol., October; 109(4 Pt 1):1597-608.

Ulmanen et al., "Transcription and translation of foreign genes in Bacillus Subtilis by the aid of a secretion vector" 1985, J. Bacteriol. 162:176-182.

Vasil et al., 1982, "Cloning of a phosphate-regulated hemolysin gene (phospholipase C) from Pseudomonas aeruginosa" J. Bacteriol. October; 152(1):431-40.

Vazquez MA, Sicher SC, Proctor ML, Crowley JC, Lu CY, Differential regulation of Ia expression and antigen presentation by listeriolysin-producing versus non-producing strains of Listeria monocytogenes, J. Leukoc Biol. May 1996; 59(5):683-90.

Vazquez-Boland et al., 1992, "Nucleotide sequence of the lecithinase operon of Listeria monocytogenes and possible role of lecithinase in cell-to-cell spread" Infect. Immun. 60:219-230.

Verch et al., 2004, "Listeria monocytogenes-based antibiotic resistance gene-free antigen delivery system applicable to other bacterial vectors and DNA vaccines" Infect. Immun. November; 72(11):6418-25.

Verma et al., 1995, "Delivery of class I and class II MHC-restricted T-cell epitopes of listeriolysin of listeria monocytogenes by attenuated salmonella", Vacine, vol. 13, No. 2, p. 142-150.

Villanueva MS, Sijts AJ, Pamer EG, Listeriolysin is processed efficiently into an MHC class I-assosiated epitope in Listeria monocytogenes-infected cells, J. Immunol. Dec. 1, 1995; 155(11):5227-33.

Vines A. et al., "Identfication and characterization of nucleotide sequence difference in three virulence-associate genes of listeria monocytogenes strains representing clinically important serotypes", Current Microbiology, May 1998, vol. 36, No. 5, pp. 309-318.

Walker et al., 1994, "Tumor growth Alters T cell and macrophage production of and responsiveness to granulocyte-macrophage colony-stimulating factor: partial dysregulation through interleukin-10" Cell Immunol. 154(1):342-357.

Ward et al., "Construction and characterisation of a series of multicopy promoter-probe plasmid vectors for Streptomyces using the aminoglycoside phosphotransferase gene from Tn5 as indicator" 1986, Mol. Gen. Genet. 203:468-478.

Watson et al., 1991, "Splenic macrophages from tumor-bearing mice co-expressing MAC-1 and MAC-2 antigen exert immunoregulatory functions via two distinct mechanisms" J. Leukoc Biol. 49(2):126-138.

Wei et al., 2005, "Listeria monocytogenes phosphatidylinositol-specific phospholipase C has evolved for virulence by greatly reduced activity on GPI anchors" Proc. Natl. Acad. Sci. U.S.A. 102:12927-12931.

Weidt et al., 1994, "CD8+ T lymphocyte-mediated antiviral immunity in mice as a result of injection of recombinant viral proteins", J. Immunol. Sep. 15; 153(6):2554-61.

Weiskirch LM, Paterson Y: "Listeria monocytogenes: a potent vaccine vector for neoplastic and infectious disease" Immunol. Rev., vol. 158, Aug. 1997, p. 159-169.

Welch M.D. et al., Jul. 3, 1998, "Interaction of Human Arp2/3 Complex and the Listeria monocytogenes ActA Protein in Actin Filament Nucleation" Science 281:105-108; pa-998020.

Wilson RL, White DW, Harty JT, Transient expression of bacterial gene fragments in eukaryotic cells: implications for CD8(+) T cell epitope analaysis, J. Immunol. Methods, Feb. 3, 2000; 234 (1-2):137-47.

Wirth et al., 1986, "Highly efficient protoplast transformation system for Streptococcus faecalis and a new *Escherichia coli*-S faecalis shuttle vector", J. Bacteriol. 165(3):831-6.

Wu et al., "Engineering an intracellular pathway for major histrocompatibility complex class II presentation of antigens", Proc. Natl. Acad Sci. USA, 1995, 92:11671-5.

Young et al., 1992, "Tumor-derived cytokines induce bone marrow suppressor cells that mediate immunosuppression through transforming growth factor beta", Cancer Immunol. Immunother. 35(1):14-18.

Young et al., 1995, "Holins: form and function in bacteriophage lysis" FEMS Microbiol Rev., August; 17 (1-2):191-205.

Zhang et al., 1993, "Functional replacement of the hemolysin a transport signal by a different primary sequence" Proc. Natl. Acad. Sci. U.S.A May 1; 90(9):4211-5.

Zwickey HL, Potter TA, Antigen secreted from noncytosolic Listeria monocytogenes is processed by the classical MHC class I processing pathway, J. Immunol. Jun. 1, 1999; 162(11):6341-50.

Zwickey HL, Potter TA, "Peptide epitopes from noncytosolic Listeria monocytogenes can be presented by major histocompatibility complex class I molecules", Infect. Immun. May 1996; 64(5):1870-2.

Clark et al., "Clinical use of streptolysin-O to facilitate antisense oligodeoxyribonucleotide delivery for purging autografts in chronic myeloid leukaemia", Bone Marrow Transplantation, vol. 23, No. 12, 1999, pp. 1303/1308.

Ikonomidis et al., "Influenze-specific immunity induced by recombinant Listeria monoctogenese vaccines", Vaccine, vol. 15, No. 4, 1997, pp. 433-440.

Rogers et al., "Amino acid sequences common to rapidly degraded proteins: The pest hypothesis", Science, vol. 234, 1986, pp. 364-368.

Barry, "Pathogenicity and Immunogenicity of Listeria monocytogenes Small-plaque mutants defective for Intrac", Infection and Immunity, Apr. 1992, vol. 60, No. 4, pp. 1625-1632.

Dustoor, "Antitumor activity of Listeria monocytogenes on a Guinea Pig Fibrosarcoma", Infection and Immunity, Jan. 1979, vol. 23, No. 1, pp. 54-60.

Ikonomidis, "Delivery of a Viral Antigen to the Class I Processing and Presentation Pathway by Listeria monocytogenes", J. Exp. Med., Dec. 1994, vol. 180, pp. 2209-2218.

* cited by examiner

METHODS AND COMPOSITIONS FOR IMMUNOTHERAPY OF CANCER

CROSS-REFERENCE TO RELATED APPLICATIONS

This application is a continuation-in-part of co-pending U.S. application Ser. No. 10/441,851, filed May 20, 2003, now U.S. Pat. No. 7,135,188 which is a continuation of U.S. application Ser. No. 09/535,212, filed Mar. 27, 2000, now issued as U.S. Pat. No. 6,565,852, which is a continuation-in-part of U.S. application Ser. No. 08/336,372, filed Nov. 8, 1994, now issued as U.S. Pat. No. 6,051,237 all of which are hereby incorporated by reference in their entirety herein.

STATEMENT REGARDING FEDERALLY SPONSORED RESEARCH OR DEVELOPMENT

This invention was supported in part by funds from the U.S. government (National Institutes of Health Grant No. NIH CA72108 and W81XWH-04-1-0338) and the U.S. government may therefore have certain rights in the invention.

BACKGROUND OF THE INVENTION

Stimulation of an immune response is dependent upon the presence of antigens recognized as foreign by the host immune system. The discovery of the existence of tumor associated antigens has now raised the possibility of using a host's immune system to intervene in tumor growth. Various mechanisms of harnessing both the humoral and cellular arms of the immune system are currently being explored for cancer immunotherapy.

Elements of the cellular immune response are capable of specifically recognizing and destroying tumor cells. The isolation of cytotoxic T cells (CTL) from tumor-infiltrating cell populations or from peripheral blood suggests that such cells play an important role in natural immune defenses against cancer (Cheever et al., Annals N.Y. Acad. Sci. 1993 690:101-112). CD8+ T cells (TCD8+) in particular, which recognize Class I molecules of the major histocompatibility complex (MHC)-bearing peptides of 8 to 10 residues derived from proteins located in the cytosols, are believed to play an important role in this response. There are now numerous examples of both mouse and human TCD8+ that specifically recognize tumor cells and have therapeutic activity after adoptive transfer, in some cases inducing complete remission. However, despite the potential for T cells to eradicate tumors, it is obvious from the progressive growth of most cancers that many tumors escape recognition by TCD8+ in vivo. The induction of sufficient T cells in vivo has been difficult. Though a variety of tumors have been found to be immunogenic, stimulation of an effective anti-tumor immune response has been difficult to demonstrate.

One explanation for this phenomena is that tumors may be capable of delivering antigen-specific signals to T cells, but not the co-stimulatory signals necessary for full activation of T cells. Co-stimulation of T cells occurs when a surface molecule, B7, on the presenting cells interacts with a T cell molecule known as CD28. It has been observed that T cells receiving the antigen-specific signal (but not B7) become unresponsive. Many tumor cells do not carry the B7 protein, therefore B7 has been added to cancer cells (Travis, J., Science 1993 259, 310-311). It has been demonstrated that expression of the co-stimulatory ligand B7 on melanoma cells induced the rejection of a murine melanoma in vivo (Townsend, S. E. and Allison, J. P., Science 1993, 259, 368-370). This rejection was found to be mediated by CD8+ T cells; CD4+ T cells were not required. These results suggest that B7 expression may render tumor cells capable of effective antigen presentation, resulting in their eradication in vivo.

The effects of localized secretion of cytokines on tumor progression has also been studied. Secretion of low levels of interleukin-2 (IL-2) in a mouse fibrosarcoma cell line transfected with the human IL-2 gene introduced via a retroviral vector was found to abrogate the tumorigenicity of these cells and induce a long lasting protective immune response against a subsequent challenge with a tumorigenic dose of parent cells (Gansbacher et al., J. Exp. Med. 1990, 172, 1217-1224). In another study, cells from a spontaneously arising murine renal cell tumor were engineered to secrete large doses of interleukin-4 (IL-4) locally (Golumbek et al., Science 1991, 254, 713-716). Animals injected with the tumor cells rejected the IL-4-transfected tumors in a predominantly T cell-independent manner. However, these animals developed a T cell-dependent systemic immunity to the parental tumor. The systemic immunity was tumor-specific and mediated by CD8+ T cells. These experiments suggest that it may be possible to cure parental tumors by generating a systemic immune response by the injection of genetically engineered tumor cells.

There is also evidence to suggest that some tumor cells express low levels of MHC class I molecules in vivo and in vitro. Intracellular antigens must be processed before presentation to CD8+ T cells by major histocompatibility complex (MHC) class I molecules. The antigen processing efficiency of 26 different human tumor lines has been studied (Restifo et al., J. of Exp. Med. 1993, 177, 265-272). Three different cell lines, all human small cell lung carcinomas, consistently failed to process endogenously synthesized proteins for presentation to the T cells. Pulse-chase experiments demonstrated that MHC class I molecules were not transported by these cells lines from the endoplasmic reticulum to the cell surface. Northern blot analysis demonstrated that these cells contained little or no mRNA encoding MHC-encoded proteasomes and transporter genes. Treatment with interferon γ enhanced expression of these mRNAs and reversed the observed functional and biochemical deficits. Thus, potential therapeutic applications which include enhancing antigen processing at the level of transcription of MHC-encoded proteasome and transporter genes was suggested.

Immunizing patients with recombinant BCG (bacille Calmette-Gurin) or *Salmonella* bacteria carrying a gene coding for an antigenic peptide has also been suggested as an oral tumor immunotherapy (Boon et al. Annu. Rev. Immunol. 1994, 12, 337-65). Orally administered live attenuated *Salmonella* recombinant vaccine, which expressed the full length *P. berghei* circumsporozite antigen, has been shown to protect mice against malaria. This immune response was mediated by the induction of CD8+ T cells (Aggarwal et al., J. of Exp. Med. 1990, 172, 1083-1090). It is suggested that live attenuated *Salmonella* recombinants may be useful in the study of other diseases where CTL-mediated immunity may be important. However, no other experiments were reported. BCG has also been implicated as a novel live-vaccine vehicle which may prove useful in stimulating both humoral and cellular immune response to a wide variety of viral, bacterial and protozoal antigens (Stover et al., Nature 1991, 351, 456-460).

It has now been found that the immune response to an antigen, and in particular a tumor associated antigen, can be induced by the administration of a vaccine comprising a listeriolysin fusion protein comprising a tumor associated antigen or a recombinant form of the intracellular bacterium *Listeria monocytogenes* which expresses a tumor associated antigen or fragment thereof. The recombinant form of *Listeria monocytogenes* can express the tumor associated antigen alone or as a listeriolysin fusion protein which comprises the tumor associated antigen. In one embodiment, one or more vectors comprising recombinant *Listeria monocytogenes* each expressing a different tumor associated antigen or fusion protein thereof, can be used in a vaccine to stimulate an immune response. In this embodiment, it is preferred that the expressed tumor associated antigens be fused to listeriolysin. In another embodiment, one or more fusion proteins, each fusion protein comprising a truncated form of listeriolysin fused to a different tumor associated antigen, can be used. As demonstrated herein, administration of the vaccines of the present invention decreased the size of existing tumors and inhibits formation of primary tumors. No other stimulation following antigen presentation was required to induce this response.

There exists a long-felt need to develop compositions and methods to treat cancer and develop an immune response to a tumor. The present invention meets this need.

SUMMARY OF THE INVENTION

The present invention includes a method of inducing an immune response to a tumor, the method comprising administering to a mammal a *Listeria* vaccine strain wherein the *Listeria* vaccine strain comprises a truncated LLO protein fused to an antigen wherein the antigen is expressed on the tumor, further wherein the antigen is selected from the group consisting of Her-2/neu or a fragment thereof, bcr/abl, HPVE6, E7, MZ2-E, MAGE-1 and MUC-1, thereby inducing an immune response to a tumor.

In one aspect of the present invention, the *Listeria* vaccine strain is *Listeria monocytogenes*.

In another aspect of the present invention, the antigen is a tumor antigen.

In yet another aspect of the present invention, the fragment of Her-2/neu is selected from the group consisting of an EC1, an EC2, an EC3, an IC1 and an IC2 fragment.

In one aspect of the present invention, the mammal is a human.

The present invention includes a method of treating cancer in a mammal, the method comprising administering to a mammal a *Listeria* vaccine strain wherein the *Listeria* vaccine strain comprises a truncated LLO protein fused to an antigen, wherein a tumor in the mammal expresses the antigen fused to the truncated LLO protein, further wherein the antigen is selected from the group consisting of Her-2/neu or a fragment thereof, bcr/abl, HPVE6, E7, MZ2-E, MAGE-1 and MUC-1 thereby treating cancer.

In one aspect of the invention, the *Listeria* vaccine strain is *Listeria monocytogenes*.

In another aspect of the invention, the antigen is a tumor antigen.

In still another aspect of the invention, the fragment of Her-2/neu is selected from the group consisting of an EC1, an EC2, an EC3, an IC1 and an IC2 fragment.

In one aspect of the invention, the mammal is a human.

The present invention includes a kit for inducing an immune response to a tumor, the kit comprising a *Listeria* vaccine strain comprising a truncated LLO protein fused to an antigen, wherein the antigen is an antigen expressed on the tumor, further wherein the antigen is selected from the group consisting of Her-2/neu or a fragment thereof, bcr/abl, HPVE6, E7, MZ2-E, MAGE-1 and MUC-1, the kit further comprising an applicator and an instructional material for the use thereof.

The present invention includes a kit for treating cancer in a mammal, the kit comprising a *Listeria* vaccine strain wherein the *Listeria* vaccine strain comprises a truncated LLO protein fused to an antigen, wherein a tumor in the mammal expresses the antigen fused to the truncated LLO protein, further wherein the antigen is selected from the group consisting of Her-2/neu or a fragment thereof, bcr/abl, HPVE6, E7, MZ2-E, MAGE-1 and MUC-1, the kit further comprising an applicator and an instructional material for the use thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1 provides data from experiments wherein mice in each immunization group were challenged with parental RENCA.

FIG. 2 provides data from experiments wherein mice in each immunization group were challenged with parental CT26.

FIG. 3 provides data from experiments wherein mice from each immunization group were challenged with RENCA transfected with the same NP used to transform the *L. monocytogenes* (RENCANP).

FIG. 4 provides data from experiments wherein mice from each immunization group were challenged with CT26 transfected with the same NP used to transform the *L. monocytogenes* (CT26NP).

FIG. 5 is a bar graph which provides data from experiments wherein it was shown that CTL generated by immunizing Balb/c mice with LM-NP can kill tumor cells CT26 and RENCA that express NP in vitro.

DETAILED DESCRIPTION OF THE INVENTION

Figure 1:
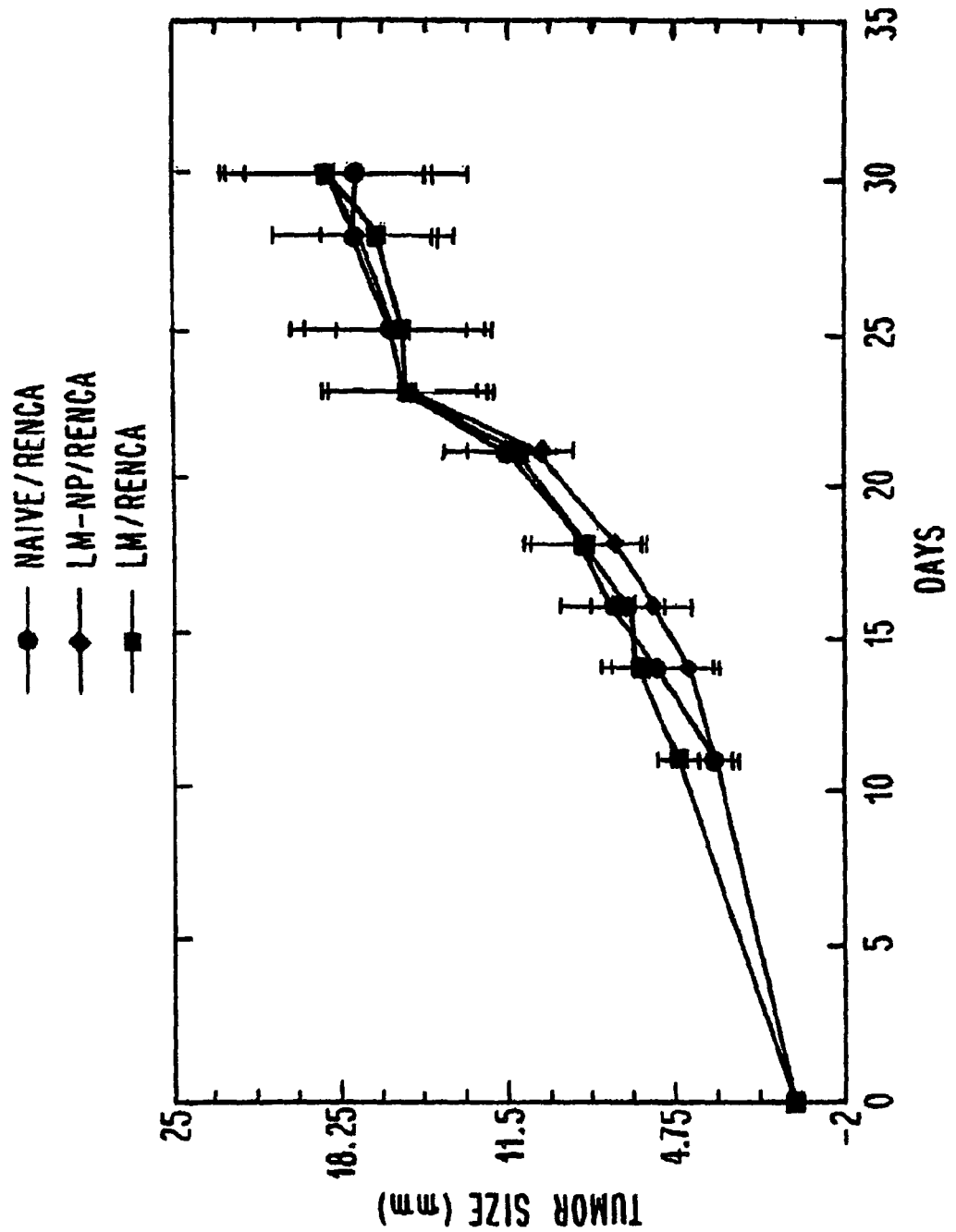
FIGS. 1 through 4 provide line graphs from experiments wherein mice were immunized with either saline (solid circle), *L. monocytogenes* (solid box), or recombinant *L. monocytogenes* transformed to express influenza nucleoprotein (LM-NP) (solid diamond) and then subsequently challenged with either CT26 or RENCA which had been transfected with the same influenza nucleoprotein (NP) gene that was used to transform the *L. monocytogenes* vector (CT26-NP or RENCA-NP, respectively) or with the parental CT26 or RENCA line.

HER-2/neu is an EGF receptor family member that is over-expressed in many human cancers [breast (40%), melanoma (30%), pancreatic (20%), ovarian (30%) & gastric cancer (19%)]. It is thus used extensively as a target antigen in cancer vaccine strategies. The present invention includes *Listeria monocytogenes* strains that express overlapping fragments of the HER-2/neu molecule fused to listeriolysin-O (LLO). Since HER-2/neu is a very large transmembrane protein of 185 kDa, it was divided into five overlapping fragments for the construction of five separate vaccines, each of which, as demonstrated by the data disclosed herein, can be secreted by *Listeria monocytogenes*. Further, the present invention demonstrates that these *L. monocytogenes* strains can express these fragments to induce a cytotoxic T cell response, control tumor growth in a mammalian model of breast cancer and break tolerance to an endogenous tumor antigen.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"Antigen" is used herein to refer to a substance that when placed in contact with an organism, results in a detectable immune response. An antigen may include a lipid, peptide, protein, carbohydrate, nucleic acid, or combinations and variations thereof.

By the term "applicator" as the term is used herein, is meant any device including, but not limited to, a hypodermic syringe, a pipette, and the like, for administering the proteins and *Listeria* strains of the invention to a mammal.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., retroviruses, adenoviruses, and adeno-associated viruses) that incorporate the recombinant polynucleotide.

A "fusion protein" as used herein refers to a protein wherein the protein comprises two or more proteins linked together by peptide bonds or other chemical bonds. The proteins can be linked together directly by a peptide or other chemical bond, or with one or more amino acids between the two or more proteins, referred to herein as a spacer.

"Fragment" is used herein to refer to a protein, peptide, or nucleic acid that is shorter or comprises fewer amino acids or nucleotides than the full length protein, peptide, or nucleic acid. By way of example, a fragment of a protein comprises less than the full length protein.

A "genomic DNA" is a DNA strand which has a nucleotide sequence homologous with a gene. By way of example, both a fragment of a chromosome and a cDNA derived by reverse transcription of a mammalian mRNA are genomic DNAs.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity."

In addition, when the terms "homology" or "identity" are used herein to refer to the nucleic acids and proteins, it should be construed to be applied to homology or identity at both the nucleic acid and the amino acid sequence levels.

As used herein, the terms "gene" and "recombinant gene" refer to nucleic acid molecules comprising an open reading frame encoding a polypeptide of the invention. Such natural allelic variations can typically result in 1-5% variance in the nucleotide sequence of a given gene. Alternative alleles can be identified by sequencing the gene of interest in a number of different individuals or organisms. This can be readily carried out by using hybridization probes to identify the same genetic locus in a variety of individuals or organisms. Any and all such nucleotide variations and resulting amino acid polymorphisms or variations that are the result of natural allelic variation and that do not alter the functional activity are intended to be within the scope of the invention.

"Immunogenicity" is used herein to refer to the innate ability of an antigen or organism to elicit an immune response in an animal when the antigen or organism is administered to the animal. Thus, "enhancing the immunogenicity" refers to increasing the ability of an antigen or organism to elicit an immune response in an animal when the antigen or organism is administered to an animal. The increased ability of an antigen or organism to elicit an immune response can be measured by, among other things, a greater number of antibodies to an antigen or organism, a greater diversity of antibodies to an antigen or organism, a greater number of T-cells specific for an antigen or organism, a greater cytotoxic or helper T-cell response to an antigen or organism, and the like.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "*Listeria* vaccine strain" is used herein to refer to a recombinant *Listeria* organism that expresses a heterologous antigen.

By describing two polynucleotides as "operably linked" is meant that a single-stranded or double-stranded nucleic acid moiety comprises the two polynucleotides arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

Preferably, when the nucleic acid encoding the desired protein further comprises a promoter/regulatory sequence, the promoter/regulatory is positioned at the 5' end of the desired protein coding sequence such that it drives expression of the desired protein in a cell. Together, the nucleic acid encoding the desired protein and its promoter/regulatory sequence comprise a "transgene."

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a living human cell under most or all physiological conditions of the cell.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living human cell substantially only if the cell is a cell of the tissue type corresponding to the promoter.

A "polyadenylation sequence" is a polynucleotide sequence which directs the addition of a poly A tail onto a transcribed messenger RNA sequence.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Transform", "transforming", and "transformation" is used herein to refer to a process of introducing an isolated nucleic acid into the interior of an organism.

"Truncated LLO protein" is used herein to refer to an LLO protein having from the PEST-like sequence (SEQ ID NO:10) to the cysteine at position 484 in SEQ ID NO:2.

Methods and Compositions

The present invention comprises a method for inducing an immune response to a tumor comprising administering to a mammal, preferably a human, a bacterial vaccine strain comprising an antigen expressed on the tumor fused to an LLO protein. As disclosed elsewhere herein, the method of the present invention result in, inter alia, a lack of tumor growth, death of tumor tissue, and the abrogation of tolerance to a tumor and the antigens expressed therefrom.

The present invention further comprises a method for treating cancer in a mammal, preferably a human, a *Listeria* vaccine strain comprising a truncated LLO protein fused to an antigen wherein a tumor in the mammal expresses the antigen fused to the truncated LLO protein. As disclosed herein, administering a *Listeria* vaccine strain expressing a truncated LLO protein expressing an antigen that is also expressed on a tumor, or individual tumor cells, results in, among other things, regression of the tumor, necrotic tumor tissue, and a longer life for a mammal with a tumor compared to those mammals not administered a *Listeria* vaccine strain.

The *Listeria* vaccine vector of the present invention can be constructed using techniques known in the art including expression of an antigen fused to an LLO protein from a plasmid, from chromosomal expression, or by other methods disclosed elsewhere herein.

The antigen-LLO protein of the present invention can be synthesized using recombinant DNA methodology. Generally this involves creating a DNA sequence that encodes the antigen-LLO protein, placing the DNA in an expression cassette, such as the plasmid of the present invention, under the control of a particular promoter/regulatory element, and expressing the protein.

DNA encoding the antigen-LLO protein (e.g. LLO fused to a Her-2/neu antigen, an E6 or E7 antigen, and the like) of the present invention may be prepared by any suitable method, including, for example, cloning and restriction of appropriate sequences or direct chemical synthesis by methods such as the phosphotriester method of Narang et al. (1979, Meth. Enzymol. 68: 90-99); the phosphodiester method of Brown et al. (1979, Meth. Enzymol 68: 109-151); the diethylphosphoramidite method of Beaucage et al. (1981, Tetra. Lett., 22: 1859-1862); and the solid support method of U.S. Pat. No. 4,458,066.

Chemical synthesis produces a single stranded oligonucleotide. This may be converted into double stranded DNA by hybridization with a complementary sequence, or by polymerization with a DNA polymerase using the single strand as a template. One of skill in the art would recognize that while chemical synthesis of DNA is limited to sequences of about 100 bases, longer sequences may be obtained by the ligation of shorter sequences.

Alternatively, as demonstrated herein, subsequences may be cloned and the appropriate subsequences cleaved using appropriate restriction enzymes. The fragments may then be ligated to produce the desired DNA sequence.

The present invention includes an isolated nucleic acid encoding a non-hemolytic truncated LLO molecule, or a fragment thereof, fused to an antigen. Listeriolysin O (LLO) binds to cholesterol-containing membranes wherein it oligomerizes to form pores. The oligomerization is dependent on the presence of a reduced cystine residue at position 484 in the sequence that is required for oligomerization. The hly gene encodes a proprotein of 529 residues (GenBank Accession No. P13128; SEQ ID NO:2; nucleic acid is GenBank Accession No. X15127; SEQ ID NO:1), the first 25 amino acids are the signal sequence and are cleaved from LLO when it is secreted by the bacterium. Thus, the full length active LLO protein is approximately 504 residues. For purposes of the present invention, by "truncated LLO or .DELTA.LLO" it is meant a fragment of LLO that comprises the PEST-like domain (SEQ ID NO:10) and which does not contain the activation domain at the carboxy terminus and does not include cysteine 484.

The LLO of the present invention includes an isolated nucleic acid encoding a non-hemolytic truncated LLO molecule, or a fragment thereof, fused to an antigen, wherein the nucleic acid is at least about 80% homologous, more preferably at least about 90% homologous with a nucleic acid having the sequence of SEQ ID NO:1. Preferably, the nucleic acid is at least about 95% homologous, more preferably at least about 96% homologous with a nucleic acid having the sequence of SEQ ID NO:1, more preferably at least about 97% homologous with a nucleic acid having the sequence of SEQ ID NO:1, more preferably at least about 98% homologous with a nucleic acid having the sequence of SEQ ID NO:1, more preferably at least about 99% homologous with a nucleic acid having the sequence of SEQ ID NO:1, most preferably, about 99.9% homologous to SEQ ID NO:1, disclosed herein. Even more preferably, the nucleic acid is SEQ ID NO:1.

The isolated nucleic acid of the invention should be construed to include an RNA or a DNA sequence encoding an LLO protein of the invention, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Such modifications are detailed elsewhere herein. Any and all combinations of modifications of the nucleotide sequences are contemplated in the present invention.

In other related aspects, the invention includes an isolated nucleic acid encoding a truncated LLO protein and an isolated nucleic acid encoding an antigen operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

Expression of a truncated LLO protein and an antigen, either alone or fused to a detectable tag polypeptide in a cell or mammal may be accomplished by generating a plasmid, viral, or other type of vector comprising the desired nucleic acid operably linked to a promoter/regulatory sequence which serves to drive expression of the protein, with or without tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, both of which were used in the experiments disclosed herein, as well as the Rous sarcoma virus promoter, and the like. Moreover, inducible and tissue specific expression of the nucleic acid encoding a truncated LLO protein and an antigen may be accomplished by placing the nucleic acid encoding a truncated LLO protein and an antigen, with or without a tag, under the control of an inducible or tissue specific promoter/regulatory sequence. Examples of tissue specific or inducible promoter/regulatory sequences which are useful for his purpose include, but are not limited to the MMTV LTR inducible promoter, as disclosed elsewhere herein, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Expressing a truncated LLO protein and an antigen using a vector allows the expression of large amounts of recombinantly produced protein. Selection of any particular plasmid vector or other DNA vector is not a limiting factor in this invention and a wide plethora of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The invention thus includes a *Listeria* vaccine strain comprising an isolated nucleic acid encoding a truncated LLO protein and an antigen. The incorporation of a desired nucleic acid into a vector and the choice of vectors is well-known in the art as described in, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The invention also includes cells, viruses, proviruses, and the like, containing such vectors. Methods for producing cells comprising vectors and/or exogenous nucleic acids are well-known in the art. See, for example, Sambrook et al. (1989, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding a truncated LLO protein and an antigen may be cloned into various plasmid vectors. However, the present invention should not be construed to be limited to plasmids or to any particular vector. Instead, the present invention should be construed to encompass a wide plethora of vectors which are readily available and/or well-known in the art.

The present invention further includes a truncated LLO polypeptide, or a fragment thereof, fused to an antigen, wherein the polypeptide is at least about 80% homologous, more preferably at least about 90% homologous with a polypeptide sequence having the sequence of SEQ ID NO:2. Preferably, the polypeptide is at least about 95% homologous, more preferably at least about 96% homologous with a polypeptide having the sequence of SEQ ID NO:2, more preferably at least about 97% homologous with a polypeptide having the sequence of SEQ ID NO:2, more preferably at least about 98% homologous with a polypeptide having the sequence of SEQ ID NO:2, more preferably at least about 99% homologous with a polypeptide having the sequence of SEQ ID NO:2, most preferably, about 99.9% homologous to SEQ ID NO:2, disclosed herein. Even more preferably, the polypeptide is SEQ ID NO:2.

The present invention should not be construed as being limited solely to the nucleic and amino acid sequences disclosed herein. Once armed with the present invention, it is readily apparent to one skilled in the art that other nucleic acids encoding an LLO protein fused to an antigen can be obtained by following the procedures described herein in the experimental details section for the generation of other LLO/antigen fusion proteins as disclosed herein (e.g., site-directed mutagenesis, frame shift mutations, and the like), and procedures that are well-known in the art or to be developed.

Further, any other number of procedures may be used for the generation of derivative or variant forms of an LLO/antigen fusion protein using recombinant DNA methodology well known in the art such as, for example, that described in Sambrook et al. (1989, Molecular Cloning: A Laboratory Manual, Cold Spring Harbor Laboratory Press, New York) and Ausubel et al. (1997, Current Protocols in Molecular Biology, Green & Wiley, New York), and elsewhere herein.

Procedures for the introduction of amino acid changes in a protein or polypeptide by altering the DNA sequence encoding the polypeptide are well known in the art and are also described in Sambrook et al. (1989, supra); Ausubel et al. (1997, supra).

The invention includes a nucleic acid encoding an LLO/antigen fusion protein wherein a nucleic acid encoding a tag polypeptide is covalently linked thereto. That is, the invention encompasses a chimeric nucleic acid wherein the nucleic acid sequence encoding a tag polypeptide is covalently linked to the nucleic acid encoding an LLO/antigen fusion protein. Such tag polypeptides are well known in the art and include, for instance, green fluorescent protein (GFP), myc, myc-pyruvate kinase (myc-PK), His$_6$, maltose biding protein (MBP), an influenza virus hemagglutinin tag polypeptide, a flag tag polypeptide (FLAG), and a glutathione-S-transferase (GST) tag polypeptide. However, the invention should in no way be construed to be limited to the nucleic acids encoding the above-listed tag polypeptides. Rather, any nucleic acid sequence encoding a polypeptide which may function in a manner substantially similar to these tag polypeptides should be construed to be included in the present invention.

The nucleic acid comprising a nucleic acid encoding a tag polypeptide can be used to localize an LLO/antigen fusion protein within a cell, a tissue, and/or a whole organism (e.g., a mammalian embryo), detect an LLO/antigen fusion protein secreted from a cell, and to study the role(s) of an LLO/antigen fusion protein in a cell. Further, addition of a tag polypeptide facilitates isolation and purification of the "tagged" protein such that the proteins of the invention can be produced and purified readily.

As an example, DNA encoding the fusion protein of the present invention may be cloned using DNA amplification methods such as polymerase chain reaction (PCR). Thus, the gene for truncated LLO is PCR amplified, using a sense primer comprising a suitable restriction site and an antisense primer comprising another restriction site, preferably a non-identical restriction site to facilitate cloning. The same is repeated for the isolated nucleic acid encoding an antigen. Ligation of the truncated LLO and antigen sequences and insertion into a plasmid or vector produces a vector encoding truncated LLO joined to a terminus of the antigen. The two molecules are joined either directly or by a short spacer introduced by the restriction site.

While the two molecules are preferably essentially directly joined together, one of skill will appreciate that the molecules may be separated by a peptide spacer consisting of one or more amino acids. Generally the spacer will have no specific biological activity other than to join the proteins or to preserve some minimum distance or other spatial relationship between them. However, the constituent amino acids of the spacer may be selected to influence some property of the molecule such as the folding, net charge, or hydrophobicity.

The present invention comprises a truncated LLO protein, or fragment thereof, fused to an antigen. Methods for the fusion of an antigen to an LLO protein are disclosed elsewhere herein. The truncated LLO protein, or fragment thereof, of the present invention comprises the LLO amino acid sequence set forth in SEQ ID NO:2. The skilled artisan will recognize that the LLO protein of the present invention need not be that which is set forth exactly in SEQ ID NO:2, but rather that other alterations, modifications, or changes can be made that retain the functional characteristics of an LLO protein fused to an antigen as set forth elsewhere herein.

It will be appreciated, of course, that the peptides may incorporate amino acid residues which are modified without affecting activity. For example, the termini may be derivatized to include blocking groups, i.e. chemical substituents suitable to protect and/or stabilize the N- and C-termini from "undesirable degradation", a term meant to encompass any type of enzymatic, chemical or biochemical breakdown of the compound at its termini which is likely to affect the function of the compound, i.e. sequential degradation of the compound at a terminal end thereof.

The present invention also provides for analogs of truncated LLO, or fragments thereof, proteins or peptides. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:
glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced are sequences which have phosphorylated amino acid residues, e.g., phosphotyrosine, phosphoserine, or phosphothreonine.

Also included are polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

The present invention further comprises an antigen fused to a truncated LLO protein in a *Listeria* vaccine strain. This is because, as demonstrated by the data disclosed herein, fusion of an antigen to a truncated LLO protein and expressing the LLO/antigen from a *Listeria* vaccine strain results in, inter alia, specific lysis of cells expressing the antigen, control of tumor growth in tumors expressing the antigen, regression of tumors expressing the antigen and the ability to break tolerance to a tumor expressing the antigen. That is, as the data disclosed herein demonstrate, administration of a *Listeria* vaccine strain to an animal wherein the *Listeria* vaccine strain comprises a truncated LLO/antigen protein, when administered to an animal, results in the induction of antigen specific cytotoxic lymphocytes capable of infiltrating tumor or infected cells. When armed with the present disclosure, and the methods and compositions disclosed herein, the skilled artisan will readily realize that the present invention in amenable to treatment and/or prevention of a multitude of diseases.

The antigen fused to the truncated LLO protein, or fragment thereof is preferably an antigen derived from a tumor or an infectious organism, including, but not limited to fungal pathogens, bacteria, parasites, helminths, viruses, and the like. An antigen comprising the fusion protein of the present invention includes but is not limited to, tetanus toxoid, hemagglutinin molecules from influenza virus, diphtheria toxoid, HIV gp120, HIV gag protein, IgA protease, insulin peptide B, *Spongospora* subterranea antigen, vibriose antigens, *Salmonella* antigens, pneumococcus antigens, respiratory syncytial virus antigens, *Haemophilus influenza* outer membrane proteins, *Helicobacter pylori* urease, *Neisseria meningitidis* pilins, *N. gonorrhoeae* pilins, the melanoma-associated antigens (TRP-2, MAGE-1, MAGE-3, gp-100, tyrosinase, MART-1, HSP-70, beta-HCG), human papilloma virus antigens E1, E2, E6 and E7 from type HPV-16, -18, -31, -33, -35 or -45 human papilloma viruses, the tumor antigens CEA, the ras protein, mutated or otherwise, the p53 protein, mutated or otherwise, Muc1, pSA, the antigens well known in the art from the following diseases; cholera, diphtheria, *Haemophilus*, hepatitis A, hepatitis B, influenza, measles, meningitis, mumps, pertussis, small pox, pneumococcal pneumonia, polio, rabies, rubella, tetanus, tuberculosis, typhoid, Varicella-zoster, whooping cough, yellow fever, the immunogens and antigens from Addison's disease, allergies, anaphylaxis, Bruton's syndrome, cancer, including solid and blood borne tumors, eczema, Hashimoto's thyroiditis, polymyositis, dermatomyositis, type 1 diabetes mellitus, acquired immune deficiency syndrome, transplant rejection, such as kidney, heart, pancreas, lung, bone, and liver transplants, Graves' disease, polyendocrine autoimmune disease, hepatitis, microscopic polyarteritis, polyarteritis nodosa, pemphigus, primary biliary cirrhosis, pernicious anemia, coeliac disease, antibody-mediated nephritis, glomerulonephritis, rheumatic diseases, systemic lupus erthematosus, rheumatoid arthritis, seronegative spondylarthritides, rhinitis, sjogren's syndrome, systemic sclerosis, sclerosing cholangitis, Wegener's granulomatosis, dermatitis herpetiformis, psoriasis, vitiligo, multiple sclerosis, encephalomyelitis, Guillain-Barre syndrome, myasthenia gravis, Lambert-Eaton syndrome, sclera, episclera, uveitis, chronic mucocutaneous candidiasis, urticaria, transient hypogammaglobulinemia of infancy, myeloma, X-linked hyper IgM syndrome, Wiskott-Aldrich syndrome, ataxia telangiectasia, autoimmune hemolytic anemia, autoimmune thrombocytopenia, autoimmune neutropenia, Waldenstrom's macroglobulinemia, amyloidosis, chronic lymphocytic leukemia, non-Hodgkin's lymphoma, malarial circumsporozite protein, microbial antigens, viral antigens, autoantigens, and lesteriosis.

Tumor antigens contemplated in the present invention include, but are not limited to, any of the various MAGEs (Melanoma-Associated Antigen E), including MAGE 1 (e.g., GenBank Accession No. M77481), MAGE 2 (e.g., GenBank Accession No. U03735), MAGE 3, MAGE 4, etc.; any of the various tyrosinases; mutant ras; mutant p53 (e.g., GenBank Accession No. X54156 and AA494311); and p97 melanoma antigen (e.g., GenBank Accession No. M12154). Other tumor-specific antigens include the Ras peptide and p53 peptide associated with advanced cancers, the HPV 16/18 and E6/E7 antigens associated with cervical cancers, MUC1-KLH antigen associated with breast carcinoma (e.g., GenBank Accession No. J03651), CEA (carcinoembryonic antigen) associated with colorectal cancer (e.g., GenBank Accession No. X98311), gp100 (e.g., GenBank Accession No. S73003) or MART1 antigens associated with melanoma, and the PSA antigen associated with prostate cancer (e.g., GenBank Accession No. X14810). The p53 gene sequence is known (See e.g., Harris et al. (1986) Mol. Cell. Biol., 6:4650-4656) and is deposited with GenBank under Accession No. M14694. Tumor antigens encompassed by the present invention further include, but are not limited to, Her-2/Neu (e.g. GenBank Accession Nos. M16789.1, M16790.1, M16791.1, M16792.1), NY-ESO-1 (e.g. GenBank Accession No. U87459), hTERT (aka telomerase) (GenBank Accession. Nos. NM003219 (variant 1), NM198255 (variant 2), NM 198253 (variant 3), and NM 198254 (variant 4), proteinase 3 (e.g. GenBank Accession Nos. M29142, M75154, M96839, X55668, NM 00277, M96628 and X56606) HPV E6 and E7 (e.g. GenBank Accession No. NC 001526) and WT-1 (e.g. GenBank Accession Nos. NM000378 (variant A), NM024424 (variant B), NM 024425 (variant C), and NM024426 (variant D)). Thus, the present invention can be used as immunotherapeutics for cancers including, but not limited to, cervical, breast, colorectal, prostate, lung cancers, and for melanomas.

The present invention further includes, but is not limited to the antigens from the following infectious diseases; measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Japanese encephalitis (e.g., GenBank Accession No. E07883), dengue (e.g., GenBank Accession No. M24444), hantavirus, and HIV (e.g., GenBank Accession No. U18552). Bacterial and parasitic antigens will be derived from known causative agents responsible for diseases including, but not limited to, diphtheria, pertussis (e.g., GenBank Accession No. M35274), tetanus (e.g., GenBank Accession No. M64353), tuberculosis, bacterial and fungal pneumonias (e.g., *Haemophilus influenzae, Pneumocystis carinii*, etc.), cholera, typhoid, plague, shigellosis, salmonellosis (e.g., GenBank Accession No. L03833), Legionnaire's Disease, Lyme disease (e.g., GenBank Accession No. U59487), malaria (e.g., GenBank Accession No. X53832), hookworm, onchocerciasis (e.g., GenBank Accession No. M27807), schistosomiasis (e.g., GenBank Accession No. L08198), trypanosomiasis, leshmaniasis, giardiasis (e.g., GenBank Accession No. M33641), amoebiasis, filariasis (e.g., GenBank Accession No. J03266), borreliosis, and trichinosis.

Particularly contemplated is a method of treating cancer comprising administering a mammal a *Listeria* vaccine strain comprising an LLO protein fused to an antigen wherein the mammal has tumors expressing the antigen fused to an LLO protein. This is because, as demonstrated by the data disclosed herein, administering a *Listeria* vaccine strain expressing an LLO protein fused to a fragment of Her-2/neu to a mammal results in regression of existing tumors, an abrogation of tolerance to existing tumors, and the death of tumor tissue. Preferably, the fragment of an Her-2/neu antigen comprises the EC1 fragment (residues 20-326 of the Her-2/neu protein; SEQ ID NO:3), the EC2 fragment (residues 303-501 of the Her-2/neu protein; SEQ ID NO:4), the EC3 fragment (residues 479-655 of the Her-2/neu protein; SEQ ID NO:5), the IC1 fragment (residues 690-1081 of the Her-2/neu protein; SEQ ID NO:6) and the IC2 fragment (residues 1020-1260 of the Her-2/neu protein; SEQ ID NO:7). In addition, the present invention can comprise any of the antigens disclosed herein or well known in the art, including fragments thereof, as well as additional fragments of the Her-2/neu antigen, the nucleic acid sequence (SEQ ID NO:9) and the amino acid (SEQ ID NO:8) of which are well known in the art.

The antigens of these and other diseases are well known in the art, and the skilled artisan, when equipped with the present disclosure and the methods and techniques described herein will readily be able to construct a fusion protein comprising a truncated LLO protein and an antigen for use in the present invention.

The skilled artisan, when armed with the present disclosure and the data herein, will readily appreciate that a truncated LLO protein, or fragments thereof, can be fused to the antigens enumerated herein, and others well known in the art. While not wishing to be bound by any particular theory, the data disclosed herein demonstrate that a *Listeria* vaccine strain expressing an antigen fused to an LLO protein, or fragment thereof, is processed in the cellular cytoplasm and presented in the context of the major histocompatibility complex to effector lymphocytes. Therefore, as is well known by those having knowledge of the fundamental tenets of immunology, an antigen fused to an LLO protein, or fragment thereof, will be degraded through well-known cellular pathways and be displayed on the cell surface for recognition by effector and helper lymphocytes. As is well known in the art, the degradation process results in short peptide sequences presented in the context of the major histocompatability complex that are subsequently recognized by T-cells, resulting in effector or helper functions. Thus, while the present invention is described in reference to certain antigens, the skilled artisan will readily appreciate that the present invention is amendable to any antigen disclosed herein or otherwise well known in the art.

The immune response to *L. monocytogenes* has been shown to be a TH1, CD4+ T cell and CD8+ T cell response with only very weak humoral responses being engendered. Recombinant forms of the wild-type bacterium have been developed which express the foreign proteins β-galactosidase (Schafer et al., J. Immunol. 1992, 149, 53-59), influenza nucleoprotein and HIV gag and nef gene product. Recombinant techniques have been developed to stably integrate these proteins into the Listerial chromosome in such a way that they are secreted by the bacterium. All of these recombinant vectors elicit strong, antigen specific, CTL responses in vivo. Thus, this bacterium serves as an ideal vector for boosting the CTL response to antigens, and in particular tumor associated antigens, and provides a unique system to prime the cellular immune response as a vaccine against various diseases, and in particular cancer.

Administration of a live vector such as *L. monocytogenes* results in a long lasting cellular immunity which often cannot be induced with killed preparations or soluble protein and adjuvant. A unique feature of the life-cycle of *L. monocytogenes* is that it invades the host cell and is taken up into a phagosome from which it escapes and then lives and replicates in the cytoplasm (Tilney, L. G. and D. A. Portnoy, J. Cell Biol. 1989 109, 1597). Thus, the *L. monocytogenes* vector provides the ability to target foreign proteins and fragments of proteins to the class I MHC restricted pathway. In addition to being a more efficacious vector, *L. monocytogenes*, which is a gram-positive organism, is also much safer than many other live vectors since it is very susceptible to most antibiotics, including penicillin. It also does not have the problems associated with toxicity from endotoxin which gram negative vectors such as *Salmonella* sp. present. Pre-existing immunity which could prevent effective boosting by a vector which has already been widely used as a vaccine, e.g., Vaccinia or BCG, is not likely to be a problem for *L. monocytogenes*, which has not been used previously in vaccine development. Mutant strains of *L. monocytogenes*, which are avirulent but still induce good immunity, are also available for testing as potential vaccine candidates.

Using a model murine system, it has now been found that *L. monocytogenes* can induce an immune response against a protein expressed by tumor cells. This immune response causes the rejection of tumor cells that have been transferred to healthy, immunized mice and kills tumor cells in mice in which tumor cell growth has already been initiated.

The ability of a vaccine comprising recombinant *L. monocytogenes* to convey specific protective immunity against the growth of CT26, a mouse colorectal carcinoma tumor and RENCA, a murine renal carcinoma, was examined. In preliminary experiments, *L. monocytogenes* was engineered to secrete nucleoprotein (NP) from A/PR/8/34 as a fusion protein with a major secreted *Listerial* protein, listeriolysin O (LLO), the product of the hemolysin gene. LLO is normally expressed and secreted in a host vacuole by *L. monocytogenes* and is required for escape of the bacteria into the cytoplasm. The ability of NP secreting *L. monocytogenes* recombinants to target the class I pathway of antigen processing for recognition by bulk influenza specific T cells from three strains of mice was tested. It was determined that the LLO-NP fusion proteins are appropriately processed for presentation by the three MHC class I haplotypes to which the A/PR/8/34 response is restricted, i.e., $K^d$, $D^b$ and $K^k$. Immunization of Balb/c mice with varying doses of LM-.NP was demonstrated to result in a strong anti-NP CTL response.

Figure 2:
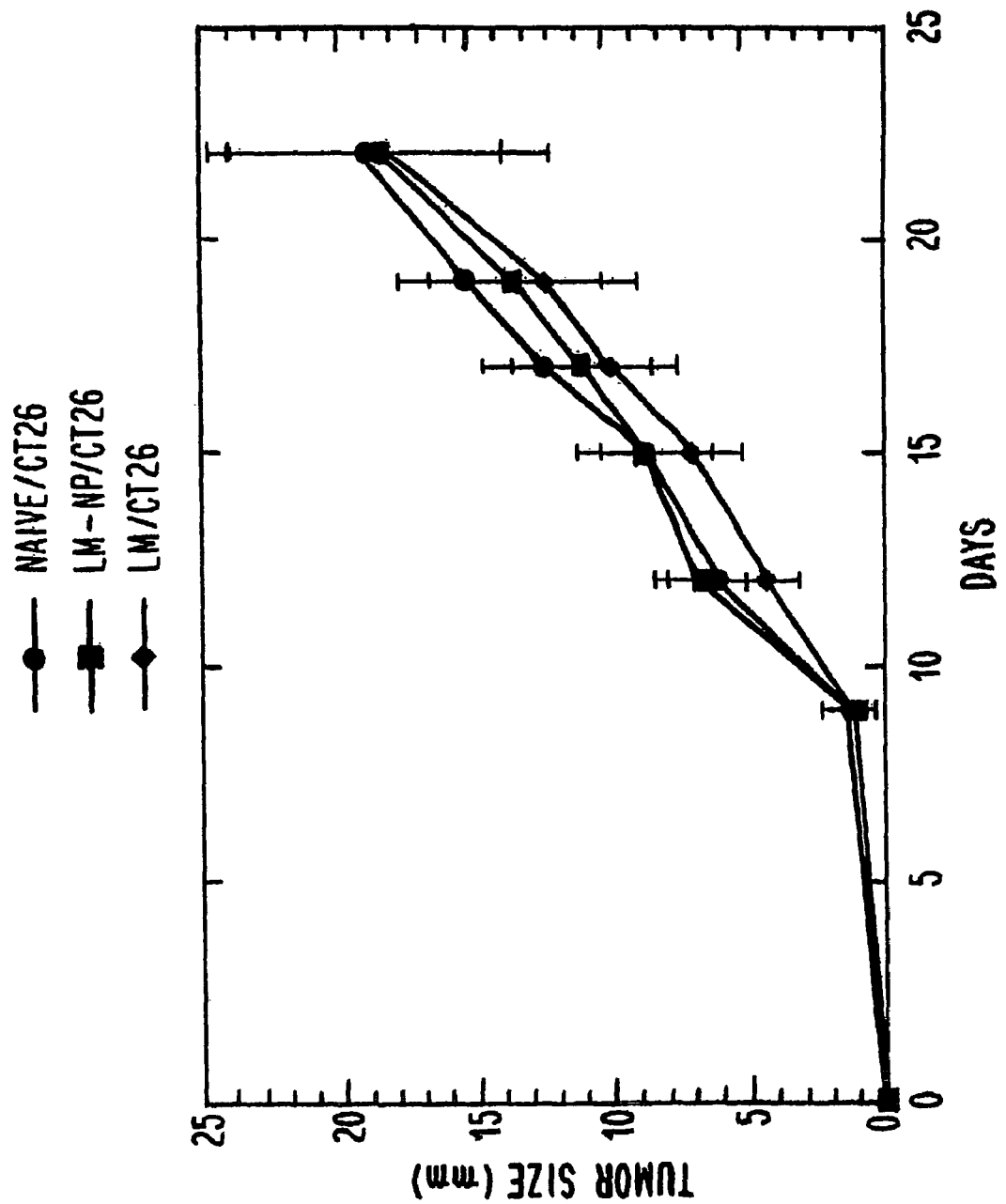
Figure 3:
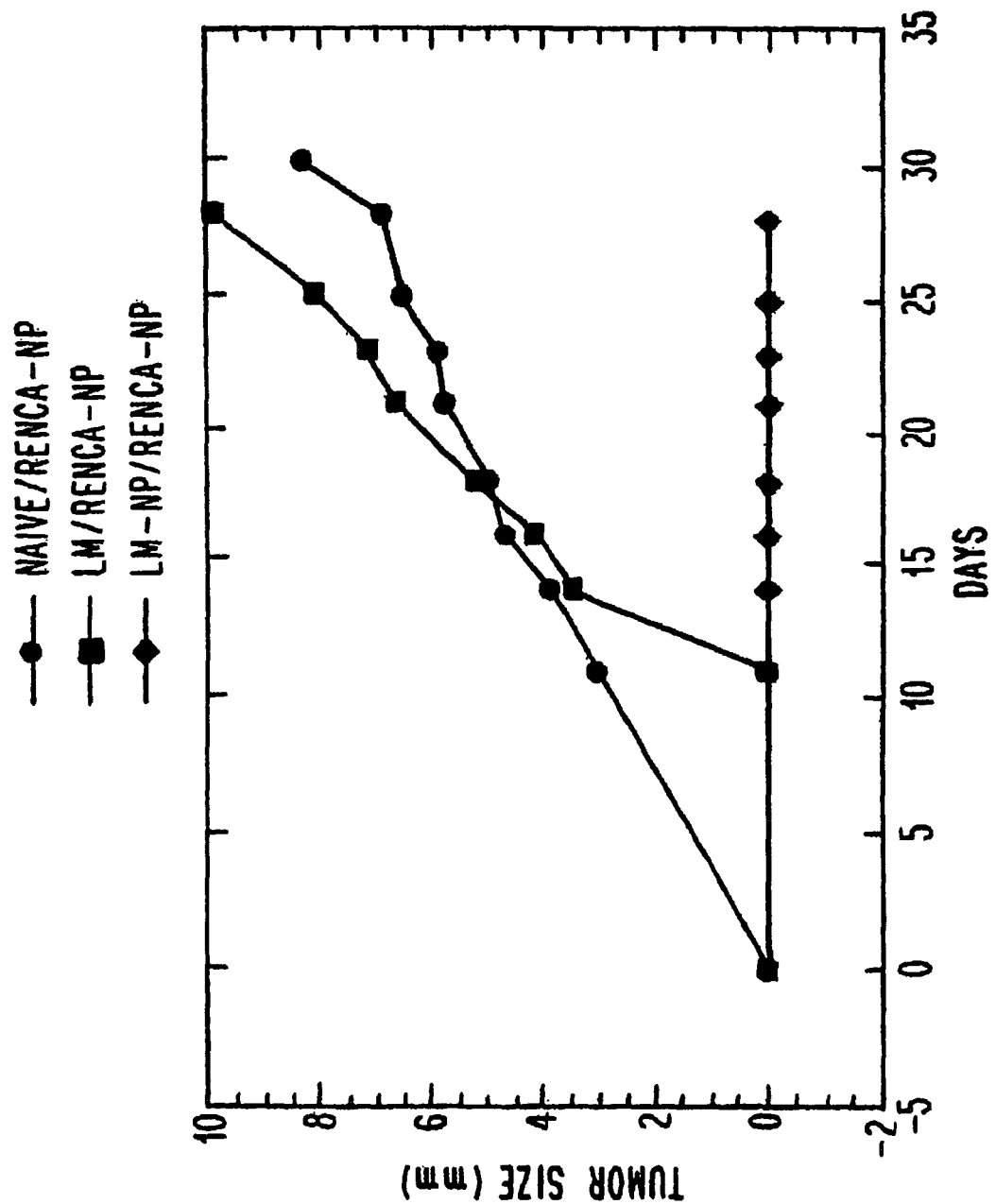
Figure 4:
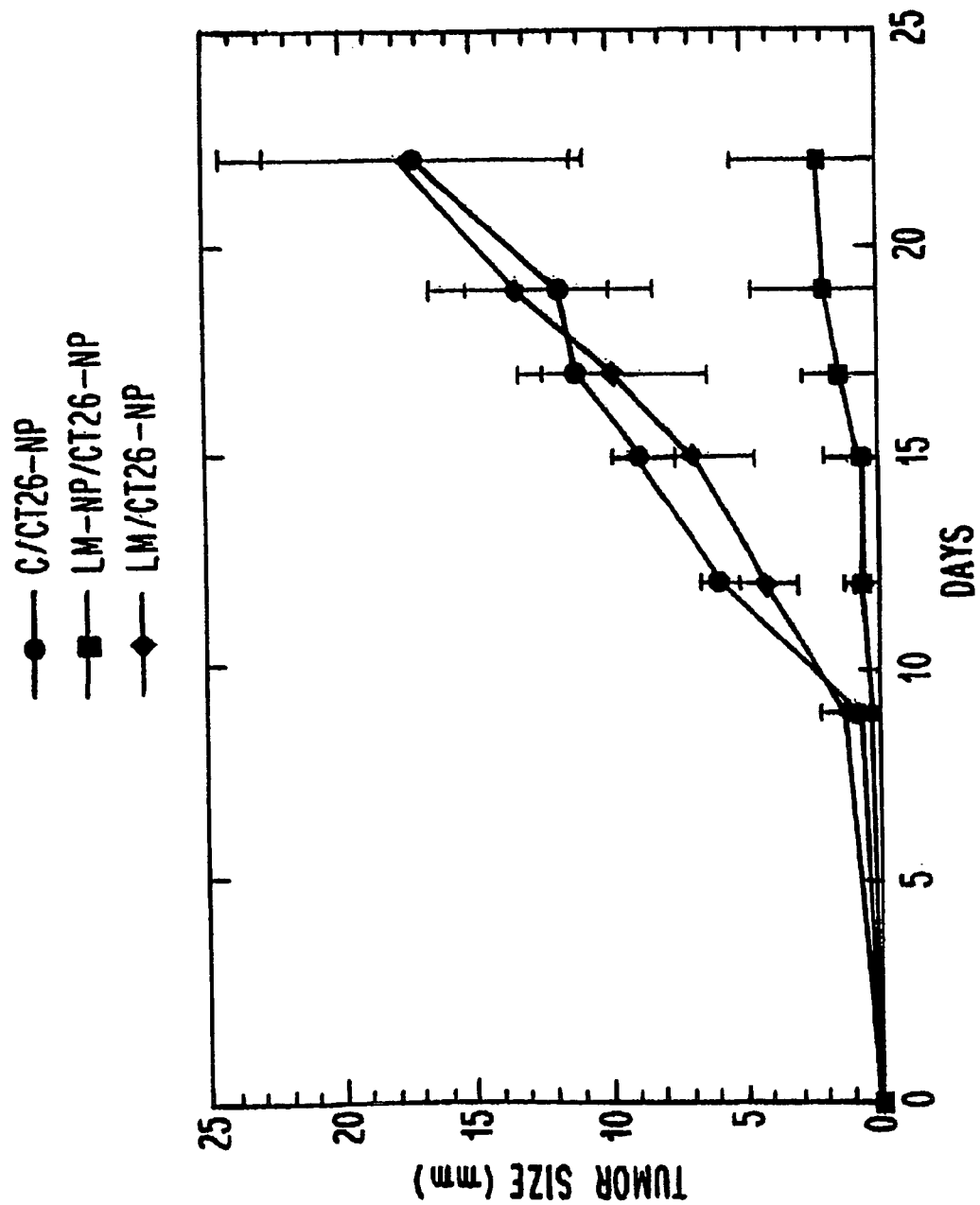

In further experiments, mice were divided into three groups. One group was immunized with one-tenth of an $LD_{50}$ of wild-type *L. monocytogenes*, one group was immunized with sterile saline, and the third group was immunized with a vaccine comprising a recombinant *L. monocytogenes* vector which was-transformed to secrete a fusion protein comprising influenza nucleoprotein (LM-NP) and a truncated form of listeriolysin. In this fusion protein, the listeriolysin is truncated to eliminate the hemolytic activity of the enzyme. After two weeks, each group received a similar booster immunization. This immunization schedule was determined to produce strong CTL responses against influenza nucleoprotein. Two weeks after the last immunization, animals in each group were challenged subcutaneously with a tumoricidal dose of either CT26 or RENCA which had been transfected with the same influenza nucleoprotein gene that was used to transform the *L. monocytogenes* vector (CT26-NP or RENCA-NP, respectively) or with the parental CT26 or RENCA line. Tumor growth was monitored. As shown in FIGS. 3 and 4, animals which received recombinant *Listeria monocytogenes* expressing NP-fusion protein (LM-NP) and which were challenged with the relevant tumor cell expressing NP were protected from further tumor formation. In the CT26-NP group, after 25 days, 6 of the animals showed no detectable tumor growth, 3 had tumors of less than 5.0 mm and one had a tumor of 9.0 mm (see FIG. 4). In the RENCA-NP group, none of the animals showed any signs of tumor growth (see FIG. 3). In contrast, all the mice in the other groups developed tumors between 1.5 and 3.0 cm (see FIGS. 1 and 2).

Figure 6:
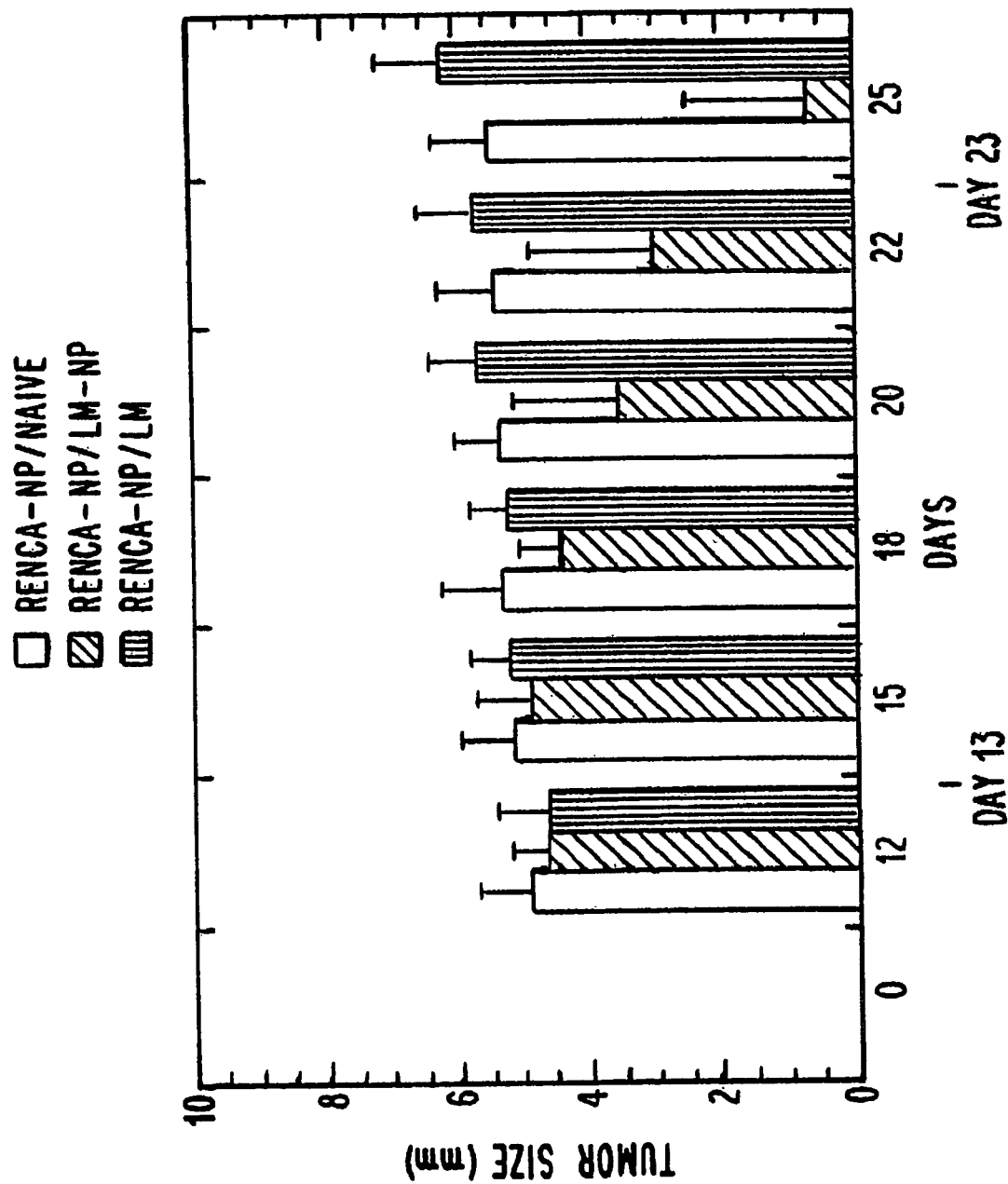
FIG. 6 is a bar graph which provides data from experiments wherein it was shown that immunization by LM-NP causes elimination of RENCA-NP tumor growth.
Figure 7:
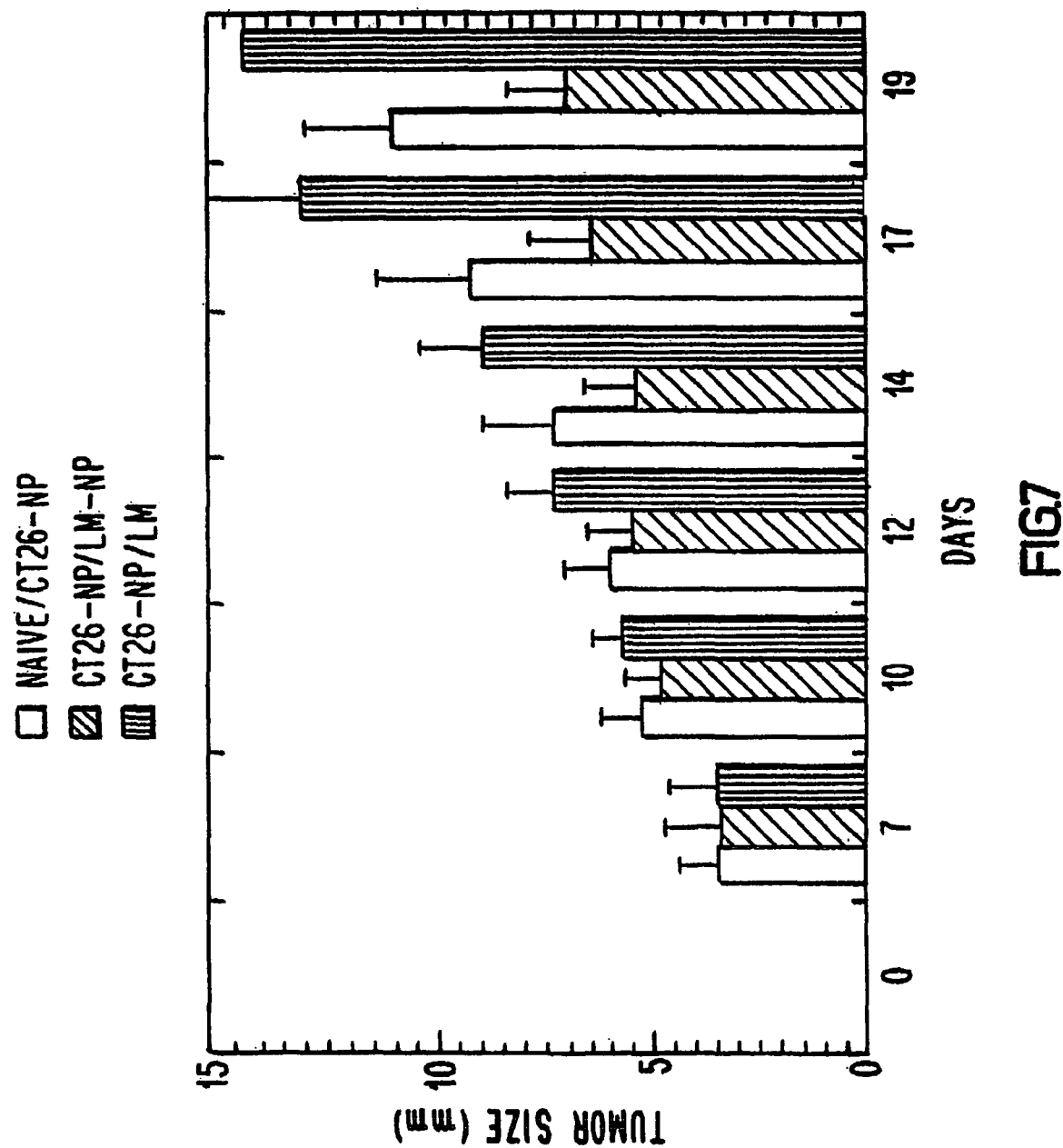
FIG. 7 is a bar graph which provides data from experiments wherein it was shown that immunization by LM-NP causes cessation of CT26-NP tumor growth.

The ability of LM-NP fusion protein to cause regression and depletion of existing tumors was also demonstrated. Tumor cells (either CT26 or RENCA cells) were introduced subcutaneously into mice. After the formation of measurable tumors, the mice were divided into three separate groups. A first group of mice received LM-NP, a second group of mice received wild type *Listeria monocytogenes* and a third group of mice received no further treatment. Mice in groups 1 and 2 were given a subsequent booster of either LM-NP or wild type *Listeria monocytogenes*, respectively. As shown in FIGS. 6 and 7 only the mice that received the vaccine with the LM-NP fusion protein showed regression of tumor growth to the point where the tumor was no longer visible.

Various tumor associated antigens have been identified. Further, much research effort is being expended to identify additional tumor associated antigens. Some groups of tumor associated antigens, also referred to in the art as tumor specific antigens, are tissue specific. Examples include, but are not limited to, tyrosinase for melanoma, PSA and PSMA for prostate cancer and chromosomal cross-overs such as bcr/abl in lymphoma. However, many tumor associated antigens identified occur in multiple tumor types, and some, such as oncogenic proteins which actually cause the transformation event, occur in nearly all tumor types. For example, normal cellular proteins that control cell growth and differentiation, such as p53 and HER-2/neu, can accumulate mutations resulting in up-regulation of expression of these gene products thereby making them oncogenic (McCartey et al. Cancer Research 1998 15:58 2601-5; Disis et al. Ciba Found. Symp. 1994 187:198-211). These mutant proteins can be the target of a tumor specific immune response in multiple types of cancer. Transforming proteins from oncogenic viruses such as E6 and E7 from HPV or EBNA1 from Epstein Barr virus (EBV) also occur in many tumor types and can be the target of a tumor specific immune response in multiple types of cancer (McKaig et al. Head Neck 1998 20(3):250-65; Punwaney et al. Head Neck 1999 21(1):21-9; Serth et al. Cancer Res. 1999 15:59(4):823-5; Pagano, J. S. Proc. Assoc. Am. Physicians 1999 111(6):573-80). Non-oncogenic host proteins such as MAGE and MUC family are also ubiquitous. Specifically, the MAGE family of antigens have been found in many different cancers including breast cancer, lung cancer, esophageal cancer, hepatic cancer, thyroid cancer, neuroblastoma, gastric cancer, multiple myeloma and melanoma (Gillespie, A. M. and Coleman, R. E. Cancer Treat. Rev. 1999 25(4):219-27). The MUC family of antigens has been associated with ovarian and endometrial cancer, breast cancer, multiple myeloma, pancreatic cancer, and colon and rectal cancer (Segal-Eiras, A. and Croce, M. V. Allergol. Immunopathol. 1997 25(4):176-81). As will be obvious to those of skill in the art upon this disclosure, the invention is also applicable to other tumor associated antigens not specifically listed herein.

Further, as demonstrated by these reports, most cancers are associated with more than one antigen. Examples of tumors that express more than one tumor antigen include, but are not limited to, breast cancer which has been shown to be associated with MUC-1, HER-2/neu, MAGE, p53, T/Tn and CEA, colon cancer which has been shown to be associated with MUC-2 and MUC-4, CEA, p53 and the MAGE family, melanoma which has been shown to be associated with members of the MAGE family, MART-1 and gp100, and prostate cancer which has been associated with GM2, Tn, sTn, Thompson-Friedenreich antigen (TF), MUC1, MUC2, the beta chain of human chorionic gonadotropin (hCG beta), HER2/neu, PSMA and PSA. In fact, panels of antigens have been suggested for use in immunotherapy against cancer to compensate for the fact that antigen-loss variants of the tumors can grow out under immune system pressure (Zhang et al. Clin. Cancer Res. 1998 4:2669; Kawashima et al. Hum. Immunol. 1998 59:1). Accordingly, in a preferred embodiment of the present invention, the vaccine comprises a cocktail of recombinant *L. monocytogenes*, each expressing a different tumor associated antigen or a cocktail of fusion proteins, each fusion protein comprising a different tumor associated antigen fused to a truncated form of listeriolysin.

Very stable transformants which secrete a number of large viral proteins have been produced routinely using techniques routine to those of skill in the art. Several techniques for producing recombinant *L. monocytogenes* are known.

For example, integration in the *Listerial* chromosome as a result of a transposon insertion is described by Sun et al. (Infection and Immunity 1990, 58, 3770-3778) in the construction of DP-L967. Transposon mutagenesis has the advantage that a stable genomic insertion mutant can be formed but the disadvantage that the position in the genome where the foreign gene has been inserted is unknown. An *L. monocytogenes* recombinant that expresses E7 was made by chromosomal integration of the E7 gene under the control of the hly promoter and with the inclusion of the hly signal sequence to ensure secretion of the gene product. The site of integration into the chromosome by homologous recombination was into a region that is non-essential for Lm virulence. The resulting recombinant is referred to herein as Lm-AZ/E7.

Figure 9:
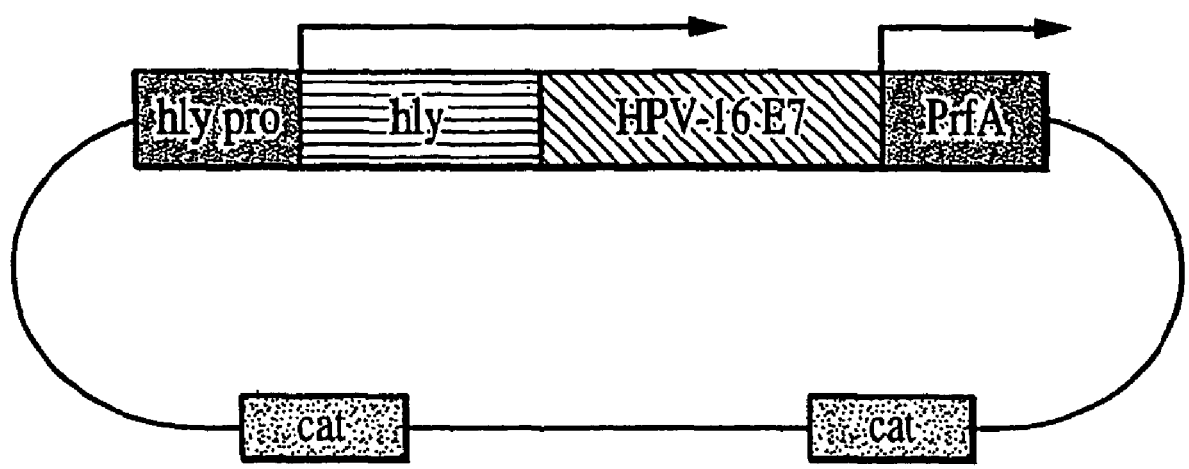
FIG. 9 is a diagram of a preferred multi-copy plasmid containing prfA and E7 fused to hly.

Cloning of the gene into a prfA-containing vector and using this plasmid to complement a prfA(−) *Listeria* mutant has been used to construct DP-L2028. DP-L2028 is the influenza NP expressing strain used in the tumor protection experiments. An *L. monocytogenes* vector that expresses an E7 fusion protein has also been constructed via this technique. Lm-GG/E7 was made by complementing a prfA-deletion mutant with a plasmid (see FIG. 9) containing a copy of the prfA gene and a copy of the E7 gene fused to a form of the LLO (hly) gene truncated to eliminate the hemolytic activity of the enzyme. Functional LLO is maintained by the organism via the endogenous chromosomal copy of hly. Accordingly, the form and level of expression of E7 by the GG construct is identical to Lm-NP.

Several approaches may be taken to express the tumor antigen in *Listeria* sp. as will be understood by one skilled in the art based upon this disclosure. One example is to generate a fusion protein of the selected tumor antigen and a Listerial protein such as Listeriolysin O or PI-PLC. Another way is through the use of a signal sequence, for a secreted Listerial protein such as hemolysin or phospholipases, employed downstream of a *Listerial* promoter. The promoters of various *L. monocytogenes* genes may be used to express foreign antigens. In addition, these genes may be used to generate fusion proteins with foreign antigens. For example, promoters for the genes hly, acta, pica, plcB and mpl, which encode the Listerial proteins hemolysin, actA (a surface protein necessary for host cell actin assembly and essential for cell to cell spread of the bacterium), phosphotidylinositol-specific phospholipase, phospholipase C, and metalloprotease, respectively, can be used.

Another preferred method for producing these recombinants is integration into the *Listeria* chromosome by homologous recombination with a temperature sensitive plasmid. This method can be used to produce stable transformants that secrete the protein of interest. Unlike the case with transposon mutagenesis, the site of insertion is known. This method allows for the routine insertion of any gene of interest into the chromosome of *L. monocytogenes* which is then expressed under the control of a *L. monocytogenes* promoter. One such promoter, the hemolysin promoter, regulates the expression of hly, the *Listerial* gene which encodes LLO, an abundantly synthesized and secreted protein. Inclusion of the LLO signal sequence allows for the secretion of the expressed protein outside the bacterial cell wall. The construction of these stable recombinants of *L. monocytogenes* utilize regions of its chromosome that can act as sites for insertion without disrupting bacterial genes necessary for the growth and spread of the organism (Camilli et al., Mol. Microbiol. 1993, 8, 143157; Weiskirch, L. M. and Paterson, Y. Immunol. Rev. 1997, 158, 159-169). These homology regions are introduced into the shuttle vector pKSV7, a temperature sensitive plasmid that functions in both *E. coli* and *L. monocytogenes*. An EcoR1 site near its center is then used to insert a series of DNA fragments between the two halves of these regions. After the addition of a polylinker, the promoter sequence of the *Listeria* hemolysin. gene is inserted. Along with the promoter, downstream sequence information for the first 26 amino acids of the LLO protein (the signal sequence) and four additional amino acids is included to ensure proper processing of the signal sequence. The transcription termination sequence of the hemolysin gene is also included to ensure that stable and regulated synthesis of all transcripts synthesized. These hemolysin regulatory sequences are used to promote the abundant synthesis and secretion of any adjoining downstream gene.

The vaccines of the present invention can be administered to a host, either alone or in combination with a pharmaceutically acceptable excipient, in an amount sufficient to induce an immune response to a tumor associated antigen. By "host" it is meant to include any organism capable of sustaining cancerous cells, especially a human. By "amount sufficient" it is meant a concentration of one or more recombinant *L. monocytogenes*, each expressing an antigen which invokes an immune response in T cells which will eradicate cells containing this antigen. The recombinant form of *Listeria monocytogenes* can express the tumor associated antigen alone or as a listeriolysin fusion protein which comprises the tumor associated antigen. Alternatively, by "amount sufficient" it is meant a concentration of one or more fusion proteins, each fusion protein comprising an antigen fused to a truncated form of listeriolysin, which invokes an immune response in T cells which will eradicate cells containing this antigen. Such amounts can be routinely determined by one of skill in the art upon this disclosure. By "pharmaceutically acceptable excipient" it is meant to include, but is not limited to, sterile distilled water, saline, phosphate buffered solutions or bicarbonate buffered solutions. The pharmaceutically acceptable excipient selected and the amount of excipient used will depend upon the mode of administration. Administration may be oral, intravenous, parenteral, intranasal, intramuscular, intravascular, intrarectal, intraperitoneal, or any one of a variety of well-known routes of administration. The route of administration may be selected in accordance with the site of different tumors. For example, for treatment of cancers of the alimentary tract, oral administration may be used. For treatment of colorectal cancer, intra-rectal immunization may be used. For the treatment of ovarian or pancreatic cancer, intraperitoneal administration may be used. However, other routes of administration may also be used. The vaccines of the present invention may be administered in the form of elixirs, capsules or suspensions for oral administration or in sterile liquids for parenteral or intravascular administration. The vaccines may be stored frozen, at 4° C., at room temperature or lyophilized.

In a preferred embodiment, the vaccines of the present invention are administered to a host either alone or in combination with another cancer therapy to inhibit or suppress the formation of tumors.

The present invention further encompasses various kits which comprise a compound, including a *Listeria* vaccine strain comprising an antigen fused to a truncated LLO protein, or a fragment thereof, an applicator, and an instructional material which describes use of the compound to perform the methods of the invention. Although model kits are described below, the contents of other useful kits will be apparent to the skilled artisan in light of the present disclosure. Each of these kits is contemplated within the present invention.

In one aspect, the invention includes a kit for treating cancer in a mammal. The kit is used in the same manner as the methods disclosed herein for the present invention. Briefly, the kit may be used to administer an *Listeria* vaccine strain comprising an antigen fused to a truncated LLO protein. Additionally, the kit comprises an applicator and an instructional material for the use of the kit. These instructions simply embody the examples provided herein.

The kit further includes a pharmaceutically-acceptable carrier. The composition is provided in an appropriate amount as set forth elsewhere herein. Further, the route of administration and the frequency of administration are as previously set forth elsewhere herein.

The vaccines of the present invention may be used to protect people at risk for cancer because of familial genetics or other circumstances that predispose them to certain types of cancer, e.g., cervical cancer in women whose husbands have papilloma virus. In addition, the vaccines can used as a cancer immunotherapy after debulking of tumor growth by surgery, conventional chemotherapy or radiation treatment. Following such treatments, the vaccines of the present invention can be administered so that the CTL response to the tumor antigen of the vaccine destroys remaining metastases and prolongs remission from the cancer. It is also believed that the vaccines of the present invention can be used to effect the growth of previously established tumors and to kill existing tumor cells.

EXPERIMENTAL EXAMPLES

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

Construction of a Recombinant *L. monocytogenes* Strain

A sequence encoding the first 420 amino acids of Listeriolysin O (LLO) and its promoter along with some upstream regulatory sequences was PCR amplified from *L. monocytogenes* chromosomal DNA (wild type strain 10403s) and ligated to PCR amplified DNA encoding NP, derived from plasmid pAPR502. (Young, J. F., U. Desselberger, P. Graves, P. Palese and A. Shatzman, "Cloning and Expression of influenza virus genes", The Origin of Pandemic Influenza Viruses, W. G. Layer, eds., Elsevier, N.Y., 1983, p. 129). The construction resulted in an in-frame fusion plus the addition of two amino acids at the site of the fusion junction. The fusion was cloned into the shuttle plasmid pAM401, a shuttle vector able to replicate in both gram+ and gram−bacteria which contains a gram+chloramphenicol resistance gene and a gram−chloramphenicol resistance gene (Wirth, R., F. Y. An and D. B. Clewell, J. Bacteriol. 1986, 165, 831). The resultant plasmid, pDP1659, was introduced into wild type *L. monocytogenes* (strain 10403s) by electroporation to yield *L. monocytogenes* strain DP-L1659. This recombinant strain was clearly able to make and secrete a fusion protein of the predicted size (105 kD) as determined by Western blot analysis of the secreted proteins in the culture supernatants using anti-LLO polyclonal antiserum and anti-NP monoclonal antibody. The presence of the fusion gene under the control of the LLO promoter in a multicopy plasmid resulted in reduced secretion of the chromosomally encoded LLO, but not to the extent that it prevented escape of the bacteria from the vacuole or subsequent intracytoplasmic growth. However, this strain was not stable in the absence of chloramphenicol.

To construct *L. monocytogenes* strain, DP-L2028, which is stable in vivo and which was used in Examples 2 through 6, plasmid pDP-1659 was modified by inserting the prfA gene from 10403s and then used to transform a prfA-*L. monocytogenes* mutant DP-L1075. This resulted in *L. monocytogenes* strain DPL2028 which secretes the LLO-NP fusion protein stably in vivo and in vitro.

Example 2

Treatment of Mice with LM-NP

One hundred and twenty Balb/c mice were divided into three groups of 40. One group was immunized with one-tenth of an LD50 of wild-type *L. monocytogenes*, one group was immunized with sterile saline and the third group was immunized with a recombinant *L. monocytogenes* vector transformed to secrete influenza nucleoprotein fusion protein(LM-NP). After two weeks, each group received a similar booster immunization. This immunization schedule was determined to produce strong CTL responses against influenza nucleoprotein. Two weeks after the last immunization, animals in each group were challenged subcutaneously with either CT26 or RENCA which had been transfected with the same influenza nucleoprotein gene that was used to transform the *L. monocytogenes* vector (CT26-NP or RENCA-NP, respectively) or with the parental CT26 or RENCA line. Each mouse was administered $5 \times 10^5$ tumor cells, which is 50 times the tumoricidal dose. Tumor growth was monitored every two days in these six groups of animals. Results from this study are shown in FIGS. 1 through 4. The only group showing any protection from the tumoricidal dose was the animals which received the LM-NP fusion protein and which were challenged with the relevant tumor cell expressing NP. In the CT26-NP group, after 25 days, 6 of the animals showed no detectable tumor growth, 3 had tumors of less than 5.0 mm and one had a tumor of 9.0 mm. In the RENCA-NP group, none of the animals showed any signs of tumor growth. In contrast, all the mice in the other groups have tumors between 1.5 and 3.0 cm.

In order to maintain the foreign NP gene, CT26-NP is usually maintained on the antibiotic G418. It is believed that the small number of CT26-NP tumor cells that grew in the LM-NP immunized mice are cells which have lost the NP gene in the absence of G418.

Example 3

Figure 5A:
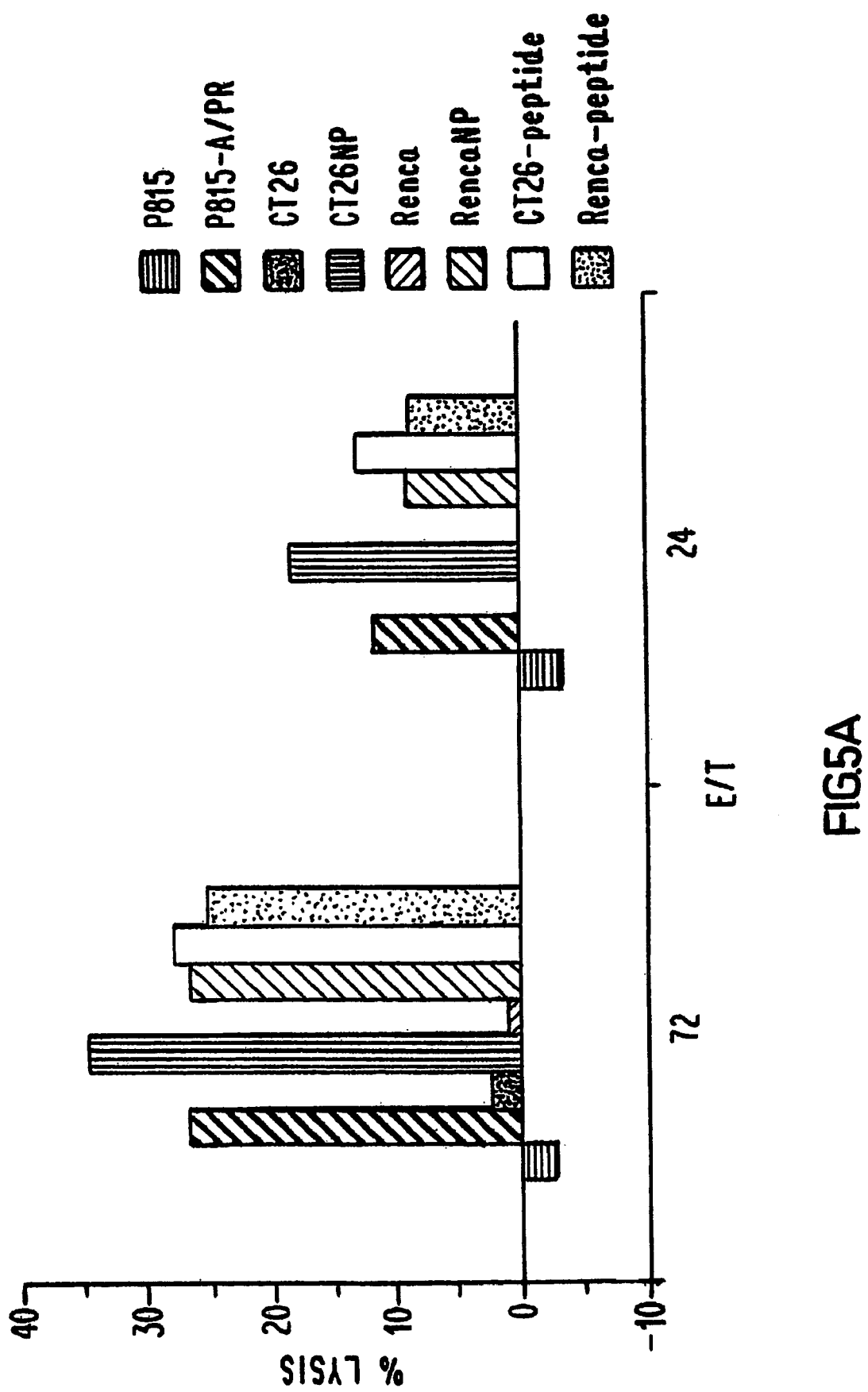
FIG. 5A shows effectors stimulated with A/PR/8.
Figure 5B:
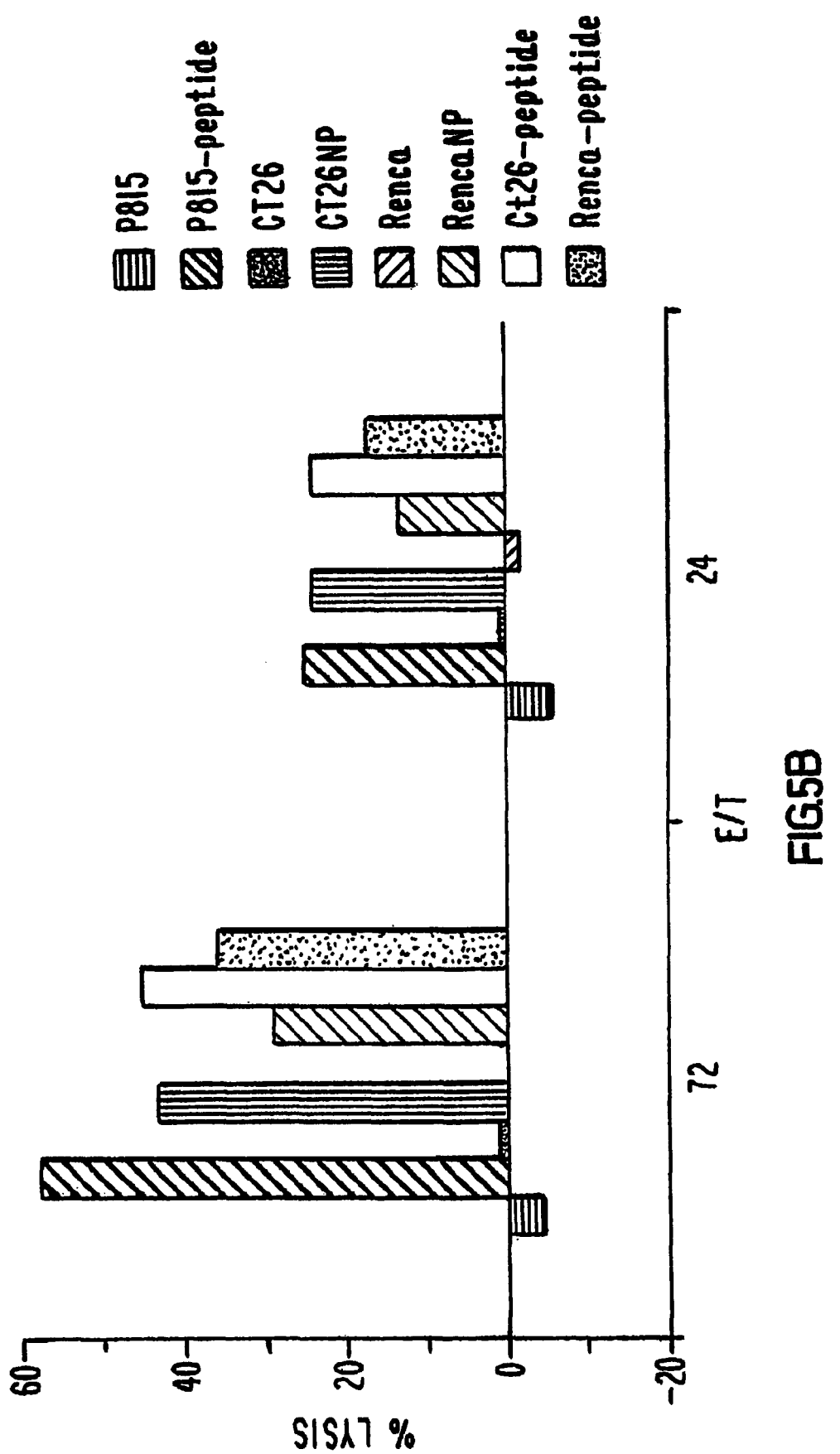
FIG. 5B shows effectors stimulated with peptides.

CTL Generated by Immunizing Balb/c Mice with LM-NP Can Kill Tumor Cells CT26 and RENCA that Express NP In Vitro Mice were immunized with 0.1 $LD_{50}$ of LM-NP. Two weeks later, the mice were sacrificed and primary cultures were set up of spleen cells with either influenza infected (A/PR8/34) splenocytes (FIG. 5A) or with a synthetic peptide 147-158 known to represent the immunodominant epitope of the NP protein (FIG. 5B). After four days in culture, the cytolytic activity of both populations was measured against CT26-NP, RENCA-NP and the parental cell lines CT26 and RENCA. A positive control was included (P815, a mastocytoma tumor cell line known to be efficiently lysed by H-2d restricted CTL in the presence of the peptide or when infected by A/PR8/34). As FIG. 5A shows, RENCA-NP and CT26-NP, but not the parental lines, were lysed by NP specific effectors induced by immunizing with LM-NP and expanded with A/PR8/34. In FIG. 5B, a similar experiment in which the effectors were expanded with peptide show similar results.

Example 4

Immunization by LM-NP Will Cause Elimination of RENCA Tumor Growth

In this experiment, immunization with LM-NP after tumor growth had been initiated caused regression and depletion of tumors. Tumor cells ($5 \times 10^5$) were introduced subcutaneously to 30 mice. On Day 13, after measurable tumors (5 mm) had grown in the mice, they were divided into three groups of ten. Ten mice received LM-NP, 10 mice received wild type *Listeria monocytogenes* and ten received no further treatment. On Day 23 the mice were immunized again with either LM-NP or wild type *Listeria monocytogenes*. As FIG. 6 shows, only the mice that received the LM-NP fusion protein show regression of tumor growth to the point where the tumor was no longer visible in 9 out of 10 mice.

Example 5

Immunization by LM-NP Will Cause Cessation of CT26NP Tumor Growth

The experiment described in Example 4 was also done with the colorectal CT26-NP tumor cells. CT26-NP is a much faster growing tumor and is also more unstable in its expression of NP. Nevertheless, in this experiment, it was also found that immunization by LM-NP after tumor growth has been initiated halts tumor growth. Tumor cells ($5 \times 10^5$) were introduced subcutaneously to 30 mice. On Day 10, after measurable tumors (5 mm) had grown in the mice, they were divided into three groups of ten. Ten mice received LM-NP, 10 mice received wild type *Listeria monocytogenes*, and 10 mice received no further treatment. On Day 17 the mice were immunized again with either LM-NP or wild type *Listeria monocytogenes*. As FIG. 7 shows, only the mice that received the LM-NP fusion protein show a change in tumor growth. However, unlike the case with RENCA, regression of growth was not observed in as many mice. This may be because by Day 17, instability of the CT26-NP tumor cells resulted in many of the tumor cells losing the NP antigen.

Example 6

Inhibition of Tumor Growth is Caused by CD8+ T Cells

Figure 8:
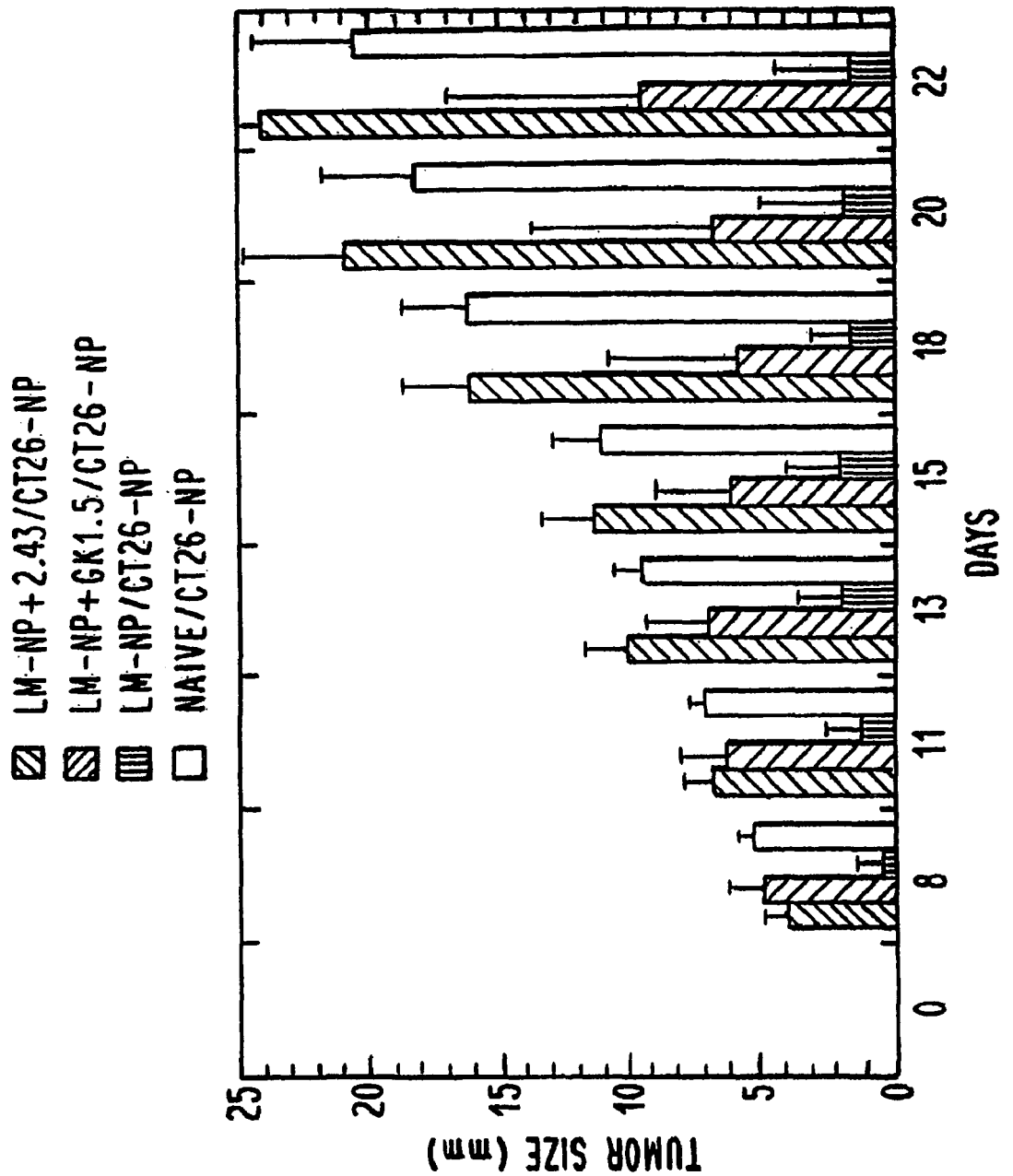
FIG. 8 is a bar graph which provides data from experiments wherein it was shown that inhibition of tumor growth is caused by CD8+ T cells.

In this experiment, 30 mice were immunized with LM-NP using the same protocol as discussed in Example 2. Ten days after the last immunization, 10 mice were depleted of CD8+ cells by immunizing with antibody 2.43 (specific for the CD8 molecule); 10 mice were depleted of CD4+ cells by immunizing with GK-1.5 (specific for the CD4 molecule); and 10 mice were left with a complete T cell repertoire. (The protocol for depletion of CD8+ or CD4+ T cells was that as described by A. Kruisbeek, Current Protocols In Immunology, Coligan et al., eds, John Wiley & Sons, Inc., 1994, V.1, 4.1.1-4.1.2). After T cell depletion, the mice were challenged subcutaneously with $5 \times 10^5$ CT26-NP cells per mouse. As a control, 10 naive mice were also challenged with the same dose. As FIG. 8 shows, the group of mice in which the CD8+ T cell subset was depleted showed similar tumor growth to the control (naive) group of mice. The mice in which the CD4+ T cell subset was depleted showed reduced protection against tumor growth, indicating that CD4+ cells play an accessory response in the control of tumor growth; and the mice with a complete T cell repertoire show protection against tumor growth induced by the LM-NP fusion protein.

Example 7

Expression of Her-2/neu Fragments in *L. monocytogenes*

Three her-2/neu fragments (EC1, EC2 and EC3) cover the extracellular domain of the antigen and two her-2/neu fragments (IC-1 and IC-2) cover the intracellular domain. EC1 is 307 residues, EC2 is 199 residues, EC3 is 177 residues; IC1 is 392 residues and IC2 is 241 residues. The signal sequence and the transmembrane domains were eliminated because highly hydrophobic regions are not easily secreted by *Listeria*.

Figure 10:
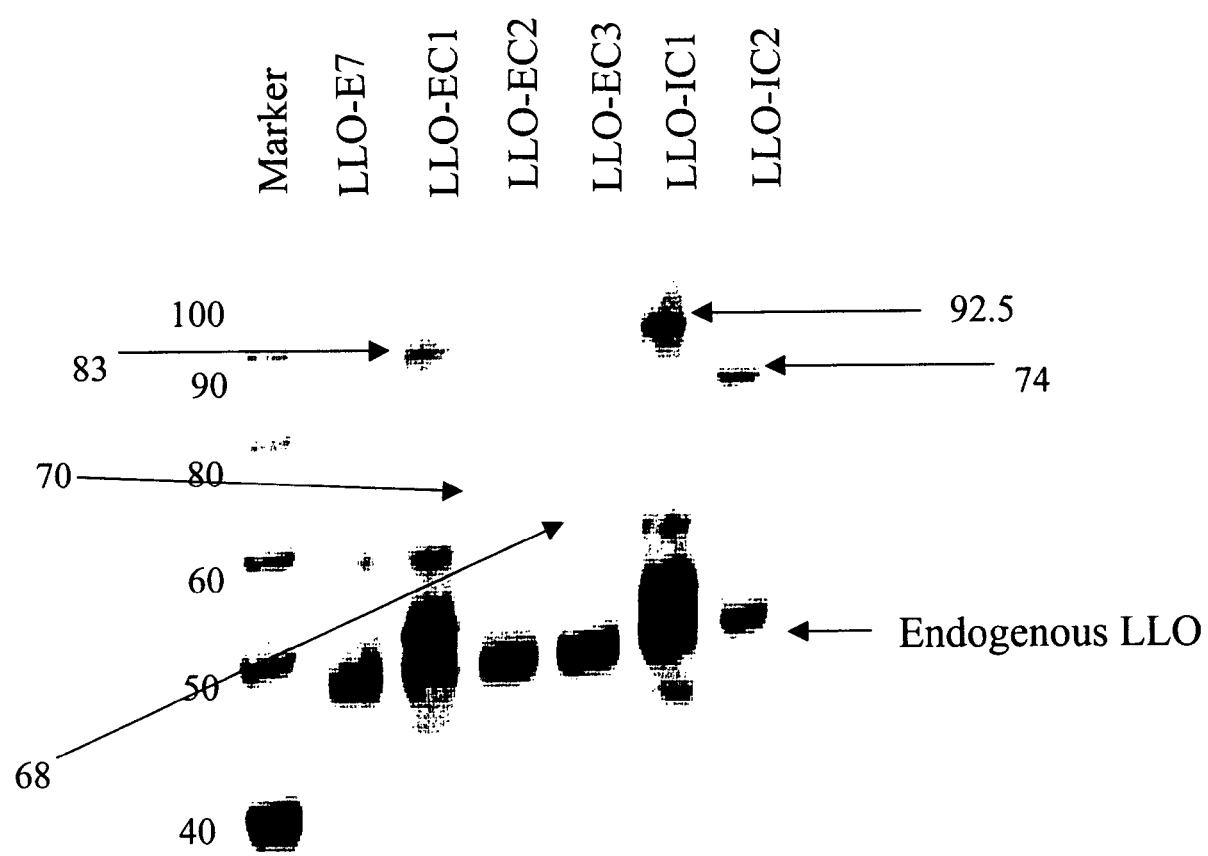
FIG. 10 is an image of a gel depicting the expression of fragments of Her-2/neu fused to a truncated LLO protein expressed from a *Listeria* vaccine strain.

The expression and secretion into culture of each HER-2/neu fragment fused to LLO (LLO-EC1, LLO-EC2, LLO-EC3, LLO-IC1, and LLO-IC2) was confirmed by Western blots of TCA precipitated culture media as described in, for example, Gunn et al., (2001, J. Immunol., 167: 6471-6479). Fusion products were identified by blotting with an antibody raised to the first 30 residues of LLO, which comprises the PEST sequence. This antibody also identifies endogenous LLO secreted by all the *Listeria* vaccines, in addition to the fusion constructs. Fusion products of an appropriate size were expressed and secreted by each *Listeria* vector. Although the amount of antigen secreted varies somewhat between different constructs the intensity of the bands are similar to the LLO-E7 fusion of 58 kD secreted by Lm-LLO-E7 as depicted in FIG. 10.

The $LD_{50}$ of each strain was determined in both FVB and BALB/c mice as depicted in Table 1.

TABLE 1

$LD_{50}$ of Listeria Her-2/neu vaccine strains in FVB and BALB/c mice

| Listeria Strain | $LD_{50}$ |
|---|---|
| Lm-EC1 | $1 \times 10^8$ |
| Lm-EC2 | $1 \times 10^9$ |
| Lm-EC3 | $5 \times 10^8$ |
| Lm-IC1 | $1 \times 10^8$ |
| Lm-IC2 | $1 \times 10^8$ |

Example 8

Induction of Her-2/neu Specific Cytotoxic Lymphocytes

To determine the ability of each of the Lm-HER2/neu constructs to induce HER-2/neu specific cytotoxic T lymphocytes, mice were injected with 0.1 $LD_{50}$ of each vaccine and control mice were injected with 200 µl of phosphate buffered saline (PBS). Nine days later splenocytes were isolated and incubated with NT-2 cells (Reilly et al., 2000, Cancer Res. 60: 3569-3576) as a source of antigen at a ratio of 100 splenocytes to 1 NT-2 cell in 24 well plates with 20 U/ml IL-2 at 37° Celsius. with 5% $CO_2$ for 4 days. NIH-3T3 cells and 3T3-HER-2/neu cells were incubated with $^{51}Cr$. and plated with 100 µl of the cultured splenocytes at the desired effector: target ratios in 96 well flat plates. After 4 hours of incubation at 37° Celsius., released $^{51}Cr$ was measured in a gamma counter and percent specific lysis was calculated as 100% [(experimental−spontaneous)/(total−spontaneous)]. The lysis of 3T3 cells not expressing HER-2/neu was less than 10% for each construct whereas for 3T3 tumor cells expressing HER-2/neu, each Lm-HER-2/neu construct lysed at least 30% of the tumor cells. Thus each Lm-HER-2/neu construct can induce antigen specific CTL.

Example 9

Tumor Growth Control in a Mammalian Tumor Model

A regression experiment was performed to examine the ability of each of these strains to control tumor growth. A mouse tumor that is syngeneic with the FVB/N mouse designated NT-2 (Reilly et al., 2000, Cancer Res. 60: 3569-3576) was used in these experiments. NT-2 has a tumoricidal dose (100% take) of $5 \times 10^6$ in the wild-type FVB/N mouse (Reilly et al., 2000, Cancer Res. 60: 3569-3576). All the Lm-HER-2/neu strains were examined for their ability to induce the regression of established NT-2 in vivo in female FVB mice between the ages of 6-8 weeks. $5 \times 10^6$ NT-2 tumor cells were implanted subcutaneously in each mouse on day 0. When the tumors were palpable (4-5 mm) the mice were vaccinated with 0.1 $LD_{50}$ of each vaccine. Lm-LLO-E7 was included as a vector control. Lm-LLO-E7 is completely isogenic to the HER-2/neu constructs except that it expresses HPV-16 E7. The mice were vaccinated on day 7 and boosted on days 14 and 21.

Figure 11:
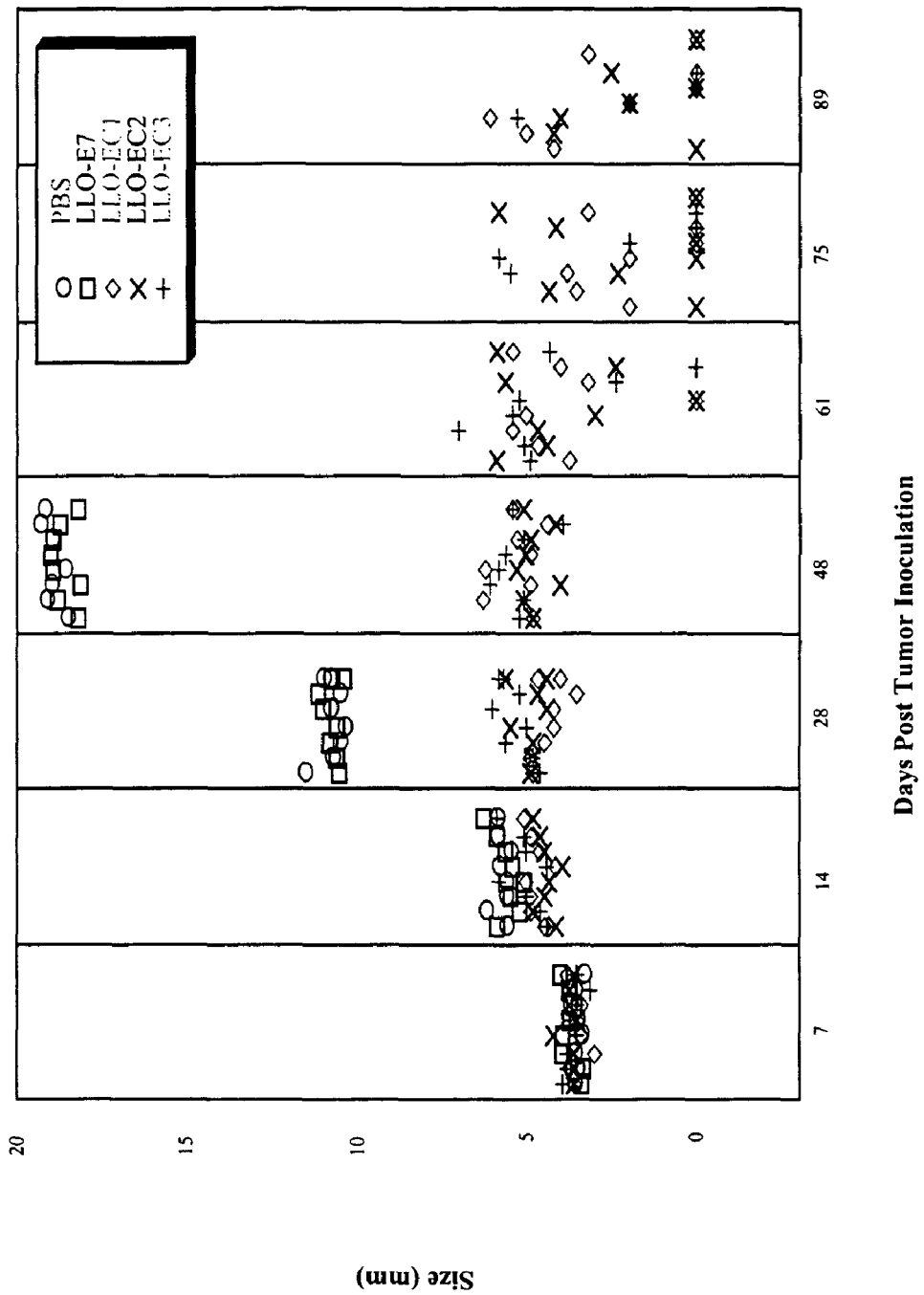
FIG. 11 is an image depicting the tumor size over time in mice with tumors administered a *Listeria* vaccine strain expressing a truncated LLO protein fused to extracellular fragments of Her-2/neu antigen.
Figure 12:
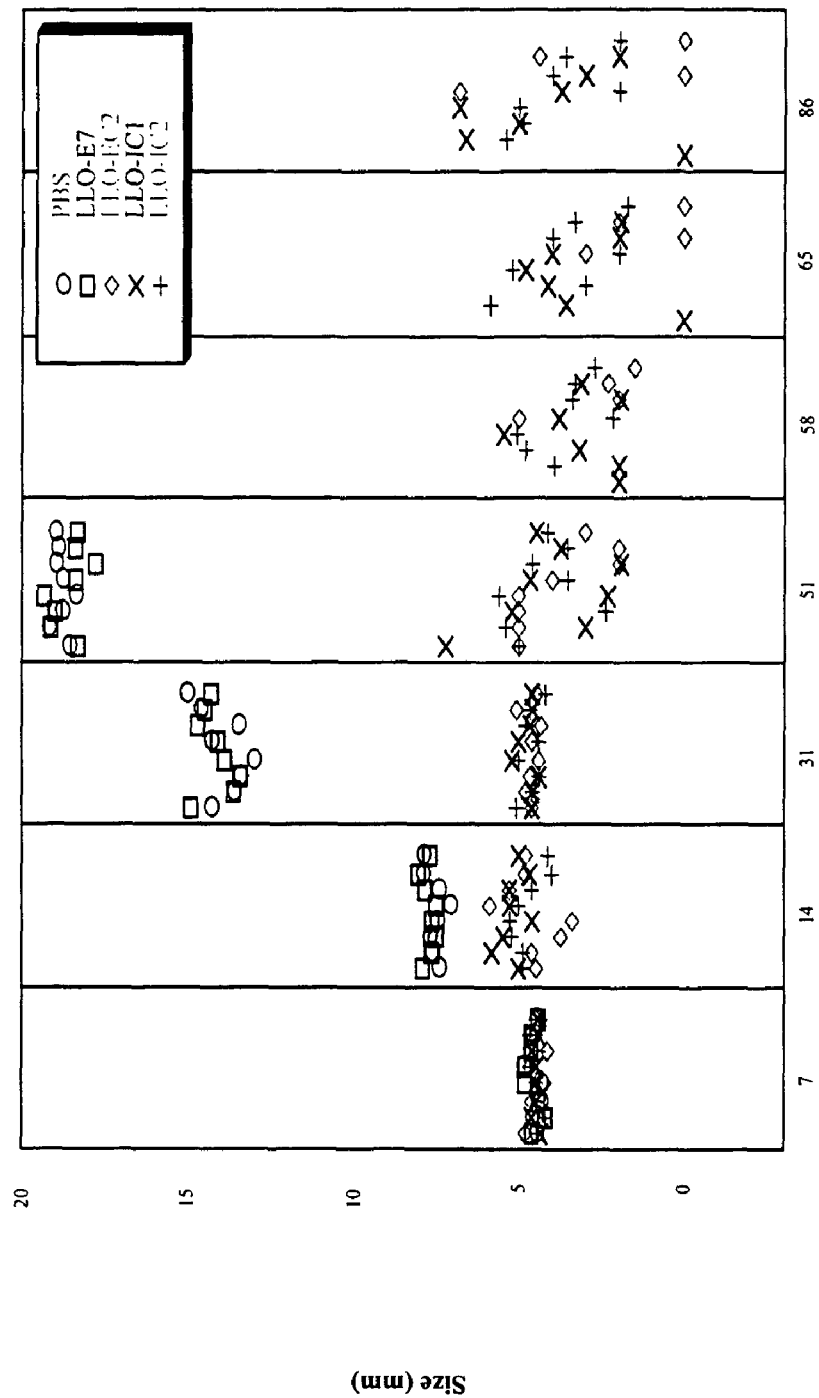
FIG. 12 is an image depicting the tumor size over time in mice with tumors administered a *Listeria* vaccine strain expressing a truncated LLO protein fused to intracellular fragments of Her-2/neu antigen.

All of the control mice had to be sacrificed around about 48 to 51 days following tumor challenge because they had large bulky tumors. In contrast, tumor growth in all of the vaccinated mice was controlled to below 7 mm in diameter and in many mice tumors start to regress at around day 48 to 51. These experiments were terminated at about three months following tumor challenge. The tumors were removed after sacrifice on day 43 and examined to reveal that the tumors totally lacked vascularization and appeared to be largely dead tissue. By this time some of the mice in the vaccinated groups had died of other causes but all showed controlled tumor growth. These experiments demonstrate that all five fragments are effective anti-tumor therapeutics in the FVB mouse and that there does not seem to be much difference in efficacy between the *L. monocytogenes* strains that express the different fragments (FIGS. 11 and 12).

Example 10

Abrogation of Tolerance to a Tumor Antigen

Although the mouse HER-2/neu gene differs from the rat neu by <6% of amino acid residues, there is evidence that rat neu is immunogenic in the mouse (Nagata et al., 1997, J. Immunol. 159: 1336-1343) indicating that the rat HER-2/neu expressing tumors commonly used to test immune strategies may be immunogenic in wild type mice. A transgenic mouse that over expresses rat HER-2/neu under the transcriptional control of the Mouse Mammary Tumor Virus promoter and enhancer has been developed as a model for human breast cancer (Muller, 1991, Cancer Metastasis Rev. 10: 217-227). This mouse is immunologically tolerant to rat HER-2/neu. Thus rat HER-2/neu transgenic mice are a more stringent model to test the ability of immunotherapy to break tolerance against tumor antigens, such as HER-2/neu, that are expressed at low levels in normal tissue.

The HER-2/neu transgenic mouse model was used to evaluate the ability of the present *L. monocytogenes* based cancer vaccines to overcome tolerance to a "self" tumor antigen by examining their ability to induce the regression of established NT-2 in vivo in young, virgin HER-2/neu transgenic mice that have not yet spontaneously developed tumors. For these studies, a lower dose of NT-2 was used because the transgenic mouse is profoundly tolerant to HER-2/neu and thus the tumoricidal dose (100% take) is much lower ($5 \times 10^4$) (Reilly et al., 2000, Cancer Res. 60: 3569-3576). NT-2 cells were injected into the subcutaneous space of the flank of the mouse and animals received 0.1 $LD_{50}$ of the *Listeria* vaccine after 5 mm palpable tumors had grown. Further immunizations were given weekly for 5 weeks starting on day 7 after tumor implantation.

Figure 13:
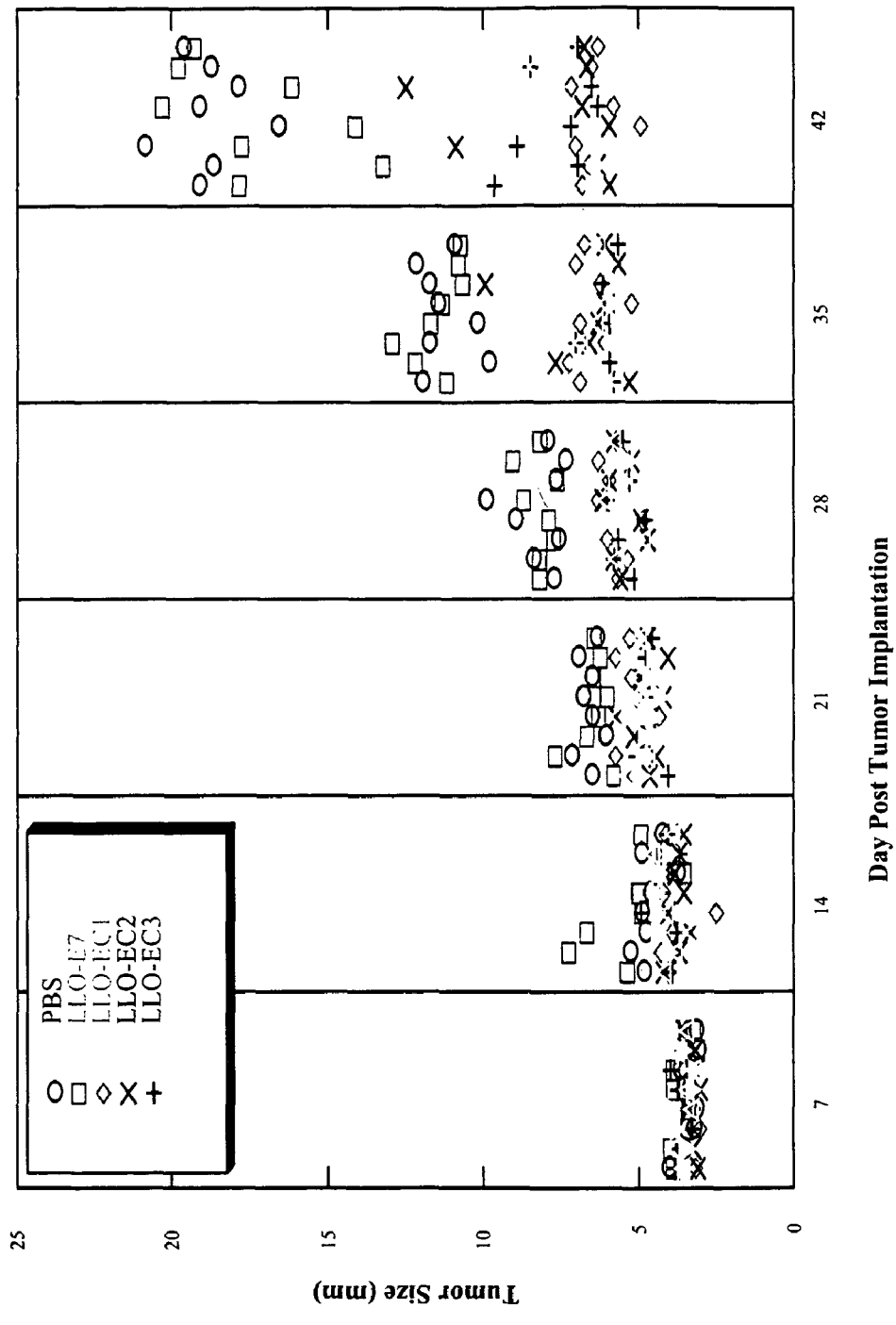
FIG. 13 is an image depicting the tumor size over time in transgenic mice tolerant to tumors expressing Her-2/neu administered a *Listeria* vaccine strain expressing a truncated LLO protein fused to extracellular fragments of Her-2/neu antigen.
Figure 14:
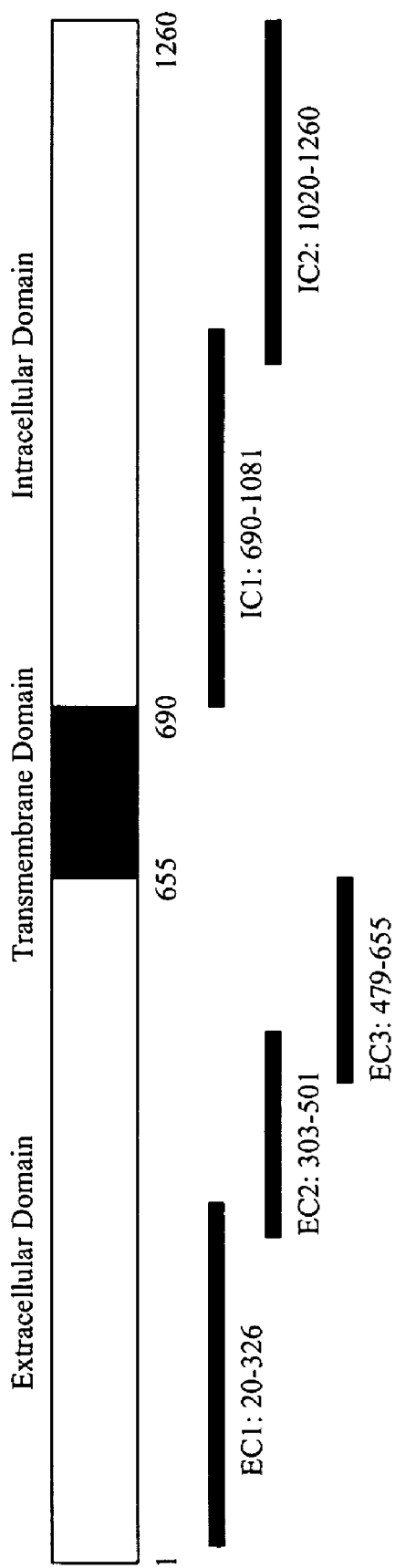
FIG. 14 is a schematic representation of a Her-2/neu antigen depicting the extracellular and intracellular antigen fragments used in a *Listeria* vaccine strain.

Tumor growth was controlled in all of the mice that received the *Listeria* vaccine strains but by day 42 after tumor implantation most of the control mice had to be sacrificed because of their tumor burden. This demonstrates that the five *Listeria monocytogenes* strains are able to break tolerance to HER-2/neu under circumstances where this is a self antigen (FIG. 13).

The disclosures of each and every patent, patent application, and publication cited herein are hereby incorporated by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of treating a breast cancer in a human subject, the method comprising administering to said human subject a *Listeria* vaccine strain, wherein said *Listeria* vaccine strain comprises a nucleic acid encoding a truncated listeriolysin O (LLO) protein fused to a Her-2/neu protein fragment, wherein said truncated LLO protein comprises the sequence set forth in SEQ ID NO: 10 and does not comprise cysteine 484, wherein said Her-2/neu protein fragment consists of amino acid residues selected from the group consisting of SEQ ID NO: 4 and SEQ ID NO: 5 of said Her-2/neu protein, and wherein at least one cell of said breast cancer expresses a Her-2/neu protein, thereby treating a breast cancer in a human subject.

2. The method of claim 1, wherein said *Listeria* vaccine strain is a *Listeria monocytogenes* vaccine strain.

3. The method of claim 1, wherein said truncated LLO protein fused to a Her-2/neu protein fragment is expressed from a plasmid.

4. The method of claim 1, wherein said nucleic acid encoding said truncated LLO protein fused to a Her-2/neu protein fragment is stably integrated into the chromosome of said *Listeria* vaccine strain.

5. The method of claim 1, wherein said vaccine strain is administered intravenously.

6. A method of suppressing tumor formation associated with breast cancer in a human subject, the method comprising administering to said human subject a *Listeria* vaccine strain, wherein said *Listeria* vaccine strain comprises a nucleic acid encoding a truncated listeriolysin O (LLO) protein fused to a Her-2/neu protein fragment, wherein said truncated LLO protein comprises the sequence set forth in SEQ ID NO: 10 and does not comprise cysteine 484, wherein said Her-2/neu protein fragment consists of amino acid residues selected from the group consisting of SEQ ID NO: 4 and SEQ ID NO: 5 of said Her-2/neu protein, and wherein at least one cell of said breast cancer expresses a Her-2/neu protein, thereby treating a breast cancer in a human subject.

7. The method of claim 6, wherein said *Listeria* vaccine strain is a *Listeria monocytogenes* vaccine strain.

8. The method of claim 6, wherein said truncated LLO protein fused to a Her-2/neu protein fragment is expressed from a plasmid.

9. The method of claim 6, wherein said nucleic acid encoding said truncated LLO protein fused to a Her-2/neu protein fragment is stably integrated into the chromosome of said *Listeria* vaccine strain.

10. The method of claim 6, wherein said vaccine strain is administered intravenously.

11. A method of inducing an immune response to a breast cancer in a human subject, the method comprising administering to said human subject a *Listeria* vaccine strain, wherein said *Listeria* vaccine strain comprises a nucleic acid encoding a truncated listeriolysin O (LLO) protein fused to a Her-2/neu protein fragment, wherein said truncated LLO protein comprises the sequence set forth in SEQ ID NO: 10 and does not comprise cysteine 484, wherein said Her-2/neu protein fragment consists of amino acid residues selected from the group consisting of SEQ ID NO: 4 and SEQ ID NO: 5 of said Her-2/neu protein, and wherein at least one cell of said breast cancer expresses a Her-2/neu protein, thereby treating a breast cancer in a human subject.

12. The method of claim 11, wherein said *Listeria* vaccine strain is a *Listeria monocytogenes* vaccine strain.

13. The method of claim 11, wherein said truncated LLO protein fused to a Her-2/neu protein fragment is expressed from a plasmid contained in said *Listeria* vaccine strain.

14. The method of claim 11, wherein said nucleic acid encoding said truncated LLO protein fused to a Her-2/neu protein fragment is stably integrated into the chromosome of said *Listeria* vaccine strain.

15. The method of claim 11, wherein said vaccine strain is administered intraperitoneally.

\* \* \* \* \*

SEQUENCE LISTING

<160> NUMBER OF SEQ ID NOS: 10

<210> SEQ ID NO 1
<211> LENGTH: 1877
<212> TYPE: DNA
<213> ORGANISM: Listeria monocytogenes

<400> SEQUENCE: 1

```
atgaaaaaaa taatgctagt ttttattaca cttatattag ttagtctacc aattgcgcaa      60
caaactgaag caaaggatgc atctgcattc aataaagaaa attcaatttc atccatggca     120
ccaccagcat ctccgcctgc aagtcctaag acgccaatcg aaaagaaaca cgcggatgaa     180
atcgataagt atatacaagg attggattac aataaaaaca atgtattagt ataccacgga     240
gatgcagtga caaatgtgcc gccaagaaaa ggttacaaag atggaaatga atatattgtt     300
gtggagaaaa agaagaaatc catcaatcaa aataatgcag acattcaagt tgtgaatgca     360
atttcgagcc taacctatcc aggtgctctc gtaaaagcga attcggaatt agtagaaaat     420
caaccagatg ttctccctgt aaaacgtgat tcattaacac tcagcattga tttgccaggt     480
atgactaatc aagacaataa aatcgttgta aaaaatgcca ctaaatcaaa cgttaacaac     540
gcagtaaata cattagtgga agatggaat gaaaatatg ctcaagctta tccaaatgta     600
agtgcaaaaa ttgattatga tgacgaaatg gcttacagtg aatcacaatt aattgcgaaa     660
tttggtacag catttaaagc tgtaaataat agcttgaatg taaacttcgg cgcaatcagt     720
gaagggaaaa tgcaagaaga agtcattagt tttaaacaaa tttactataa cgtgaatgtt     780
aatgaaccta caagaccttc cagattttc ggcaaagctg ttactaaaga gcagttgcaa     840
gcgcttggag tgaatgcaga aatcctcct gcatatatct caagtgtggc gtatggccgt     900
caagtttatt tgaaattatc aactaattcc catagtacta aagtaaaagc tgcttttgat     960
gctgccgtaa gcggaaaatc tgtctcaggt gatgtagaac taacaaatat catcaaaaat    1020
tcttccttca aagccgtaat ttacggaggt tccgcaaaag atgaagttca aatcatcgac    1080
ggcaacctcg gagacttacg cgatattttg aaaaaggcg ctacttttaa tcgagaaaca    1140
ccaggagttc ccattgctta tacaacaaac ttcctaaaag acaatgaatt agctgttatt    1200
aaaaacaact cagaatatat tgaaacaact tcaaaagctt atacagatgg aaaaattaac    1260
atcgatcact ctggaggata cgttgctcaa ttcaacattt cttgggatga agtaaattat    1320
gatcctgaag gtaacgaaat tgttcaacat aaaaactgga gcgaaaacaa taaaagcaag    1380
ctagctcatt tcacatcgtc catctatttg ccaggtaacg cgagaaatat taatgtttac    1440
gctaaagaat gcactggttt agcttgggaa tggtggagaa cggtaattga tgaccggaac    1500
ttaccacttg tgaaaaatag aaatatctcc atctggggca ccacgcttta tccgaaatat    1560
agtaataaag tagataatcc aatcgaataa ttgtaaaagt aataaaaaat taagaataaa    1620
accgcttaac acacacgaaa aaataagctt gttttgcact cttcgtaaat tattttgtga    1680
agaatgtaga aacaggctta ttttttaatt tttttagaag aattaacaaa tgtaaaagaa    1740
```

-continued

```
tatctgactg tttatccata taatataagc atatcccaaa gtttaagcca cctatagttt    1800
ctactgcaaa acgtataatt tagttcccac atatactaaa aaacgtgtcc ttaactctct    1860
ctgtcagatt agttgta                                                   1877
```

<210> SEQ ID NO 2
<211> LENGTH: 529
<212> TYPE: PRT
<213> ORGANISM: Listeria monocytogenes

<400> SEQUENCE: 2

```
Met Lys Lys Ile Met Leu Val Phe Ile Thr Leu Ile Leu Val Ser Leu
1               5                   10                  15

Pro Ile Ala Gln Gln Thr Glu Ala Lys Asp Ala Ser Ala Phe Asn Lys
            20                  25                  30

Glu Asn Ser Ile Ser Ser Met Ala Pro Pro Ala Ser Pro Pro Ala Ser
        35                  40                  45

Pro Lys Thr Pro Ile Glu Lys Lys His Ala Asp Glu Ile Asp Lys Tyr
    50                  55                  60

Ile Gln Gly Leu Asp Tyr Asn Lys Asn Asn Val Leu Val Tyr His Gly
65                  70                  75                  80

Asp Ala Val Thr Asn Val Pro Pro Arg Lys Gly Tyr Lys Asp Gly Asn
                85                  90                  95

Glu Tyr Ile Val Val Glu Lys Lys Lys Ser Ile Asn Gln Asn Asn
            100                 105                 110

Ala Asp Ile Gln Val Val Asn Ala Ile Ser Ser Leu Thr Tyr Pro Gly
        115                 120                 125

Ala Leu Val Lys Ala Asn Ser Glu Leu Val Glu Asn Gln Pro Asp Val
    130                 135                 140

Leu Pro Val Lys Arg Asp Ser Leu Thr Leu Ser Ile Asp Leu Pro Gly
145                 150                 155                 160

Met Thr Asn Gln Asp Asn Lys Ile Val Val Lys Asn Ala Thr Lys Ser
                165                 170                 175

Asn Val Asn Asn Ala Val Asn Thr Leu Val Glu Arg Trp Asn Glu Lys
            180                 185                 190

Tyr Ala Gln Ala Tyr Pro Asn Val Ser Ala Lys Ile Asp Tyr Asp Asp
        195                 200                 205

Glu Met Ala Tyr Ser Glu Ser Gln Leu Ile Ala Lys Phe Gly Thr Ala
    210                 215                 220

Phe Lys Ala Val Asn Asn Ser Leu Asn Val Asn Phe Gly Ala Ile Ser
225                 230                 235                 240

Glu Gly Lys Met Gln Glu Glu Val Ile Ser Phe Lys Gln Ile Tyr Tyr
                245                 250                 255

Asn Val Asn Val Asn Glu Pro Thr Arg Pro Ser Arg Phe Phe Gly Lys
            260                 265                 270

Ala Val Thr Lys Glu Gln Leu Gln Ala Leu Gly Val Asn Ala Glu Asn
        275                 280                 285

Pro Pro Ala Tyr Ile Ser Ser Val Ala Tyr Gly Arg Gln Val Tyr Leu
    290                 295                 300

Lys Leu Ser Thr Asn Ser His Ser Thr Lys Val Lys Ala Ala Phe Asp
305                 310                 315                 320

Ala Ala Val Ser Gly Lys Ser Val Ser Gly Asp Val Glu Leu Thr Asn
                325                 330                 335

Ile Ile Lys Asn Ser Ser Phe Lys Ala Val Ile Tyr Gly Gly Ser Ala
```

-continued

```
                340                 345                 350
Lys Asp Glu Val Gln Ile Ile Asp Gly Asn Leu Gly Asp Leu Arg Asp
            355                 360                 365

Ile Leu Lys Lys Gly Ala Thr Phe Asn Arg Glu Thr Pro Gly Val Pro
        370                 375                 380

Ile Ala Tyr Thr Thr Asn Phe Leu Lys Asp Asn Glu Leu Ala Val Ile
385                 390                 395                 400

Lys Asn Asn Ser Glu Tyr Ile Glu Thr Thr Ser Lys Ala Tyr Thr Asp
                405                 410                 415

Gly Lys Ile Asn Ile Asp His Ser Gly Gly Tyr Val Ala Gln Phe Asn
            420                 425                 430

Ile Ser Trp Asp Glu Val Asn Tyr Asp Pro Glu Gly Asn Glu Ile Val
        435                 440                 445

Gln His Lys Asn Trp Ser Glu Asn Asn Lys Ser Lys Leu Ala His Phe
    450                 455                 460

Thr Ser Ser Ile Tyr Leu Pro Gly Asn Ala Arg Asn Ile Asn Val Tyr
465                 470                 475                 480

Ala Lys Glu Cys Thr Gly Leu Ala Trp Glu Trp Trp Arg Thr Val Ile
                485                 490                 495

Asp Asp Arg Asn Leu Pro Leu Val Lys Asn Arg Asn Ile Ser Ile Trp
            500                 505                 510

Gly Thr Thr Leu Tyr Pro Lys Tyr Ser Asn Lys Val Asp Asn Pro Ile
        515                 520                 525

Glu

<210> SEQ ID NO 3
<211> LENGTH: 307
<212> TYPE: PRT
<213> ORGANISM: Rattus norvegicus

<400> SEQUENCE: 3

Pro Pro Gly Ile Ala Gly Thr Gln Val Cys Thr Gly Thr Asp Met Lys
1               5                   10                  15

Leu Arg Leu Pro Ala Ser Pro Glu Thr His Leu Asp Met Leu Arg His
            20                  25                  30

Leu Tyr Gln Gly Cys Gln Val Val Gln Gly Asn Leu Glu Leu Thr Tyr
        35                  40                  45

Val Pro Ala Asn Ala Ser Leu Ser Phe Leu Gln Asp Ile Gln Glu Val
    50                  55                  60

Gln Gly Tyr Met Leu Ile Ala His Asn Gln Val Lys Arg Val Pro Leu
65                  70                  75                  80

Gln Arg Leu Arg Ile Val Arg Gly Thr Gln Leu Phe Glu Asp Lys Tyr
                85                  90                  95

Ala Leu Ala Val Leu Asp Asn Arg Asp Pro Gln Asp Asn Val Ala Ala
            100                 105                 110

Ser Thr Pro Gly Arg Thr Pro Glu Gly Leu Arg Glu Leu Gln Leu Arg
        115                 120                 125

Ser Leu Thr Glu Ile Leu Lys Gly Gly Val Leu Ile Arg Gly Asn Pro
    130                 135                 140

Gln Leu Cys Tyr Gln Asp Met Val Leu Trp Lys Asp Val Phe Arg Lys
145                 150                 155                 160

Asn Asn Gln Leu Ala Pro Val Asp Ile Asp Thr Asn Arg Ser Arg Ala
                165                 170                 175

Cys Pro Pro Cys Ala Pro Ala Cys Lys Asp Asn His Cys Trp Gly Glu
```

```
              180                 185                 190
Ser Pro Glu Asp Cys Gln Ile Leu Thr Gly Thr Ile Cys Thr Ser Gly
        195                 200                 205

Cys Ala Arg Cys Lys Gly Arg Leu Pro Thr Asp Cys Cys His Glu Gln
        210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met His Asn Pro Glu Gly
        260                 265                 270

Arg Tyr Thr Phe Gly Ala Ser Cys Val Thr Thr Cys Pro Tyr Asn Tyr
        275                 280                 285

Leu Ser Thr Glu Val Gly Ser Cys Thr Leu Val Cys Pro Pro Asn Asn
        290                 295                 300

Gln Glu Val
305

<210> SEQ ID NO 4
<211> LENGTH: 199
<212> TYPE: PRT
<213> ORGANISM: Rattus norvegicus

<400> SEQUENCE: 4

Cys Pro Tyr Asn Tyr Leu Ser Thr Glu Val Gly Ser Cys Thr Leu Val
1               5                   10                  15

Cys Pro Pro Asn Asn Gln Glu Val Thr Ala Glu Asp Gly Thr Gln Arg
            20                  25                  30

Cys Glu Lys Cys Ser Lys Pro Cys Ala Arg Val Cys Tyr Gly Leu Gly
        35                  40                  45

Met Glu His Leu Arg Gly Ala Arg Ala Ile Thr Ser Asp Asn Val Gln
    50                  55                  60

Glu Phe Asp Gly Cys Lys Lys Ile Phe Gly Ser Leu Ala Phe Leu Pro
65                  70                  75                  80

Glu Ser Phe Asp Gly Asp Pro Ser Ser Gly Ile Ala Pro Leu Arg Pro
                85                  90                  95

Glu Gln Leu Gln Val Phe Glu Thr Leu Glu Glu Ile Thr Gly Tyr Leu
            100                 105                 110

Tyr Ile Ser Ala Trp Pro Asp Ser Leu Arg Asp Leu Ser Val Phe Gln
        115                 120                 125

Asn Leu Arg Ile Ile Arg Gly Arg Ile Leu His Asp Gly Ala Tyr Ser
    130                 135                 140

Leu Thr Leu Gln Gly Leu Gly Ile His Ser Leu Gly Leu Arg Ser Leu
145                 150                 155                 160

Arg Glu Leu Gly Ser Gly Leu Ala Leu Ile His Arg Asn Ala His Leu
                165                 170                 175

Cys Phe Val His Thr Val Pro Trp Asp Gln Leu Phe Arg Asn Pro His
            180                 185                 190

Gln Ala Leu Leu His Ser Gly
        195

<210> SEQ ID NO 5
<211> LENGTH: 177
<212> TYPE: PRT
<213> ORGANISM: Rattus norvegicus
```

-continued

```
<400> SEQUENCE: 5

Cys Phe Val His Thr Val Pro Trp Asp Gln Leu Phe Arg Asn Pro His
 1               5                  10                  15

Gln Ala Leu Leu His Ser Gly Asn Arg Pro Glu Glu Asp Leu Cys Val
            20                  25                  30

Ser Ser Gly Leu Val Cys Asn Ser Leu Cys Ala His Gly His Cys Trp
        35                  40                  45

Gly Pro Gly Pro Thr Gln Cys Val Asn Cys Ser His Phe Leu Arg Gly
    50                  55                  60

Gln Glu Cys Val Glu Cys Arg Val Trp Lys Gly Leu Pro Arg Glu
65                  70                  75                  80

Tyr Val Ser Asp Lys Arg Cys Leu Pro Cys His Pro Glu Cys Gln Pro
                85                  90                  95

Gln Asn Ser Ser Glu Thr Cys Phe Gly Ser Glu Ala Asp Gln Cys Ala
            100                 105                 110

Ala Cys Ala His Tyr Lys Asp Ser Ser Cys Val Ala Arg Cys Pro
        115                 120                 125

Ser Gly Val Lys Pro Asp Leu Ser Tyr Met Pro Ile Trp Lys Tyr Pro
    130                 135                 140

Asp Glu Glu Gly Ile Cys Gln Pro Cys Pro Ile Asn Cys Thr His Ser
145                 150                 155                 160

Cys Val Asp Leu Asp Glu Arg Gly Cys Pro Ala Glu Gln Arg Ala Ser
                165                 170                 175

Pro

<210> SEQ ID NO 6
<211> LENGTH: 391
<212> TYPE: PRT
<213> ORGANISM: Rattus norvegicus

<400> SEQUENCE: 6

Thr Met Arg Arg Leu Leu Gln Glu Thr Glu Leu Val Glu Pro Leu Thr
 1               5                  10                  15

Pro Ser Gly Ala Met Pro Asn Gln Ala Gln Met Arg Ile Leu Lys Glu
            20                  25                  30

Thr Glu Leu Arg Lys Val Lys Val Leu Gly Ser Gly Ala Phe Gly Thr
        35                  40                  45

Val Tyr Lys Gly Ile Trp Ile Pro Asp Gly Glu Asn Val Lys Ile Pro
    50                  55                  60

Val Ala Ile Lys Val Leu Arg Glu Asn Thr Ser Pro Lys Ala Asn Lys
65                  70                  75                  80

Glu Ile Leu Asp Glu Ala Tyr Val Met Ala Gly Val Gly Ser Pro Tyr
                85                  90                  95

Val Ser Arg Leu Leu Gly Ile Cys Leu Thr Ser Thr Val Gln Leu Val
            100                 105                 110

Thr Gln Leu Met Pro Tyr Gly Cys Leu Leu Asp His Val Arg Glu His
        115                 120                 125

Arg Gly Arg Leu Gly Ser Gln Asp Leu Leu Asn Trp Cys Val Gln Ile
    130                 135                 140

Ala Lys Gly Met Ser Tyr Leu Glu Asp Val Arg Leu Val His Arg Asp
145                 150                 155                 160

Leu Ala Ala Arg Asn Val Leu Val Lys Ser Pro Asn His Val Lys Ile
                165                 170                 175

Thr Asp Phe Gly Leu Ala Arg Leu Leu Asp Ile Asp Glu Thr Glu Tyr
```

-continued

```
                180                 185                 190
His Ala Asp Gly Gly Lys Val Pro Ile Lys Trp Met Ala Leu Glu Ser
            195                 200                 205

Ile Leu Arg Arg Arg Phe Thr His Gln Ser Asp Val Trp Ser Tyr Gly
        210                 215                 220

Val Thr Val Trp Glu Leu Met Thr Phe Gly Ala Lys Pro Tyr Asp Gly
225                 230                 235                 240

Ile Pro Ala Arg Glu Ile Pro Asp Leu Leu Glu Lys Gly Glu Arg Leu
                245                 250                 255

Pro Gln Pro Pro Ile Cys Thr Ile Asp Val Tyr Met Ile Met Val Lys
            260                 265                 270

Cys Trp Met Ile Asp Ser Glu Cys Arg Pro Arg Phe Arg Glu Leu Val
        275                 280                 285

Ser Glu Phe Ser Arg Met Ala Arg Asp Pro Gln Arg Phe Val Val Ile
    290                 295                 300

Gln Asn Glu Asp Leu Gly Pro Ser Ser Pro Met Asp Ser Thr Phe Tyr
305                 310                 315                 320

Arg Ser Leu Leu Glu Asp Asp Asp Met Gly Asp Leu Val Asp Ala Glu
                325                 330                 335

Glu Tyr Leu Val Pro Gln Gln Gly Phe Phe Ser Pro Asp Pro Thr Pro
            340                 345                 350

Gly Thr Gly Ser Thr Ala His Arg Arg His Arg Ser Ser Ser Thr Arg
        355                 360                 365

Ser Gly Gly Gly Glu Leu Thr Leu Gly Leu Glu Pro Ser Glu Glu Gly
    370                 375                 380

Pro Pro Arg Ser Pro Leu Ala
385                 390

<210> SEQ ID NO 7
<211> LENGTH: 241
<212> TYPE: PRT
<213> ORGANISM: Rattus norvegicus

<400> SEQUENCE: 7

Gly Asp Leu Val Asp Ala Glu Glu Tyr Leu Val Pro Gln Gln Gly Phe
1               5                   10                  15

Phe Ser Pro Asp Pro Thr Pro Gly Thr Gly Ser Thr Ala His Arg Arg
            20                  25                  30

His Arg Ser Ser Ser Thr Arg Ser Gly Gly Gly Glu Leu Thr Leu Gly
        35                  40                  45

Leu Glu Pro Ser Glu Glu Gly Pro Pro Arg Ser Pro Leu Ala Pro Ser
    50                  55                  60

Glu Gly Ala Gly Ser Asp Val Phe Asp Gly Asp Leu Ala Met Gly Val
65                  70                  75                  80

Thr Lys Gly Leu Gln Ser Leu Ser Pro His Asp Leu Ser Pro Leu Gln
                85                  90                  95

Arg Tyr Ser Glu Asp Pro Thr Leu Pro Leu Pro Pro Glu Thr Asp Gly
            100                 105                 110

Tyr Val Ala Pro Leu Ala Cys Ser Pro Gln Pro Glu Tyr Val Asn Gln
        115                 120                 125

Ser Glu Val Gln Pro Gln Pro Pro Leu Thr Pro Glu Gly Pro Leu Pro
    130                 135                 140

Pro Val Arg Pro Ala Gly Ala Thr Leu Glu Arg Pro Lys Thr Leu Ser
145                 150                 155                 160
```

```
Pro Gly Lys Asn Gly Val Val Lys Asp Val Phe Ala Phe Gly Gly Ala
            165                 170                 175

Val Glu Asn Pro Glu Tyr Leu Val Pro Arg Glu Gly Thr Ala Ser Pro
            180                 185                 190

Pro His Pro Ser Pro Ala Phe Ser Pro Ala Phe Asp Asn Leu Tyr Tyr
            195                 200                 205

Trp Asp Gln Asn Ser Ser Glu Gln Gly Pro Pro Ser Asn Phe Glu
210                 215                 220

Gly Thr Pro Thr Ala Glu Asn Pro Glu Tyr Leu Gly Leu Asp Val Pro
225                 230                 235                 240

Val

<210> SEQ ID NO 8
<211> LENGTH: 1260
<212> TYPE: PRT
<213> ORGANISM: Rattus norvegicus

<400> SEQUENCE: 8

Met Ile Ile Met Glu Leu Ala Ala Trp Cys Arg Trp Gly Phe Leu Leu
1               5                   10                  15

Ala Leu Leu Pro Pro Gly Ile Ala Gly Thr Gln Val Cys Thr Gly Thr
            20                  25                  30

Asp Met Lys Leu Arg Leu Pro Ala Ser Pro Glu Thr His Leu Asp Met
            35                  40                  45

Leu Arg His Leu Tyr Gln Gly Cys Gln Val Val Gln Gly Asn Leu Glu
        50                  55                  60

Leu Thr Tyr Val Pro Ala Asn Ala Ser Leu Ser Phe Leu Gln Asp Ile
65                  70                  75                  80

Gln Glu Val Gln Gly Tyr Met Leu Ile Ala His Asn Gln Val Lys Arg
                85                  90                  95

Val Pro Leu Gln Arg Leu Arg Ile Val Arg Gly Thr Gln Leu Phe Glu
            100                 105                 110

Asp Lys Tyr Ala Leu Ala Val Leu Asp Asn Arg Asp Pro Gln Asp Asn
            115                 120                 125

Val Ala Ala Ser Thr Pro Gly Arg Thr Pro Glu Gly Leu Arg Glu Leu
        130                 135                 140

Gln Leu Arg Ser Leu Thr Glu Ile Leu Lys Gly Gly Val Leu Ile Arg
145                 150                 155                 160

Gly Asn Pro Gln Leu Cys Tyr Gln Asp Met Val Leu Trp Lys Asp Val
                165                 170                 175

Phe Arg Lys Asn Asn Gln Leu Ala Pro Val Asp Ile Asp Thr Asn Arg
            180                 185                 190

Ser Arg Ala Cys Pro Pro Cys Ala Pro Ala Cys Lys Asp Asn His Cys
        195                 200                 205

Trp Gly Glu Ser Pro Glu Asp Cys Gln Ile Leu Thr Gly Thr Ile Cys
    210                 215                 220

Thr Ser Gly Cys Ala Arg Cys Lys Gly Arg Leu Pro Thr Asp Cys Cys
225                 230                 235                 240

His Glu Gln Cys Ala Ala Gly Cys Thr Gly Pro Lys His Ser Asp Cys
                245                 250                 255

Leu Ala Cys Leu His Phe Asn His Ser Gly Ile Cys Glu Leu His Cys
            260                 265                 270

Pro Ala Leu Val Thr Tyr Asn Thr Asp Thr Phe Glu Ser Met His Asn
        275                 280                 285
```

-continued

| | | | | | | | | | | | |
|---|---|---|---|---|---|---|---|---|---|---|---|
|Pro|Glu|Gly|Arg|Tyr|Thr|Phe|Gly|Ala|Ser|Cys|Val|Thr|Thr|Cys|Pro|
| |290| | | |295| | | |300| | | | | | |

Tyr Asn Tyr Leu Ser Thr Glu Val Gly Ser Cys Thr Leu Val Cys Pro
305                 310                 315                 320

Pro Asn Asn Gln Glu Val Thr Ala Glu Asp Gly Thr Gln Arg Cys Glu
            325                 330                 335

Lys Cys Ser Lys Pro Cys Ala Arg Val Cys Tyr Gly Leu Gly Met Glu
        340                 345                 350

His Leu Arg Gly Ala Arg Ala Ile Thr Ser Asp Asn Val Gln Glu Phe
    355                 360                 365

Asp Gly Cys Lys Lys Ile Phe Gly Ser Leu Ala Phe Leu Pro Glu Ser
370                 375                 380

Phe Asp Gly Asp Pro Ser Ser Gly Ile Ala Pro Leu Arg Pro Glu Gln
385                 390                 395                 400

Leu Gln Val Phe Glu Thr Leu Glu Glu Ile Thr Gly Tyr Leu Tyr Ile
            405                 410                 415

Ser Ala Trp Pro Asp Ser Leu Arg Asp Leu Ser Val Phe Gln Asn Leu
            420                 425                 430

Arg Ile Ile Arg Gly Arg Ile Leu His Asp Gly Ala Tyr Ser Leu Thr
            435                 440                 445

Leu Gln Gly Leu Gly Ile His Ser Leu Gly Leu Arg Ser Leu Arg Glu
        450                 455                 460

Leu Gly Ser Gly Leu Ala Leu Ile His Arg Asn Ala His Leu Cys Phe
465                 470                 475                 480

Val His Thr Val Pro Trp Asp Gln Leu Phe Arg Asn Pro His Gln Ala
            485                 490                 495

Leu Leu His Ser Gly Asn Arg Pro Glu Glu Asp Leu Cys Val Ser Ser
        500                 505                 510

Gly Leu Val Cys Asn Ser Leu Cys Ala His Gly His Cys Trp Gly Pro
    515                 520                 525

Gly Pro Thr Gln Cys Val Asn Cys Ser His Phe Leu Arg Gly Gln Glu
530                 535                 540

Cys Val Glu Glu Cys Arg Val Trp Lys Gly Leu Pro Arg Glu Tyr Val
545                 550                 555                 560

Ser Asp Lys Arg Cys Leu Pro Cys His Pro Glu Cys Gln Pro Gln Asn
            565                 570                 575

Ser Ser Glu Thr Cys Phe Gly Ser Glu Ala Asp Gln Cys Ala Ala Cys
        580                 585                 590

Ala His Tyr Lys Asp Ser Ser Ser Cys Val Ala Arg Cys Pro Ser Gly
    595                 600                 605

Val Lys Pro Asp Leu Ser Tyr Met Pro Ile Trp Lys Tyr Pro Asp Glu
610                 615                 620

Glu Gly Ile Cys Gln Pro Cys Pro Ile Asn Cys Thr His Ser Cys Val
625                 630                 635                 640

Asp Leu Asp Glu Arg Gly Cys Pro Ala Glu Gln Arg Ala Ser Pro Val
            645                 650                 655

Thr Phe Ile Ile Ala Thr Val Glu Gly Val Leu Leu Phe Leu Ile Leu
        660                 665                 670

Val Val Val Val Gly Ile Leu Ile Lys Arg Arg Gln Lys Ile Arg
    675                 680                 685

Lys Tyr Thr Met Arg Arg Leu Leu Gln Glu Thr Glu Leu Val Glu Pro
690                 695                 700

Leu Thr Pro Ser Gly Ala Met Pro Asn Gln Ala Gln Met Arg Ile Leu

-continued

```
            705                 710                 715                 720
Lys Glu Thr Glu Leu Arg Lys Val Lys Val Leu Gly Ser Gly Ala Phe
                725                 730                 735
Gly Thr Val Tyr Lys Gly Ile Trp Ile Pro Asp Gly Glu Asn Val Lys
                740                 745                 750
Ile Pro Val Ala Ile Lys Val Leu Arg Glu Asn Thr Ser Pro Lys Ala
                755                 760                 765
Asn Lys Glu Ile Leu Asp Glu Ala Tyr Val Met Ala Gly Val Gly Ser
            770                 775                 780
Pro Tyr Val Ser Arg Leu Leu Gly Ile Cys Leu Thr Ser Thr Val Gln
785                 790                 795                 800
Leu Val Thr Gln Leu Met Pro Tyr Gly Cys Leu Leu Asp His Val Arg
                805                 810                 815
Glu His Arg Gly Arg Leu Gly Ser Gln Asp Leu Leu Asn Trp Cys Val
                820                 825                 830
Gln Ile Ala Lys Gly Met Ser Tyr Leu Glu Asp Val Arg Leu Val His
                835                 840                 845
Arg Asp Leu Ala Ala Arg Asn Val Leu Val Lys Ser Pro Asn His Val
850                 855                 860
Lys Ile Thr Asp Phe Gly Leu Ala Arg Leu Leu Asp Ile Asp Glu Thr
865                 870                 875                 880
Glu Tyr His Ala Asp Gly Gly Lys Val Pro Ile Lys Trp Met Ala Leu
                885                 890                 895
Glu Ser Ile Leu Arg Arg Arg Phe Thr His Gln Ser Asp Val Trp Ser
                900                 905                 910
Tyr Gly Val Thr Val Trp Glu Leu Met Thr Phe Gly Ala Lys Pro Tyr
                915                 920                 925
Asp Gly Ile Pro Ala Arg Glu Ile Pro Asp Leu Leu Glu Lys Gly Glu
            930                 935                 940
Arg Leu Pro Gln Pro Pro Ile Cys Thr Ile Asp Val Tyr Met Ile Met
945                 950                 955                 960
Val Lys Cys Trp Met Ile Asp Ser Glu Cys Arg Pro Arg Phe Arg Glu
                965                 970                 975
Leu Val Ser Glu Phe Ser Arg Met Ala Arg Asp Pro Gln Arg Phe Val
                980                 985                 990
Val Ile Gln Asn Glu Asp Leu Gly Pro Ser Ser Pro Met Asp Ser Thr
            995                 1000                1005
Phe Tyr Arg Ser Leu Leu Glu Asp Asp Asp Met Gly Asp Leu Val
        1010                1015                1020
Asp Ala Glu Glu Tyr Leu Val Pro Gln Gln Gly Phe Phe Ser Pro
        1025                1030                1035
Asp Pro Thr Pro Gly Thr Gly Ser Thr Ala His Arg Arg His Arg
        1040                1045                1050
Ser Ser Ser Thr Arg Ser Gly Gly Gly Glu Leu Thr Leu Gly Leu
        1055                1060                1065
Glu Pro Ser Glu Glu Gly Pro Pro Arg Ser Pro Leu Ala Pro Ser
        1070                1075                1080
Glu Gly Ala Gly Ser Asp Val Phe Asp Gly Asp Leu Ala Met Gly
        1085                1090                1095
Val Thr Lys Gly Leu Gln Ser Leu Ser Pro His Asp Leu Ser Pro
        1100                1105                1110
Leu Gln Arg Tyr Ser Glu Asp Pro Thr Leu Pro Leu Pro Pro Glu
        1115                1120                1125
```

-continued

```
Thr Asp Gly Tyr Val Ala Pro Leu Ala Cys Ser Pro Gln Pro Glu
    1130            1135                1140
Tyr Val Asn Gln Ser Glu Val Gln Pro Gln Pro Pro Leu Thr Pro
    1145            1150                1155
Glu Gly Pro Leu Pro Pro Val Arg Pro Ala Gly Ala Thr Leu Glu
    1160            1165                1170
Arg Pro Lys Thr Leu Ser Pro Gly Lys Asn Gly Val Val Lys Asp
    1175            1180                1185
Val Phe Ala Phe Gly Gly Ala Val Glu Asn Pro Glu Tyr Leu Val
    1190            1195                1200
Pro Arg Glu Gly Thr Ala Ser Pro Pro His Pro Ser Pro Ala Phe
    1205            1210                1215
Ser Pro Ala Phe Asp Asn Leu Tyr Tyr Trp Asp Gln Asn Ser Ser
    1220            1225                1230
Glu Gln Gly Pro Pro Pro Ser Asn Phe Glu Gly Thr Pro Thr Ala
    1235            1240                1245
Glu Asn Pro Glu Tyr Leu Gly Leu Asp Val Pro Val
    1250            1255                1260

<210> SEQ ID NO 9
<211> LENGTH: 3952
<212> TYPE: DNA
<213> ORGANISM: Rattus norvegicus

<400> SEQUENCE: 9
ccgggccgga gccgcaatga tcatcatgga gctggcggcc tggtgccgct gggggttcct      60
cctcgccctc ctgccccccg gaatcgcggg cacccaagtg tgtaccggca cagacatgaa     120
gttgcggctc cctgccagtc ctgagaccca cctggacatg ctccgccacc tgtaccaggg     180
ctgtcaggta gtgcagggca acttggagct tacctacgtg cctgccaatg ccagcctctc     240
attcctgcag gacatccagg aagttcaggg ttacatgctc atcgctcaca accaggtgaa     300
gcgcgtccca ctgcaaaggc tgcgcatcgt gagagggacc cagctctttg aggacaagta     360
tgccctggct gtgctagaca ccgagatcc tcaggacaat gtcgccgcct ccaccccagg     420
cagaacccca gaggggctgc gggagctgca gcttcgaagt ctcacagaga tcctgaaggg     480
aggagttttg atccgtggga accctcagct ctgctaccag acatggtttt gtggaagga     540
cgtcttccgc aagaataacc aactggctcc tgtcgatata gacaccaatc gttcccgggc     600
ctgtccacct tgtgcccccg cctgcaaaga caatcactgt tggggtgaga gtccggaaga     660
ctgtcagatc ttgactggca ccatctgtac cagtggttgt gcccggtgca agggccggct     720
gcccactgac tgctgccatg agcagtgtgc cgcaggctgc acgggcccca gcattctga     780
ctgcctggcc tgcctccact tcaatcatag tggtatctgt gagctgcact gcccagcct     840
cgtcacctac aacacagaca ccctttgagtc catgcacaac cctgagggtc gctacacctt     900
tggtgccagc tgcgtgacca cctgccccta caactacctg tctacggaag tgggatcctg     960
cactctggtg tgtcccccga ataaccaaga ggtcacagct gaggacggaa cacagcgttg    1020
tgagaaatgc agcaagccct gtgctcgagt gtgctatggt ctgggcatgg agcaccttcg    1080
aggggcgagg gccatcacca gtgacaatgt ccaggagttt gatggctgca gaagatctct    1140
gggagcctgg cattttgc cggagagctt tgatgggac ccctcctccg gcattgctcc    1200
gctgaggcct gagcagctcc aagtgttcga aaccctggag gagatcacag gttacctgta    1260
catctcagca tggccagaca gtctccgtga cctcagtgtc ttccagaacc ttcgaatcat    1320
```

```
tcggggacgg attctccacg atggcgcgta ctcattgaca ctgcaaggcc tggggatcca   1380
ctcgctgggg ctgcgctcac tgcgggagct gggcagtgga ttggctctga ttcaccgcaa   1440
cgcccatctc tgctttgtac acactgtacc ttgggaccag ctcttccgga acccacatca   1500
ggccctgctc cacagtggga accggccgga agaggattgt ggtctcgagg gcttggtctg   1560
taactcactg tgtgcccacg ggcactgctg ggggccaggg cccacccagt gtgtcaactg   1620
cagtcatttc cttcggggcc aggagtgtgt ggaggagtgc cgagtatgga aggggctccc   1680
ccgggagtat gtgagtgaca agcgctgtct gccgtgtcac cccgagtgtc agcctcaaaa   1740
cagctcagag acctgctttg gatcggaggc tgatcagtgt gcagcctgcg cccactacaa   1800
ggactcgtcc tcctgtgtgg ctcgctgccc cagtggtgtg aaaccggacc tctcctacat   1860
gcccatctgg aagtacccgg atgaggaggg catatgccag ccgtgcccca tcaactgcac   1920
ccactcctgt gtggatctgg atgaacgagg ctgcccagca gagcagagag ccagcccggt   1980
gacattcatc attgcaactg tagagggcgt cctgctgttc ctgatcttag tggtggtcgt   2040
tggaatccta atcaaacgaa ggagacagaa gatccggaag tatacgatgc gtaggctgct   2100
gcaggaaact gagttagtgg agccgctgac gcccagcgga gcaatgccca accaggctca   2160
gatgcggatc ctaaaagaga cggagctaag gaaggtgaag gtgcttggat caggagcttt   2220
tggcactgtc tacaagggca tctggatccc agatggggag aatgtgaaaa tccccgtggc   2280
tatcaaggtg ttgagagaaa acacatctcc taaagccaac aaagaaattc tagatgaagc   2340
gtatgtgatg gctggtgtgg gttctccgta tgtgtcccgc ctcctgggca tctgcctgac   2400
atccacagta cagctggtga cacagcttat gcccctacggc tgccttctgg accatgtccg   2460
agaacaccga ggtcgcctag gctcccagga cctgctcaac tggtgtgttc agattgccaa   2520
ggggatgagc tacctggagg acgtgcggct tgtacacagg gacctggctg cccggaatgt   2580
gctagtcaag agtcccaacc acgtcaagat tacagatttc gggctggctc ggctgctgga   2640
cattgatgag acagagtacc atgcagatgg gggcaaggtg cccatcaaat ggatggcatt   2700
ggaatctatt ctcagacgcc ggttcaccca tcagagtgat gtgtggagct atggagtgac   2760
tgtgtgggag ctgatgactt ttgggggccaa accttacgat ggaatcccag cccgggagat   2820
ccctgatttg ctggagaagg gagaacgcct acctcagcct ccaatctgca ccattgatgt   2880
ctacatgatt atggtcaaat gttggatgat tgactctgaa tgtcgcccga gattccggga   2940
gttggtgtca gaattttcac gtatggcgag ggaccccccag cgttttgtgg tcatccagaa   3000
cgaggacttg ggcccatcca gccccatgga cagtaccttc taccgttcac tgctggaaga   3060
tgatgacatg ggtgacctgg tagacgctga agagtatctg gtgccccagc agggattctt   3120
ctcccccgga ccctaccccag gcactgggag cacagcccat agaaggcacc gcagctcgtc   3180
caccaggagt ggaggtggtg agctgacact gggcctggag ccctcggaag aagggccccc   3240
cagatctcca ctggctccct cggaaggggc tggctccgat gtgtttgatg gtgacctggc   3300
aatgggggta accaaagggc tgcagagcct ctctccacat gacctcagcc ctctacagcg   3360
gtacagcgag gaccccacat acctctgcc ccccgagact gatggctatg ttgctcccct   3420
ggcctgcagc cccagcccg agtatgtgaa ccaatcagag gttcagcctc agcctccttt   3480
aaccccagag ggtcctctgc ctcctgtccg gcctgctggt gctactctag aaagacccaa   3540
gactctctct cctgggaaga atggggttgt caaagacgtt tttgccttcg ggggtgctgt   3600
ggagaacccct gaatacttag taccgagaga aggcactgcc tctccgcccc acccttctcc   3660
```

-continued

```
tgccttcagc ccagcctttg acaacctcta ttactgggac cagaactcat cggagcaggg    3720
gcctccacca agtaactttg aagggacccc cactgcagag aaccctgagt acctaggcct    3780
ggatgtacct gtatgagacg tgtgcagacg tcctgtgctt tcagagtggg gaaggcctga    3840
cttgtggtct ccatcgccac aaagcaggga gagggtcctc tggccacatt acatccaggg    3900
cagacggctc taccaggaac ctgccccgag gaacctttcc ttgctgcttg aa            3952
```

<210> SEQ ID NO 10
<211> LENGTH: 32
<212> TYPE: PRT
<213> ORGANISM: Listeria monocytogenes
<400> SEQUENCE: 10

```
Lys Glu Asn Ser Ile Ser Ser Met Ala Pro Pro Ala Ser Pro Pro Ala
1               5                   10                  15

Ser Pro Lys Thr Pro Ile Glu Lys Lys His Ala Asp Glu Ile Asp Lys
            20                  25                  30
```